(12) United States Patent
Paraschac et al.

(10) Patent No.: US 8,074,654 B2
(45) Date of Patent: Dec. 13, 2011

(54) IMPLANTABLE DEVICES, SYSTEMS, AND METHODS FOR MAINTAINING DESIRED ORIENTATIONS IN TARGETED TISSUE REGIONS

(75) Inventors: Joseph Paraschac, San Jose, CA (US); Lionel M Nelson, Los Altos Hills, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 658 days.

(21) Appl. No.: 11/820,173

(22) Filed: Jun. 18, 2007

(65) Prior Publication Data

US 2008/0066765 A1   Mar. 20, 2008

Related U.S. Application Data

(60) Continuation-in-part of application No. 11/656,699, filed on Jan. 23, 2007, now Pat. No. 7,367,340, which is a continuation-in-part of application No. 10/718,254, filed on Nov. 20, 2003, now Pat. No. 7,360,542, which is a division of application No. 10/236,455, filed on Sep. 6, 2002, now Pat. No. 7,216,648.

(60) Provisional application No. 60/903,741, filed on Feb. 27, 2007.

(51) Int. Cl.
*A61F 13/00*   (2006.01)

(52) U.S. Cl. ........................................ 128/848; 128/846
(58) Field of Classification Search .................. 128/846, 128/848, 859–861; 433/6; 602/902; 606/148, 606/151, 187, 215, 222, 224, 228–230, 154–155
See application file for complete search history.

(56) References Cited

U.S. PATENT DOCUMENTS

| | | | | |
|---|---|---|---|---|
| 3,496,936 A * | 2/1970 | Gores | ........................ | 128/861 |
| 3,608,166 A * | 9/1971 | Gruget | ........................ | 28/112 |
| 4,664,109 A * | 5/1987 | Rasocha | ................. | 128/207.14 |
| 4,741,330 A * | 5/1988 | Hayhurst | ...................... | 606/144 |
| 5,330,503 A * | 7/1994 | Yoon | ............................. | 606/223 |
| 5,342,376 A * | 8/1994 | Ruff | .............................. | 606/151 |
| 5,353,810 A * | 10/1994 | Kittelsen et al. | .............. | 128/862 |
| 5,683,417 A * | 11/1997 | Cooper | ........................ | 606/223 |
| 6,408,851 B1 * | 6/2002 | Karell | .......................... | 128/848 |
| 6,955,172 B2 * | 10/2005 | Nelson et al. | ................. | 128/848 |
| 2003/0149447 A1 * | 8/2003 | Morency et al. | ............. | 606/228 |
| 2006/0070626 A1 * | 4/2006 | Frazier et al. | ............ | 128/207.14 |

\* cited by examiner

*Primary Examiner* — Michael A. Brown

(57) ABSTRACT

At least one elongated body is sized and configured for implantation in a desired orientation in a tissue region in an airway. An array of projections extends from the elongated body and is resiliently coupled to the elongated body. The array or projections is in a normally biased outward extending condition sized and configured to engage tissue and resist a reorientation of the elongated body within the tissue region out of the desired orientation after implantation of the elongated body in the tissue region. The array of projections is sized and configured to resiliently yield by flexing inward against the elongated body during implantation of the elongated body in the tissue region.

25 Claims, 42 Drawing Sheets

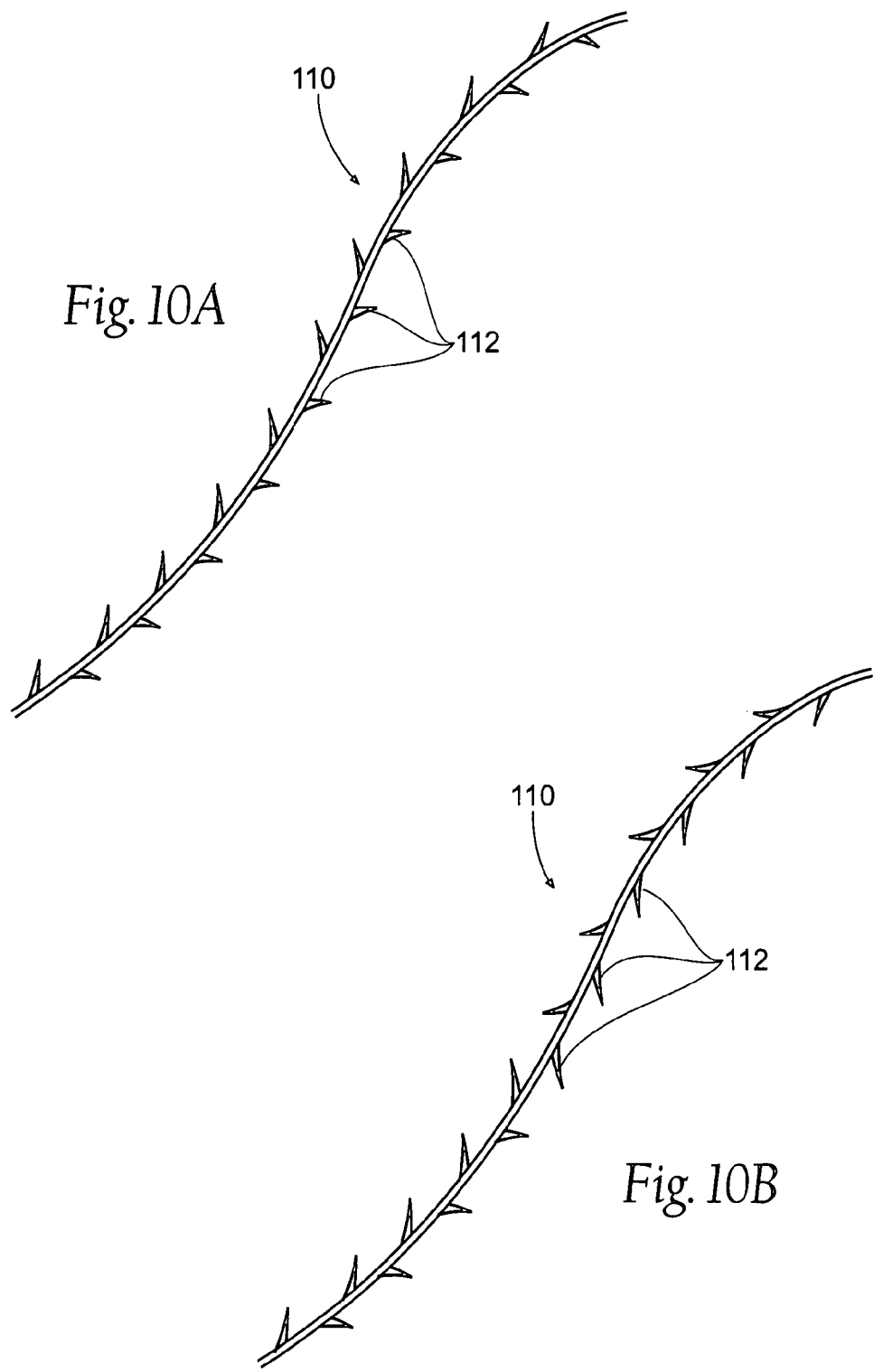

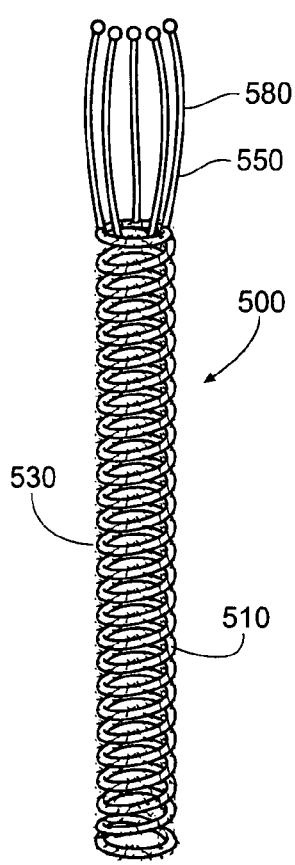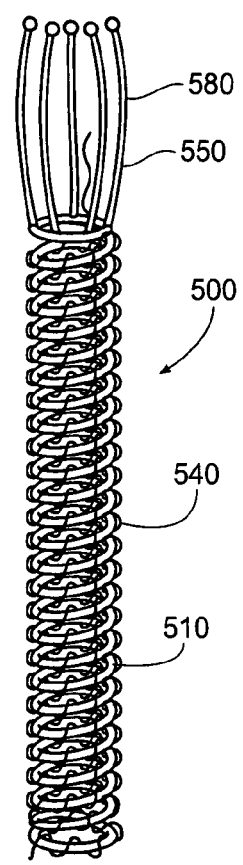
*Fig. 33A*  *Fig. 33B*
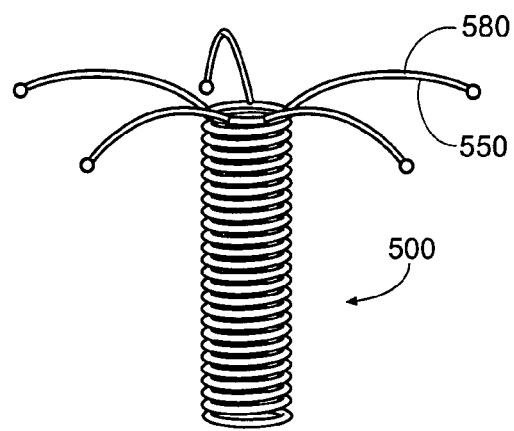
*Fig. 33C*

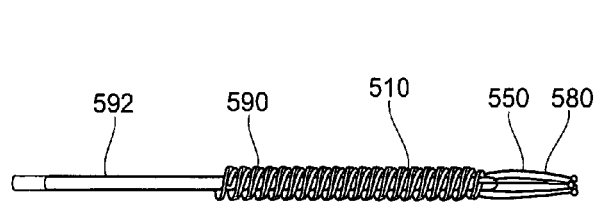
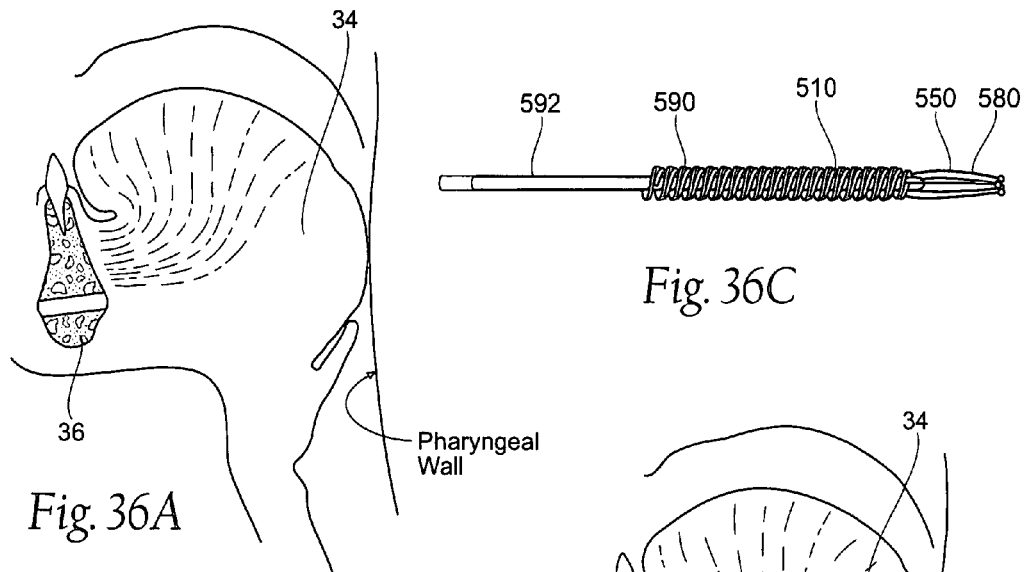
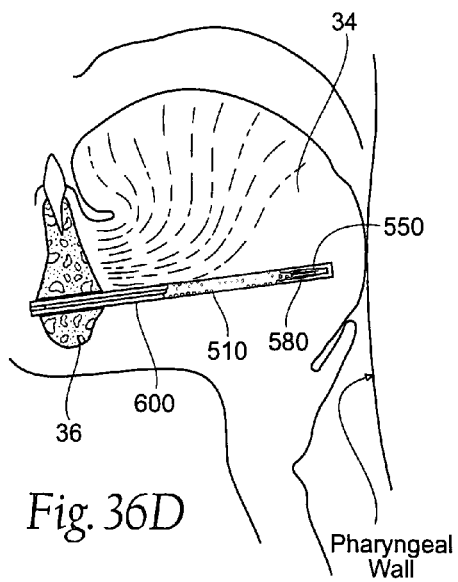
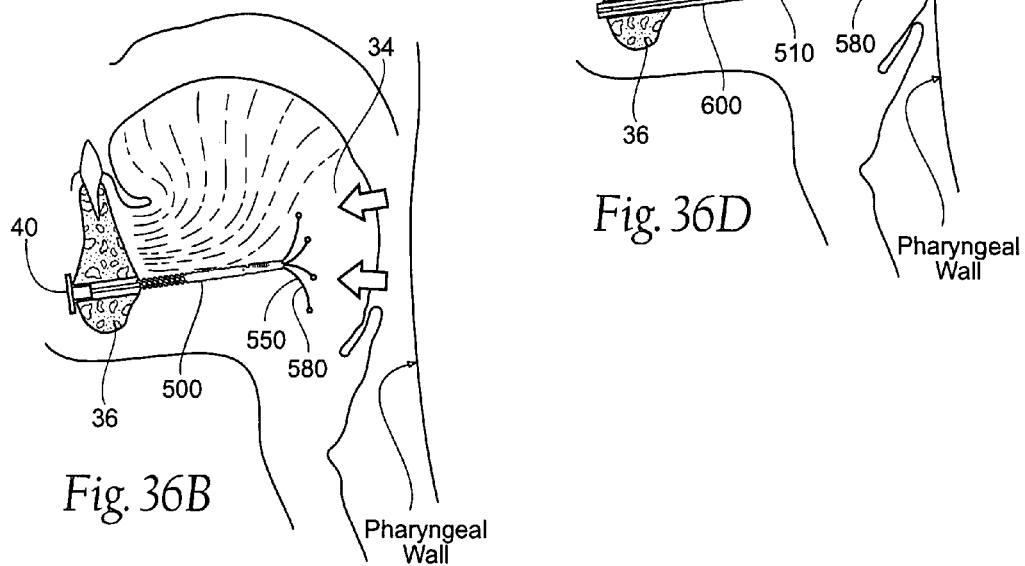
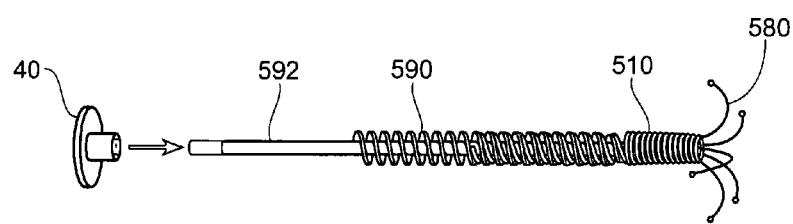

IMPLANTABLE DEVICES, SYSTEMS, AND METHODS FOR MAINTAINING DESIRED ORIENTATIONS IN TARGETED TISSUE REGIONS

RELATED APPLICATIONS

This application is a continuation-in-part of U.S. patent application Ser. No. 11/656,699, filed Jan. 23, 2007, now U.S. Pat. No. 7,367,340 and entitled "Systems and Methods for Moving and/or Restraining Tissue in the Upper Respiratory System," which is a division of U.S. patent application Ser. No. 10/236,455, filed Sep. 6, 2002, now U.S. Pat. No. 7,216,648 and entitled "Systems and Methods for Moving and/or Restraining Tissue in the Upper Respiratory System," which are incorporated herein by reference. This application is also a continuation-in-part of U.S. patent application Ser. No. 10/718,254, filed Nov. 20, 2003, now U.S. Pat. No. 7,360,542 end entitled "Devices, Systems and Methods to Fixate Tissue Within the Regions of the Body Such as the Pharyngeal Conduit," which is also incorporated herein by reference. This application also claims the benefit of U.S. Provisional Application Ser. No. 60/903,741, filed Feb. 27, 2007, and entitled "Devices, Systems, and Methods to Move or Restrain the Hyoid Bone," which is incorporated herein by reference.

FIELD OF THE INVENTION

The invention is directed to devices, systems, and methods for the treatment of sleep disordered breathing including snoring and obstructive sleep apnea.

BACKGROUND OF THE INVENTION

I. Characteristics of Sleep Apnea

First described in 1965, sleep apnea is a breathing disorder characterized by brief interruptions (10 seconds or more) of breathing during sleep. Sleep apnea is a common but serious, potentially life-threatening condition, affecting as many as 18 million Americans. Snoring also can occur independent of or during a sleep apneic event.

There are two types of sleep apnea: central and obstructive. Central sleep apnea, occurs when the brain fails to send the appropriate signal to the breathing muscles to initiate respirations, e.g., as a result of brain stem injury or damage. Mechanical ventilation is the only treatment available to ensure continued breathing.

Obstructive sleep apnea (OSA) is far more common. Normally, the muscles of the upper part of the throat keep the airway open to permit air flow into the lungs. When the muscles at the base of the tongue and the uvula (the small fleshy tissue hanging from the center of the back of the throat) relax and sag, the relaxed tissues may vibrate as air flows past the tissues during breathing, resulting in snoring. Snoring affects about half of men and 25 percent of women—most of whom are age 50 or older.

In more serious cases, the airway becomes blocked, making breathing labored and noisy, or even stopping it altogether. In a given night, the number of involuntary breathing pauses or "apneic events" may be as high as 20 to 30 or more per hour. These breathing pauses are almost always accompanied by snoring between apnea episodes, although not everyone who snores has the condition. Sleep apnea can also be characterized by choking sensations.

Lack of air intake into the lungs results in lower levels of oxygen and increased levels of carbon dioxide in the blood. The altered levels of oxygen and carbon dioxide alert the brain to resume breathing and cause arousal. The frequent interruptions of deep, restorative sleep often lead to early morning headaches, excessive daytime sleepiness, depression, irritability, and learning and memory difficulties.

The medical community has become aware of the increased incidence of heart attacks, hypertension and strokes in people with moderate or severe obstructive sleep apnea. It is estimated that up to 50 percent of sleep apnea patients have high blood pressure.

Upon an apneic event, the sleeping person is unable to continue normal respiratory function and the level of oxygen saturation in the blood is reduced. The brain will sense the condition and cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep and associated daytime fatigue.

Although some apneic events are normal in all persons and mammals, the frequency of blockages will determine the seriousness of the disease and opportunity for health damage. When the incidence of blockage is frequent, corrective action should be taken.

II. The Anatomy of the Upper Airway

As FIG. 1 shows, the upper airway consists of a conduit that begins at the nasal valve, situated in the tip of the nose, and extends to the larynx, which is also called the voice box because it houses the vocal cords. The pharynx (which, in Greek, means "throat") is a cone-shaped passageway in the upper airway that leads from the oral and nasal cavities in the head to the esophagus and larynx. The pharynx serves both respiratory and digestive functions. Both circular and longitudinal muscles are present in the walls of this organ, which are called the pharyngeal walls. The circular muscles form constrictions that help push food to the esophagus and prevent air from being swallowed, while the longitudinal muscles lift the walls of the pharynx during swallowing.

The pharynx consists of three main divisions. The superior portion is the nasal pharynx, the back section of the nasal cavity. The nasal pharynx connects to the second region, the oral pharynx, by means of a passage called an isthmus. The oral pharynx begins at the back of the mouth cavity and continues down the throat to the epiglottis, a flap of tissue that covers the air passage to the lungs and that channels food to the esophagus. The isthmus connecting the oral and nasal regions allows humans to breathe through either the nose or the mouth. The third region is the laryngeal pharynx, which begins at the epiglottis and leads down to the esophagus. Its function is to regulate the passage of air to the lungs and food to the esophagus. Air from the nasal cavity flows into the larynx, and food from the oral cavity is routed to the esophagus directly behind the larynx. The epiglottis, a cartilaginous, leaf-shaped flap, functions as a lid to the larynx and, during the act of swallowing, controls the traffic of air and food.

The mouth cavity marks the start of the digestive tube. Oval in shape, it consists of two parts: the vestibule and the mouth cavity proper.

The vestibule is the smaller outer portion, delimited externally by the lips and cheeks and internally by the gums and teeth. It connects with the body surface through the rima or orifice of the mouth. The vestibule receives the secretion of the parotid salivary glands and connects when the jaws are closed with the mouth cavity proper by an aperture on both sides behind the wisdom teeth, and by narrow clefts between opposing teeth.

The mouth cavity proper contains the tongue and is delimited laterally and in the front by the alveolar arches with the teeth therein contained. The alveolar process on the upper jaw is contained in the maxillae, whereas the alveolar process on the lower jaw is contained in the mandible. The mandible is a U-shaped bone that supports the mandibular (lower) teeth.

The mouth cavity proper receives the secretion from the submaxillary and sublingual salivary glands. The mouth cavity proper connects with the pharynx by a constricted aperture called isthmus faucium.

The tongue (see FIG. 1B) is a mobile muscular organ that can assume a variety of shapes and positions. The tongue comprises extrinsic and intrinsic muscles. The extrinsic muscles (genioglossus, hyoglossus, styloglossus, and palatoglossus) (shown in FIG. 1B) have their origin in other structures and attach to the tongue. Their function is to move the tongue and, at times, change its shape. The intrinsic muscles of the tongue (superior longitudinal, inferior longitudinal, transverse, vertical) (not shown with particularity) are attached entirely within the tongue work to modify the shape of the tongue. The inferior surface of the tongue (see FIG. 1C) is covered with a thin, transparent mucous membrane through which one can see the underlying veins. With the tongue raised (as shown in FIG. 1C), the lingual frenulum is exposed. The lingual frenulum is a large, midline fold of mucosa that connects the tongue to the floor of the mouth, while allowing the anterior part of the tongue to move freely.

The tongue has a relatively fixed inferior part that is attached to the hyoid bone and mandible. The rest of the tongue is called the body of the tongue. It is essentially a mass of muscles (that is mostly covered by mucous membrane. The muscles in the tongue do not act in isolation. Some muscles perform multiple actions with parts of one muscle acting independently producing different, sometimes antagonistic, actions.

The tongue is partly in the mouth or oral cavity and partly in the pharynx. At rest, it occupies essentially the entire oral cavity. The posterior part of the tongue demarcates the posterior boundary of the oral cavity. Its mucous membrane is thick and freely movable.

The tongue is involved with mastication, taste, articulation, and oral cleansing. Its two main functions are forming words during speaking and squeezing food into the pharynx when swallowing.

The epiglottis is a protective fold of the cartilage posterior to the base of the tongue and in front of the larynx. When a human breathes, the epiglottis stands up, allowing air to go into the larynx and lungs. During swallowing, the epiglottis folds back to cover the larynx and keep food from entering the windpipe and lungs. Once the swallowing is over, the epiglottis resumes its upright position.

The palate forms the arched roof of the oral or mouth cavity (the mouth) and the floor of the nasal cavities (the nose). It separates the oral cavity from the nasal cavities and the nasal pharynx. The palate consists of two regions—the hard palate anteriorly and the soft palate posteriorly.

The hard palate is vaulted and defines the space filled by the tongue when it is at rest. The hard palate is bounded in the front and laterally by the alveolar arches and gums and in the back by the soft palate. A dense structure made up by the periosteum and the mucous membrane of the mouth covers the hard palate. The linear raphé lies along the middle line of the hard palate. The hard palate has a hard bony skeleton, hence its name.

The soft palate has no bony skeleton, hence its name. The soft palate is a movable fold, suspended from the posterior border of the hard palate and forms an incomplete dividing line (septum) between the mouth and the pharynx. The soft palate comprises a mucous membrane that envelops muscular fibers, an aponeurosis, vessels, nerves, adenoid tissue, and mucous glands. When the soft palate is relaxed and hanging, the anterior surface is concave and follows the same line as the roof of the mouth. The posterior surface of the soft palate is convex and is a continuance of the mucous membrane that covers the bottom part of the nasal cavities. The upper boundary of the soft palate attaches to the hard palate; the sides become part of the pharynx; and the lower boundary is free. The lower boundary which hangs down, separating the mouth and the pharynx is known as the palatine velum. In the middle of the lower boundary, the small, fleshy cone-shaped protuberance is called the uvula; the uvula prevents the food from entering the nasopharynx and the muscles of the soft palate push the food down into the pharynx. The arches are located laterally and downwardly from the uvula. These arches are called the glossopalatine arch (the anterior arch) and the pharyngopalatine arch (the posterior arch). The palatine aponeurosis is a thin, firm fiber-filled lamella which gives support to the muscles and makes the soft palate strong.

The soft palate is suspended from the posterior border of the hard palate. It extends posteriorly and inferiorly as a curved free margin from which hangs a conical process, called the uvula; closely following behind the soft palate are the palatoglossal and the palatopharyngeal arches, respectively. Muscles arise from the base of the cranium and descend into the soft palate. The muscles allow the soft palate to be elevated during swallowing into contact with the posterior pharyngeal wall. The muscles also allow the soft palate to be drawn inferiorly during swallowing into contact with the posterior part of the tongue.

The soft palate is thereby very dynamic and movable. When a person swallows, the soft palate initially is tensed to allow the tongue to press against it, to squeeze the bolus of food to the back of the mouth. The soft palate is then elevated posteriorly and superiorly against the pharyngeal wall, acting as a valve to prevent passage of food into the nasal cavity.

Caudal to the soft palate, the hyoid bone is situated at the base of the tongue in the anterior part of the neck at the level of the C3 vertebra and in the angle between the mandible and the thyroid cartilage of the larynx, the voice box. It is a symmetric U-shaped bone (see FIG. 2B), comprising a body with greater horns and lesser horns, which serve as points of attachment for numerous muscles in the tongue, pharynx, and the anterolateral part of the neck (see FIGS. 3A to 3D).

The hyoid bone does not articulate with any other bone. It serves a purely anchoring function for muscles. The hyoid bone is suspended from the styloid processes of the temporal bones by the stylohyoid ligaments and is firmly bound to the thyroid cartilage. Functionally, the hyoid bone serves as an attachment point for numerous muscles and a prop to keep the airway open. The primary function of the hyoid bone is to serve as an anchoring structure for the tongue.

FIGS. 3A to 3D show some of the numerous muscles that are attached to the hyoid bone (as does FIG. 1B). The muscles attached to the hyoid bone include the middle pharyngeal constrictor muscle (see FIG. 3A), which attaches at the end of the greater horns. The middle pharyngeal constrictor muscle, together with the superior and inferior pharyngeal constrictor muscles (also shown in FIG. 3A), extend along the upper airway. As before stated, a change in muscle function of the pharyngeal constrictor muscles can lead to pharyngeal narrowing and collapse.

The muscles attached to the hyoid bone also include the hyoglossus muscles (see FIGS. 3B and 3D, as well as FIG. 1B). The hyoglossus muscles originate along the entire length of each greater horn and also from the body of the hyoid. The hyoglossus muscles are inserted into the posterior half or more of the sides of the tongue, as FIG. 3D best shows. The hyoid bone anchors the hyoglossus muscles when they contract, to depress the tongue and to widen the oral cavity, thereby opening the airway.

The muscles attached to the hyoid bone also include the two geniohyoid muscles (see FIG. 3C). The geniohyoid muscles originate close to the point at which the two halves of the lower jaw meet; the fibers of the muscles extend downward and backward, close to the central line, to be inserted into the body of the hyoid bone. Contraction of the geniohyoid muscles pulls the hyoid bone upward and forward, shortening the floor of the mouth and widening the pharynx.

Inserting into the middle part of the lower border of the hyoid bone are the sternohyoids (see FIG. 3C). The sternohyoids are long muscles arising from the breastbone and collarbone and running upward and toward each other in the neck. The sternohyoids depress the hyoid bone after it has been elevated during swallowing.

Other muscles attached to the hyoid bone are the two mylohyoid muscles (see FIG. 3C), which form a sort of diaphragm for the floor of the mouth, elevating the floor of the mouth and tongue during swallowing; the thyrohyoid (see FIG. 3C), arising from the thyroid cartilage of the larynx, which elevates the larynx; and the omohyoid (see FIG. 3C), which originates from the upper margin of the shoulder blade, which depresses, retracts, and steadies the hyoid bone.

The position of the hyoid bone with relation to the muscles attached to it has been likened to that of a ship steadied as it rides when anchored "fore and aft." Through the muscle attachments, the hyoid plays an important role in mastication, in swallowing, and in voice production.

The larynx, also known as the organ of voice, is part of the upper respiratory tract. As FIG. 1A shows, the larynx is situated between the base of the tongue and the trachea; vertically, the larynx's position corresponds to the C4, C5, and C6 vertebrae, although this location is higher in females and during childhood. FIG. 2A shows the nine cartilages of the larynx: a thyroid, a cricoid, two arytenoids, two corniculate, two cuneiform, and an epiglottis.

The larynx comprises extrinsic ligaments which link the thyroid cartilage and the epiglottis with the hyoid bone and the cricoid cartilage with the trachea (see FIG. 2B). The hyothyroid membrane and the lateral hyothyroid ligament attach the thyroid cartilage to the hyoid bone. The hyoepiglottic ligament connects the epiglottis to the upper border of the hyoid bone. The cricotracheal ligament attaches the cricoid cartilage to the first ring of the trachea (see FIG. 2B).

III. Sleep and the Anatomy of the Upper Airway

Although all tissue along this conduit is dynamic and responsive to the respiratory cycle, only the pharynx is totally collapsible. The pharyngeal structures and individual anatomic components within this region include the pharyngeal walls, the base of the tongue, the soft palate with uvula, and the epiglottis.

The cross-sectional area of the upper airway varies with the phases of the respiratory cycle. At the initiation of inspiration (Phase I), the airway begins to dilate and then to remain relatively constant through the remainder of inspiration (Phase II). At the onset of expiration (Phase III) the airway begins to enlarge, reaching maximum diameter and then diminishing in size so that at the end of expiration (Phase IV), it is at its narrowest, corresponding to the time when the upper airway dilator muscles are least active, and positive intraluminal pressure is lowest. The upper airway, therefore, has the greatest potential for collapse and closure at end-expiration [ref: Schwab R J, Goldberg A N. Upper airway assessment: radiographic and other imaging techniques. Otolaryngol Clin North Am 1998, 31:931-968].

Sleep is characterized by a reduction in upper airway dilator muscle activity. For the individual who snores or has obstructive sleep apnea (OSA) and perhaps the other disorders which comprise much of the group of entities called obstructive sleep-disordered breathing (SDB), it is believed that this change in muscle function causes pharyngeal narrowing and collapse. Two possible etiologies for this phenomenon in OSA patients have been theorized. One is that these individuals reduce the airway dilator muscle tone more than non-apneics during sleep (the neural theory). The other is that all individuals experience the same reduction in dilator activity in sleep, but that the apneic has a pharynx that is structurally less stable (the anatomic theory). Both theories may in fact be contributors to OSA, but current studies seem to support that OSA patients have an intrinsically structurally narrowed and more collapsible pharynx. [Ref: Isono S. Remmers J, Tanaka A Sho Y, Sato J, Nishino T. Anatomy of pharynx in patients with obstructive sleep apnea and in normal subjects. J Appl Physiol 1997:82:1319-1326.] Although this phenomenon is often accentuated at specific sites, such as the velopharyngeal level [Isono], studies of closing pressures [Isono] support dynamic fast MRI imaging that shows narrowing and collapse usually occurs along the entire length of the pharynx. [Ref: Shellock F G, Schatz C J, Julien P, Silverman J M, Steinberg F, Foo T K F, Hopp M L, Westbrook P R. Occlusion and narrowing of the pharyngeal airway in obstructive sleep apnea: evaluation by ultrafast spoiled GRASS MR imaging. Am J of Roentgenology 1992:158: 1019-1024].

IV. Treatment Options

To date, the only treatment modality that addresses collapse along the entire upper airway is mechanical positive pressure breathing devices, such as continuous positive airway pressure (CPAP) machines. All other modalities, such as various surgical procedures and oral appliances, by their nature, address specific sectors of the airway (such as palate, tongue base and hyoid levels), but leave portions of pharyngeal wall untreated. This may account for the considerably higher success rate of CPAP over surgery and appliances in controlling OSA. Although CPAP, which in essence acts as an airway splint for the respiratory cycle, is highly successful, it has some very significant shortcomings. It can be cumbersome to wear and travel with, difficult to accept on a social level, and not tolerated by many (for reasons such as claustrophobia, facial and nasal mask pressure sores, airway irritation). These factors have lead to a relatively poor long-term compliance rate. One study has shown that 65% of patients abandon their CPAP treatment in 6 months. Other current treatments for OSA include genioglossal advancement (GA), maxillomandibular advancement (MA), and hyoid myotomy. InfluENT Medical offers a genioglossus advancement procedure where suture loop is passed through the tongue and anchored to a screw essentially inserted into the mandible. In another procedure, hyoid myotomy and suspension, the hyoid bone is advanced using a suture tied to the hyoid bone anchors the structure to two screws placed in the mandible. These treatments involve highly invasive surgical procedures and a long recovery time, and therefore have relatively low patient appeal.

The need remains for simple, minimally invasive, cost-effective devices, systems, and methods for reducing or preventing sleep disordered breathing events.

SUMMARY OF THE INVENTION

Devices, systems, and methods are provided by maintaining tissue regions in desired orientation in or along an airway, e.g., for reducing or preventing snoring and/or sleep disordered breathing events, such as sleep apnea.

In one aspect, the devices, systems, and methods provide an implant system comprising at least one elongated body sized and configured for implantation in a desired orientation in a tissue region in an airway. An array of projections extends from the elongated body and is resiliently coupled to the elongated body. The array or projections is in a normally biased outward extending condition sized and configured to engage tissue and resist a reorientation of the elongated body within the tissue region out of the desired orientation after implantation of the elongated body in the tissue region. The array of projections is sized and configured to resiliently yield by flexing inward against the elongated body during implantation of the elongated body in the tissue region.

In one embodiment, the desired orientation of the elongated body includes a state of tension, and a component can be further provided to adjust the state of tension.

In various embodiments, the elongated body can be sized and configured for implantation in a desired orientation in a palate, or in a uvula, or in a tongue, or in an epiglottis, or in a muscle along an upper respiratory tract.

In various embodiments, a tissue anchor and/or a bone anchor can be coupled to the elongated body.

In one embodiment, an implantation tool can be provided that is sized and configured to be introduced into the tissue region and have an interior bore accommodating passage of the elongated body for implantation in the tissue region.

In another aspect, the devices, systems, and methods provide a method comprising selecting a tissue region in an airway, and providing at least one elongated body sized and configured for implantation in a desired orientation in the tissue region. The elongated body includes an array of projections extending from the elongated body. The array of projections is resiliently coupled to the elongated body in a normally biased outward extending condition sized and configured to engage tissue and resist a reorientation of the elongated body within the tissue region out of the desired orientation after implantation of the elongated body in the tissue region. The array of projections is sized and configured to resiliently yield by flexing inward against the elongated body during implantation of the elongated body in the tissue region. The method implants the at least one elongated body to stabilize a desired orientation of the tissue region.

In various embodiments, the tissue region selected can include a palate, or a uvula, or a tongue, or an epiglottis, or a muscle along an upper respiratory tract.

In one embodiment, the method can include placing the at least one elongated body in a state of tension in the tissue region, e.g., by anchoring the at least one elongated body to tissue or to bone.

BRIEF DESCRIPTION OF THE DRAWINGS

FIG. 2A shows the cartilages of the larynx while FIG. 2B shows an anterolateral view of the ligaments of the larynx.

FIG. 5A shows a sagittal view of a human suffering from sleep apnea due to abnormalities in the soft palate. FIG. 5B shows the elongated body of FIG. 4A implanted in the human of FIG. 5A.

FIG. 6A shows a sagittal view of a human suffering from sleep apnea due to abnormalities in the uvula. FIG. 6B shows the elongated body of FIG. 4A implanted in the human of FIG. 6A.

FIG. 7A shows a sagittal view of a human suffering from sleep apnea due to abnormalities in the tongue. FIG. 7B shows the elongated body of FIG. 4A implanted in the human of FIG. 7A.

FIG. 8A shows a sagittal view of a human suffering from sleep apnea due to abnormalities in the epiglottis. FIG. 8B shows the elongated body of FIG. 4A implanted in the human of FIG. 8A.

FIG. 9A shows a sagittal view of a human suffering from sleep apnea due to abnormalities in the upper respiratory muscles. FIG. 9B shows the elongated body of FIG. 4A implanted in the human of FIG. 9A.

FIG. 10A shows an illustrative portion of an elongated body comprising a barbed suture with unidirectional barbs.

FIG. 10B shows an illustrative portion of an elongated body comprising a barbed suture with multidirectional barbs.

FIG. 11A shows an illustrative instrument for inserting barbed sutures into the palate. FIG. 11B is a side cross-sectional view of a portion of the hard palate and the soft palate with an illustrative instrument for inserting barbed sutures inserted in the palate. FIG. 11C is a side cross-sectional view of the hard palate and the soft palate with an illustrative instrument for inserting barbed sutures and illustrative barbed sutures threaded through the instrument. FIG. 11D is a side cross-sectional view of the hard palate and the soft palate with an illustrative end piece. FIG. 11E is a side cross-sectional view of the hard palate and the soft palate with barbed sutures and end piece inserted.

FIG. 26A is a perspective view of an elastomeric body in its relaxed state. FIG. 26B is a perspective view of an elastomeric body of 26A in a slightly extended state. FIG. 26C is an end view of the elastomeric body of FIG. 26A. FIG. 26D is a perspective view of the elastomeric body of FIG. 26A in an extended state.

FIG. 27A is a perspective view of an elastomeric body in its relaxed state. FIG. 27B is a perspective view of an elastomeric body of 27A in a slightly extended state. FIG. 27C is an end view of the elastomeric body of FIG. 27A. FIG. 27D is a perspective view of the elastomeric body of FIG. 27A in an extended state.

FIG. 28A is a perspective view of an elastomeric body in its relaxed state. FIG. 28B is a perspective view of the elastomeric body of FIG. 28A in an extended state.

FIG. 29A is a perspective view of an elastomeric body in its relaxed state. FIG. 29B is a perspective view of the elastomeric body of FIG. 29A in an extended state.

FIG. 33A is a perspective view of the elastomeric body of FIG. 30B further including a daisy anchor.

FIG. 33B is a perspective view of the elastomeric body of FIG. 30A further including a daisy anchor.

FIG. 33C is a perspective view of the elastomeric body of FIG. 33A or 33B wherein the spring has returned to its relaxed state and the daisy anchor has deployed.

FIGS. 36A to 36E show an elastomeric body coupled to a spring expander and a method of inserting the coupled elastomeric body and spring expander.

DESCRIPTION OF PREFERRED EMBODIMENTS

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

This specification discloses various methods, systems, and devices to maintain or aid in maintaining a patent, or open, airway. However, while the various methods, systems, and devices have application in procedures requiring the restriction of tissue collapse in and/or around the body, such as a passageway within the body, the various devices, systems, and methods are not necessarily restricted to tissue-based applications.

The devices, systems, and methods are particularly well suited for treating sleep disordered breathing, including sleep apnea. For this reason, the devices, systems, and methods will be described in this context. It should however be appreciated that the disclosed devices, systems, and methods are applicable for use in treating other dysfunctions elsewhere in the body, which are not necessarily sleep disorder related.

I. Anatomical Considerations and Sleep Apnea

In human beings the tongue is an organ that undergoes a wide variety of movements, partly because it is involved in a broad range of activities, including speech, eating and swallowing. When a human is awake, the tongue normally moves in an up and forward position. When a human is asleep, the muscles of the tongue relax and the tongue is able to move in an even broader range of directions. This movement can occur laterally, posteriorly, anteriorly, cranially, caudally, in a rolling manner, or any combination thereof.

The tongue can move in conjunction with other structures (i.e. tongue and pharyngeal wall coming together or tongue and palate coming together) or independently of other structures, such as tongue movement without palate, posterior wall, or epiglottis movement.

Sleep apnea occurs when the airway becomes obstructed. Hypopnea occurs when the airway is partially obstructed. Sleep apnea can take many forms. The closure of the airway can occur at any number of anatomical structures along the airway, including any combination of the tongue, soft palate, epiglottis, pharyngeal walls, and hyoid bone. In particular, the tongue may collapse with respect to the pharyngeal wall, or both the base of the tongue and the pharyngeal wall may collapse at the same time. Thus, sleep apnea may be treated by preventing the collapse of the specific anatomical structures.

Figure 1A:
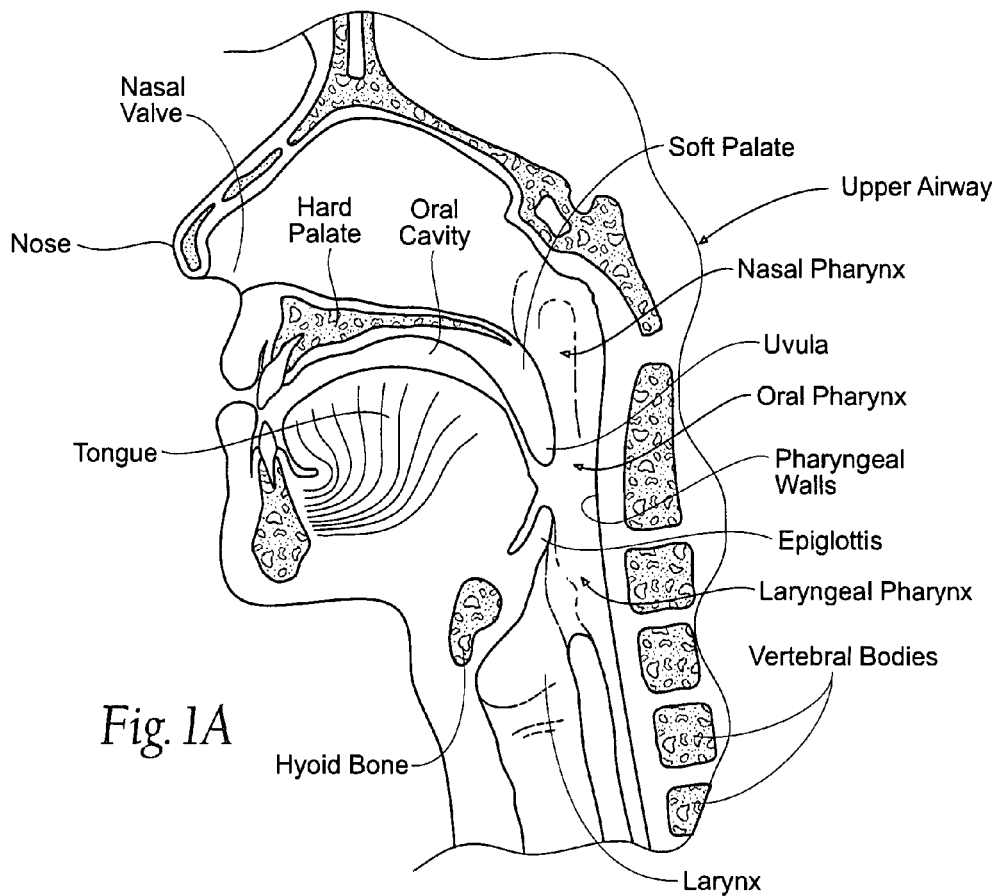
FIG. 1A is an anatomical sagittal cross-section of a normal human nasal airway, oral cavity, and oropharyrnx.
Figure 1B:
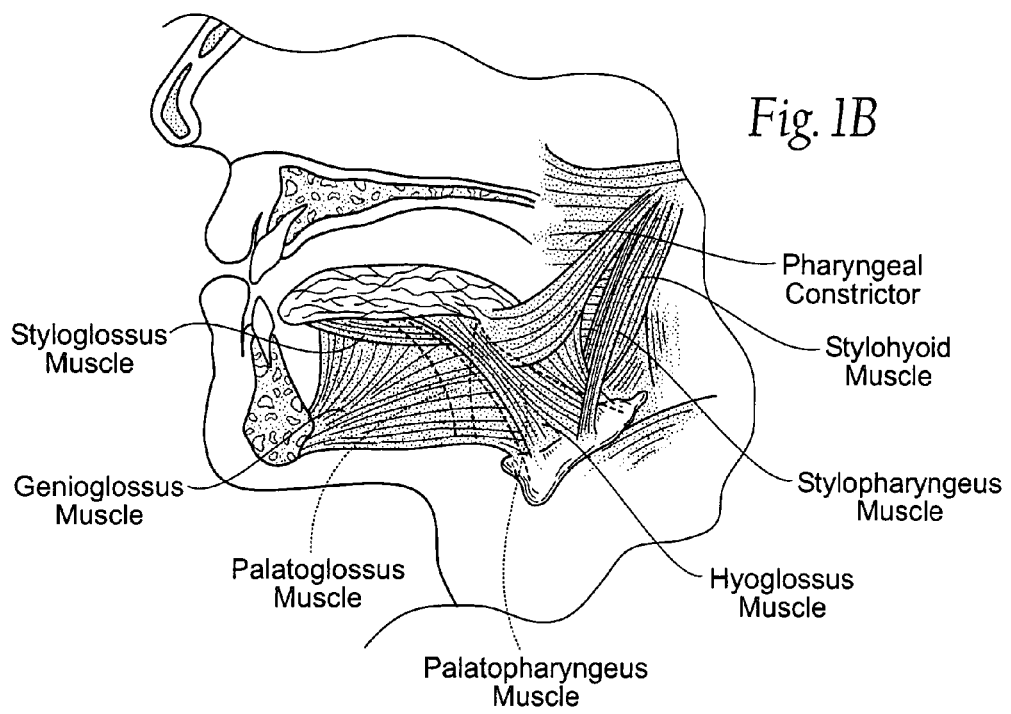
FIG. 1B is an anatomical sagittal view of the muscles of the upper respiratory tract.
Figure 1C:
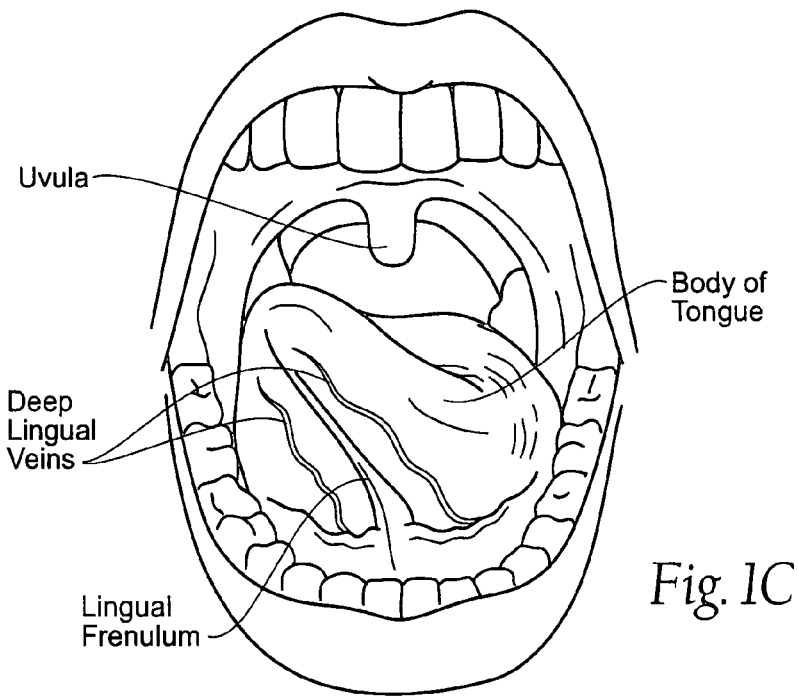
FIG. 1C is an anatomic anterior view of an oral cavity, with the body of the tongue elevated to show the inferior side of the tongue and the floor of the mouth.
Figure 1D:
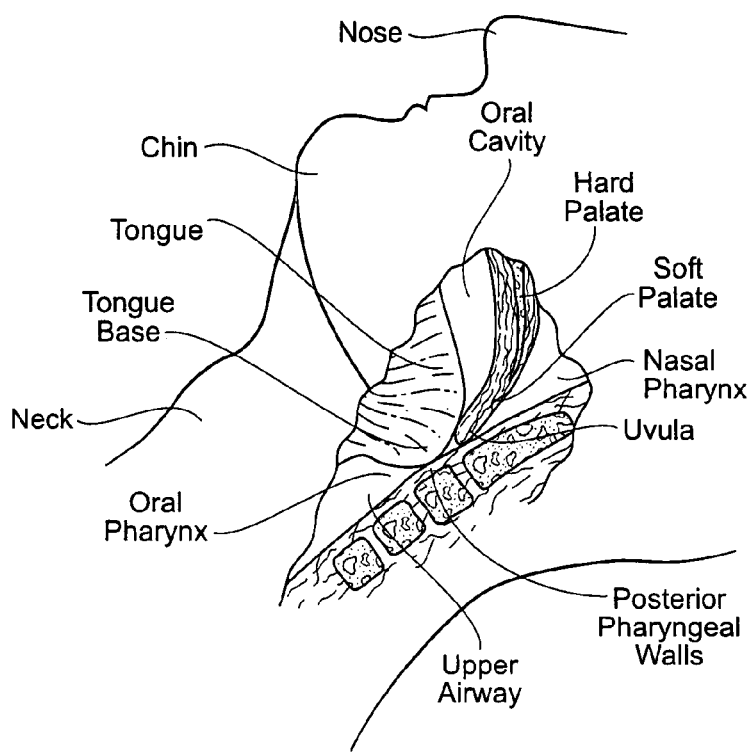
FIG. 1D is an anatomical side view, with sections partly broken away and in section, of a human suffering from one form of sleep apnea involving the tongue and the soft palate, showing how the tongue base, the soft palate, and the uvula lean against the pharyngeal wall, effectively closing off the airway, resulting in an apneic event.
Figure 2A:
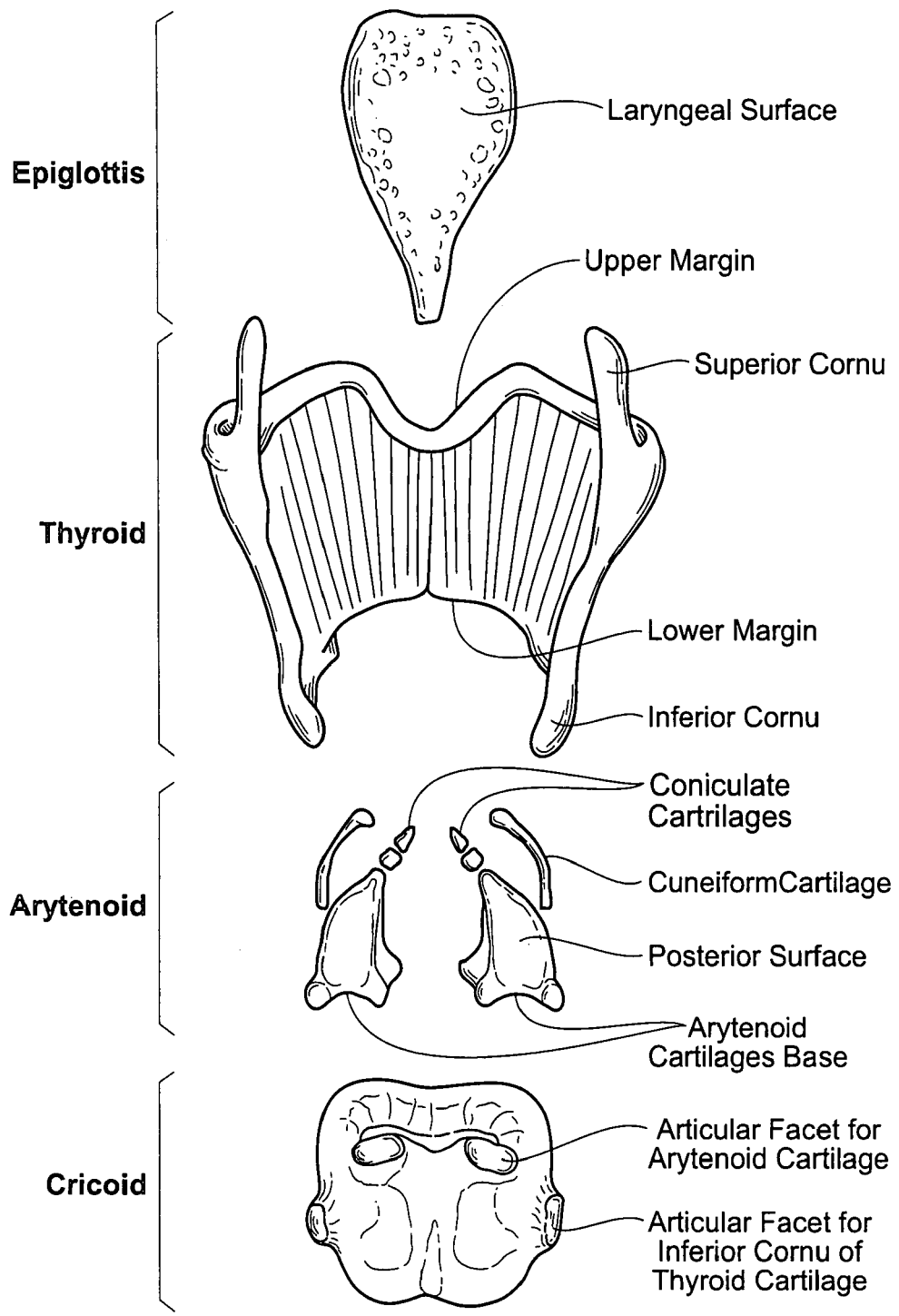
FIGS. 2A and 2B are anatomic views of the larynx.
Figure 2B:
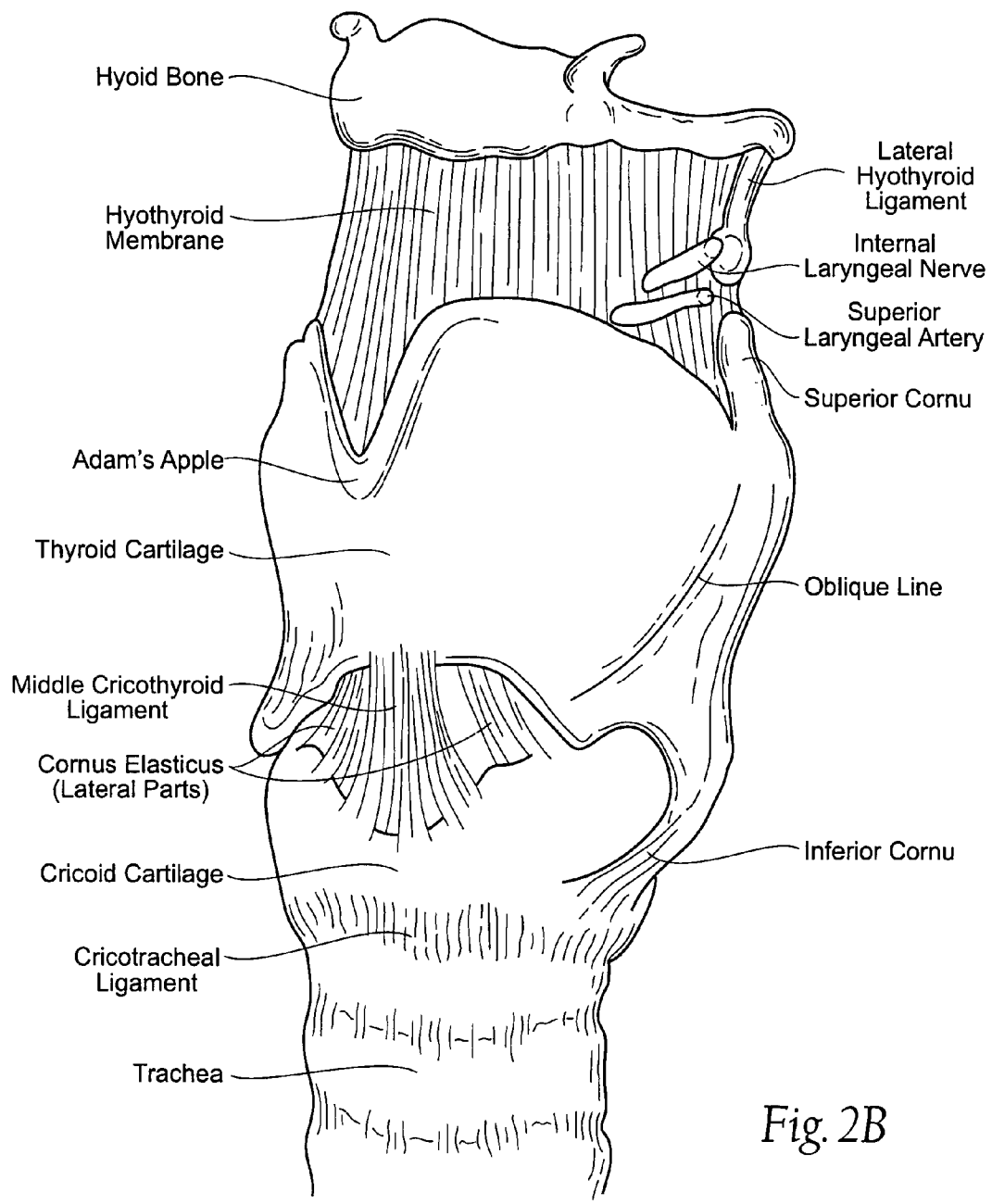
Figure 3A:
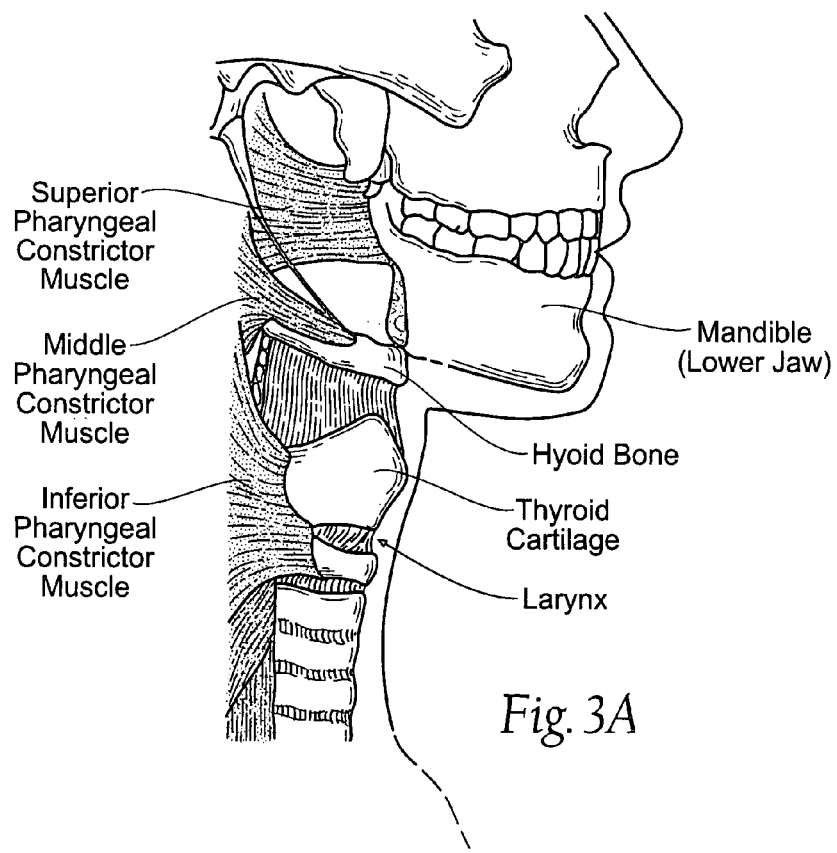
FIGS. 3A to 3D are anatomic views of the muscles attached to the hyoid bone.
Figure 3B:
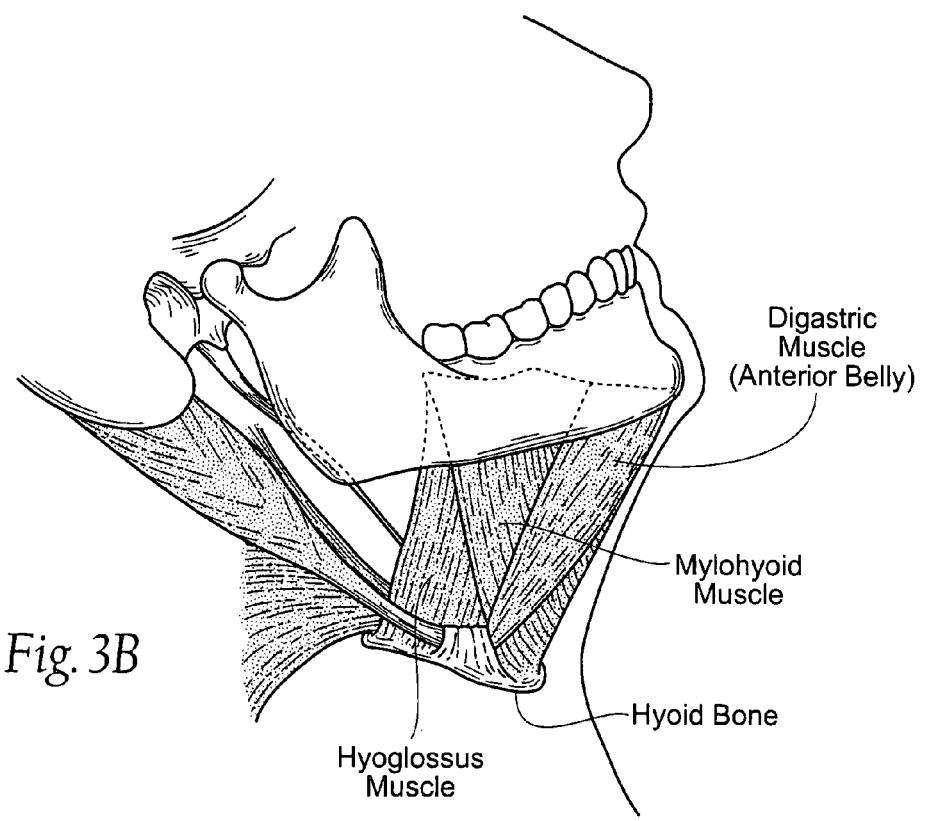
Figure 3C:
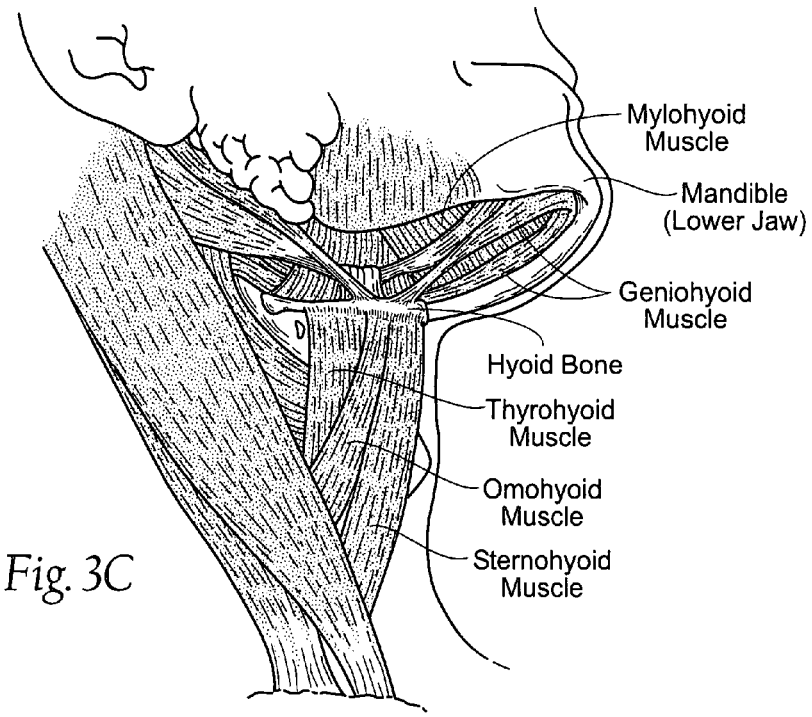
Figure 3D:
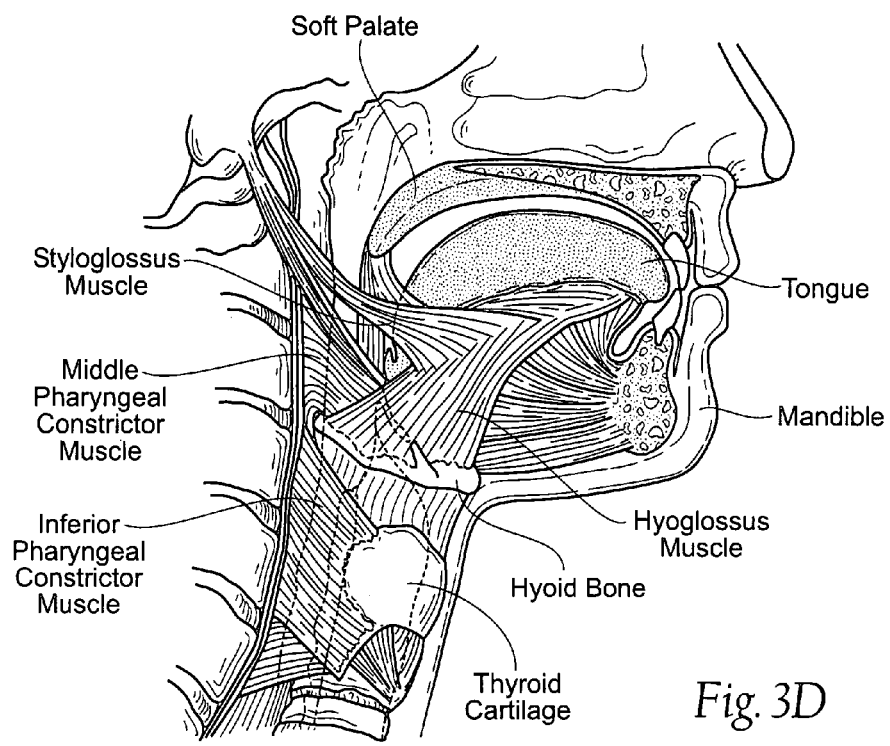

FIG. 1A is a sagittal cross section view of the upper airway system in a normal patient, showing the nasal and oral cavities, tongue, hard palate, soft palate, oropharynx, chin and neck. FIG. 1B shows a side view of a patient suffering from one form of sleep apnea involving the tongue and palate. As shown in FIG. 1B, the tongue base, the soft palate, and the uvula lean against the pharyngeal wall, effectively closing off the airway. An apneic attack can occur as a result.

II. The Treatment of Sleep Apnea

As described above, sleep apnea occurs when the airway becomes obstructed. Obstruction of the airway can be caused when muscles in at least a portion of the upper respiratory system lose tone and allow the airway to become obstructed. The present invention contemplates inserting various devices into various tissues of the upper respiratory system to reshape, relocate, or tension the surrounding tissue.

Figure 4A:
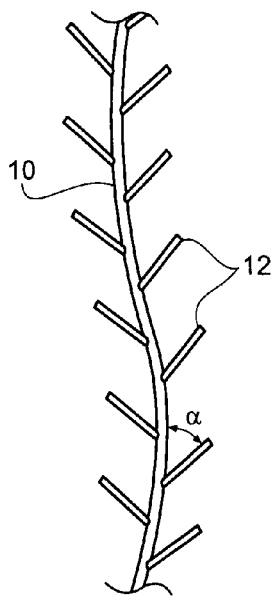
FIG. 4A is an illustrative embodiment of an elongated body sized and configured for implantation in a desired orientation in a tissue region in an airway, having an array of projections that are configured to engage tissue and resist a reorientation of the body within the tissue region out of the desired orientation.

A representative device 10 for treating sleep apnea is shown in FIG. 4A. As shown in FIG. 4A, the treatment device 10 takes the form of an elongated body that is sized and configured for implantation in a desired orientation in a tissue region. Although the body 10 may have any cross-sectional shape, in the illustrated embodiment, the body 10 has a generally circular cross-section. The elongated body 10 may be flexible to facilitate implantation of the body 10 in a targeted tissue region of an individual and thereafter conform to the orientation desired, which will depend upon the morphology of the tissue region and the particular treatment objectives. The elongated body 10 is also desirably generally non-elastic and/or otherwise has the mechanical resilience or strength capable of holding a tension, which will be in shorthand called "tension-able." The elongated body 10 can be made of a threadlike inert plastic or metal material, e.g., nylon, polypropylene, or stainless steel. One or more elongated bodies 10 can be implanted at a selected tissue region, depending upon the treatment objectives.

An array or plurality of projections 12 extend from the elongated body 10. As shown in FIG. 4A, the projections 12 extend radially outward at an acute angle α relative to the longitudinal axis of the body 10. The projections 12 are sized and configured to engage tissue and anchor the body 10 within a tissue region. By their design, the projections allow the elongated body 10 or a section of the elongated body 10 to move more easily through tissue in one direction than the other.

The projections 12 are desirably resiliently coupled to the body 10 in a normally biased outward extending condition. In this arrangement, the projections 12 can be folded back upon the body 10 by application of force, and resilient return to the normally biased outward extending condition when the force is removed. The projections 12 themselves can also be flexible.

Figure 4B:
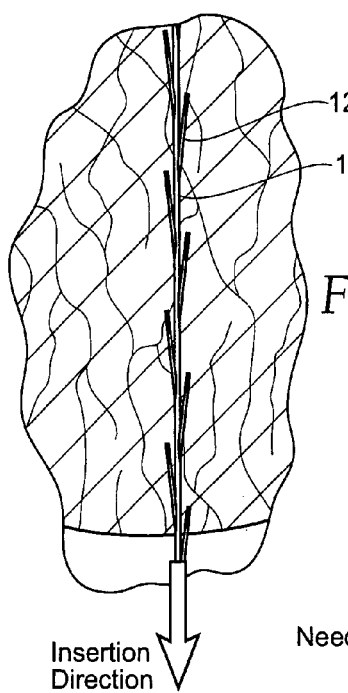
FIG. 4B is a view of the elongated body shown in FIG. 4A being implanted in a tissue region, showing the projections resiliently yielding by flexing inward against the body when the body is inserted through tissue in the intended implantation direction.

In the illustrated embodiment (see FIGS. 4A and 4B), the projections 12 extend from the body 10 in a direction opposite the direction in which the body 10 is intended to be inserted into a tissue region during implantation (shown by the insertion arrow in FIG. 4B). In this manner (as FIG. 4B shows), the projections 12 are capable of yielding by flexing inward against the body 10 when the body 10 is pulled through tissue in the intended implantation direction.

Figure 4C:
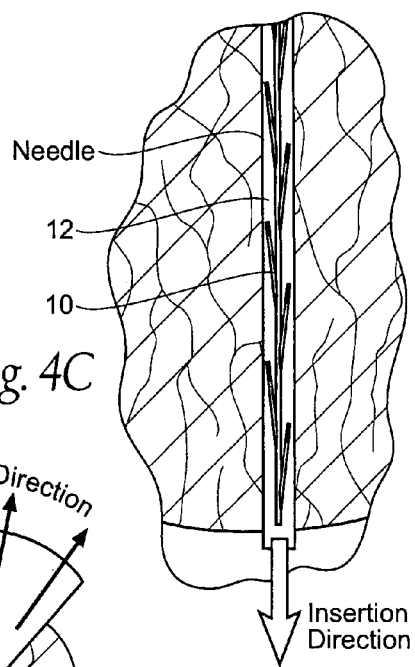
FIG. 4C is a view of the elongated body shown in FIG. 4A being implanted in a tissue region, showing the projections resiliently yielding by flexing inward against the body when the body is inserted through an implantation tool in the intended implantation direction.

Alternatively (as shown in FIG. 4C), the body 10 can be implanted through a guide tube or needle. In this arrangement, the projections 12 are capable of flexing inward against the body 10 when carried within the guide tube, and extending outward to engage tissue when the guide tube or needle is withdrawn (as FIG. 4D shows).

Figure 4D:
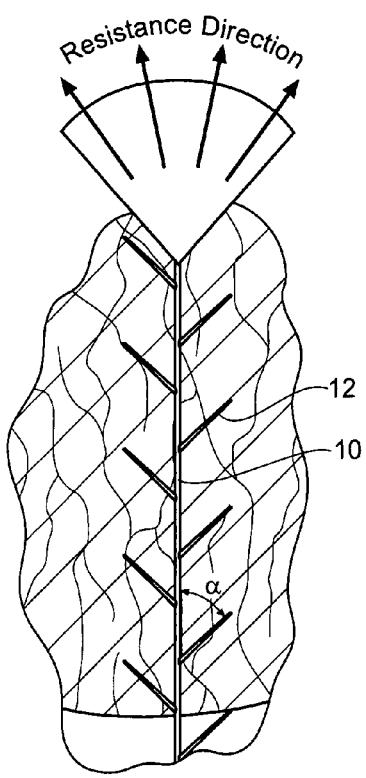
FIG. 4D is a view of the elongated body shown in FIG. 4A after implantation in a tissue region, showing the resilient projections extending outward to engage tissue and serve to resist movement of the body in tissue in a direction that is different than the insertion direction.

Regardless of the manner of implantation, after implantation of the body 12, the projections 12 will engage tissue and serve to resist movement of the body 10 in tissue in a direction that is different than the insertion direction (as shown by the resistance arrow in FIG. 4D). As shown in FIG. 4D, the resistance direction can lie in a range of directions angularly displaced about a direction directly opposite to the insertion direction.

Figure 4E:
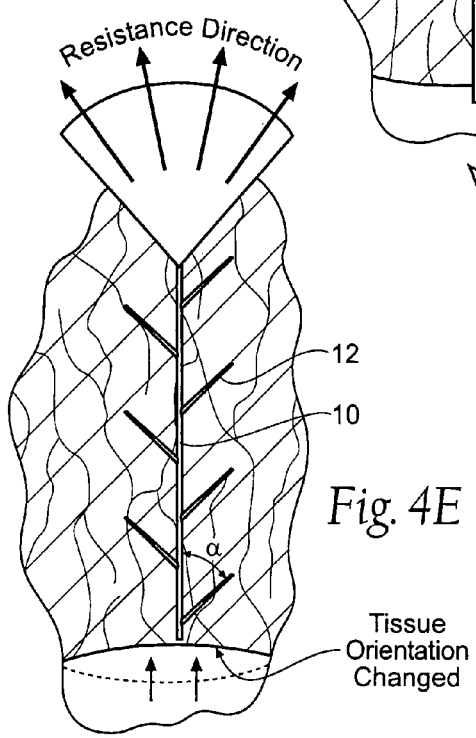
FIG. 4E is a view of the elongated body shown in FIG. 4A after implantation in a tissue region, showing the resilient projections extending outward to engage tissue and serve to resist movement of the body in tissue in a direction that is different than the insertion direction, which movement applies tension to the elongated body that affects a change in the shape or orientation of the tissue region in which the elongated body is implanted.

As shown in FIG. 4E, due to the orientation of the projections 12, pulling the elongated body 10 either during or after implantation in a direction that lies within the range of resistance directions, applies tension to the elongated body 10 and can affect a change in the shape or orientation of the tissue region in which the elongated body 10 is implanted.

In use, the elongated body 10 is implanted in a desired orientation in a tissue region. The desired orientation is governed by the location of the tissue region and the treatment objectives, e.g., a desired shape or bias that is to be imparted to the tissue region, and/or the maintenance of a desired orientation of the tissue region relative to another tissue region, e.g., to keep an airway patent. The array of projections 12 flex or otherwise yield to accommodate the implantation of the body 10 in the desired orientation. The desired orientation can include the selective application of tension to the elongated body 12 during its implantation, to affect a desired change in shape, orientation, and/or other physiologic characteristic within the tissue region.

During and after implantation of the body 10 in the desired orientation, the projections 12 serve to engage tissue, resisting a reorientation of the body 10 within the tissue region out of the desired orientation. When the orientation includes applying a tension to the body 10 during implantation, the projections 12 serve to maintain the tension, so that the tissue region itself is maintained in a desired orientation by the resistance that projections 12 impart.

A. Implantation within a Soft Palate

Figure 5A:
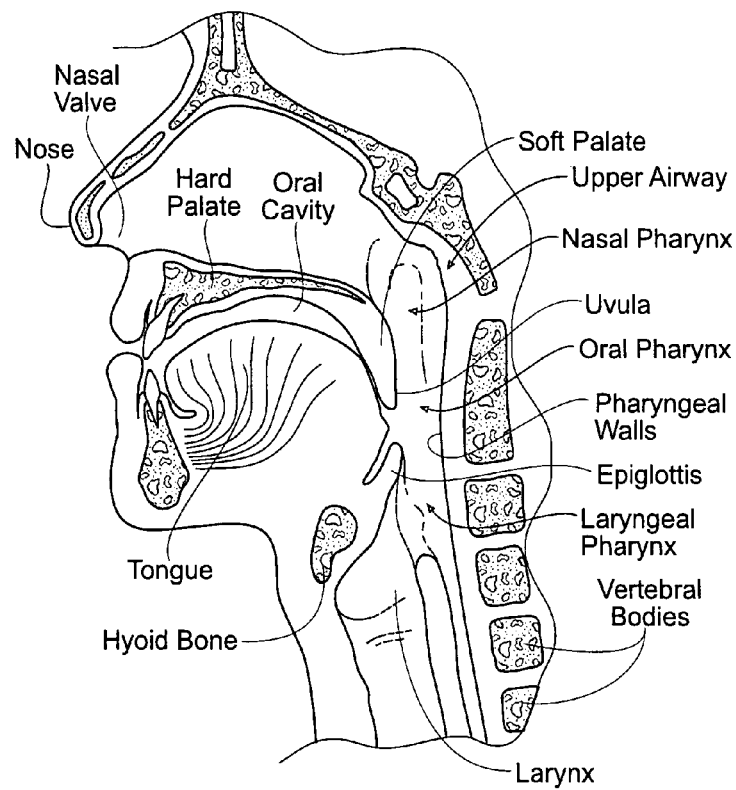
FIGS. 5A and 5B show a method of treating sleep apnea in the soft palate.

Obstructive sleep apnea can arise when tissue of the soft palate becomes "floppy." As shown in FIG. 5A, the floppy tissue of the soft palate may collapse upon the back of the tongue or other airway structures and thereby obstruct the airway. It is therefore desirable to tension and/or reposition the tissue of the soft palate to reduce or eliminate this obstruction of the airway.

Figure 5B:
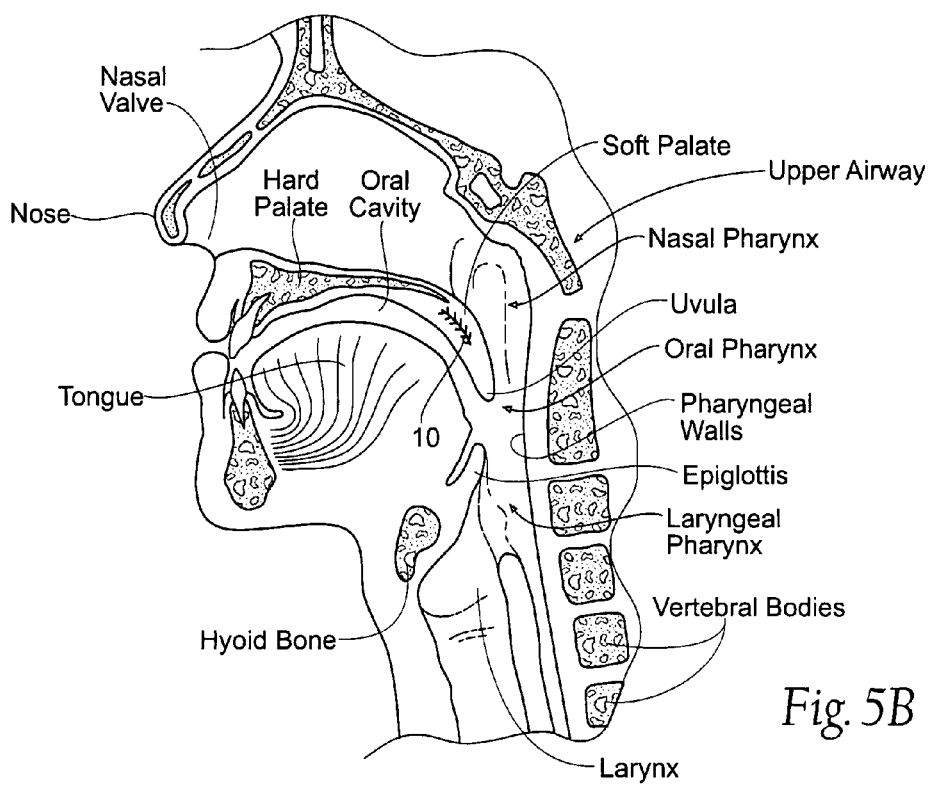

The treatment device 10 described above can be used to either tension and/or reposition the tissue of the soft palate to reduce the obstruction of the airway, as shown in FIG. 5B. In this representative embodiment, one or more of the elongated bodies 10 are implanted in a desired orientation in a tissue region of the soft palate. The desired orientation in this embodiment is governed by the treatment objective of maintaining the soft palate in a desired posterior and/or superior orientation away from the back of the tongue and other airway structures. The body 10 is implanted in an orientation and with a selective tension which shapes the soft palate in this desired orientation (shown in FIG. 5B), away from the back of the tongue and other airway structures.

In this arrangement, the projections 12 are oriented relative to the body 10 to flex or otherwise yield to accommodate the implantation of the body 10 in the desired orientation within the soft palate. After implantation, the projections 12 extend outward at the angle α from the body 10 and serve to engage tissue and resist a reorientation of the body 10 within the tissue region of the soft palate out of the desired orientation, to thereby resist collapse of the soft palate in an anterior and/or inferior direction, i.e., toward the base of the tongue.

B. Implantation within an Uvula

Figure 6A:
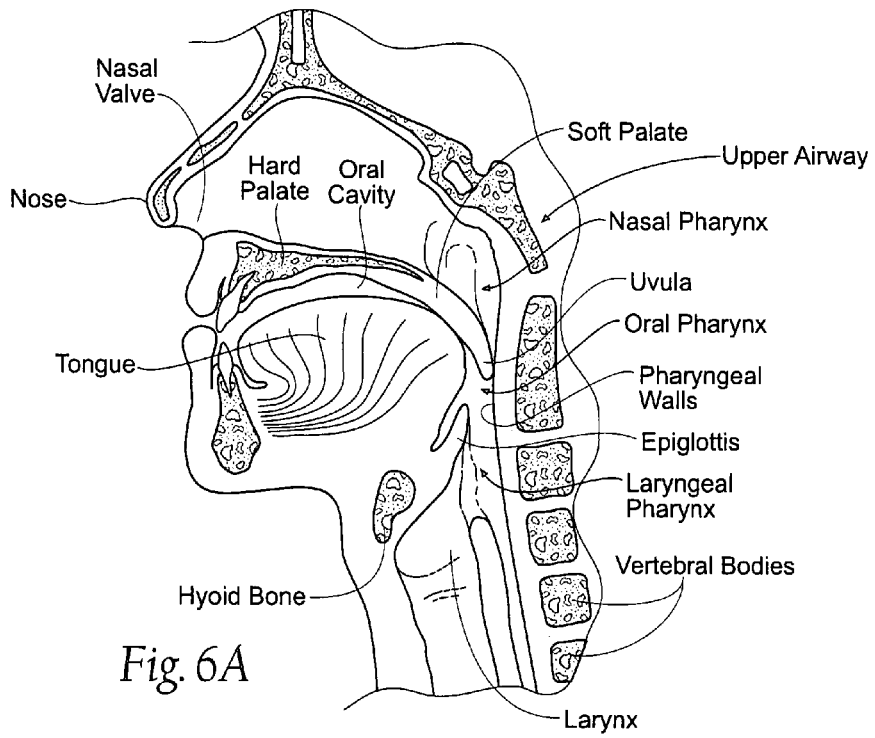
FIGS. 6A and 6B show a method of treating sleep apnea in the uvula.

Obstructive sleep apnea can also arise when the uvula becomes "floppy" and/or misshapen, as shown in FIG. 6A. If the uvula becomes floppy, it can become positioned in a posterior direction, collapsing against the back of the tongue and/or the pharyngeal wall, and obstruct the airway as shown in FIG. 6A. It is therefore desirable to either tension and/or reposition the uvula in an anterior direction to reduce obstruction of the airway.

Figure 6B:
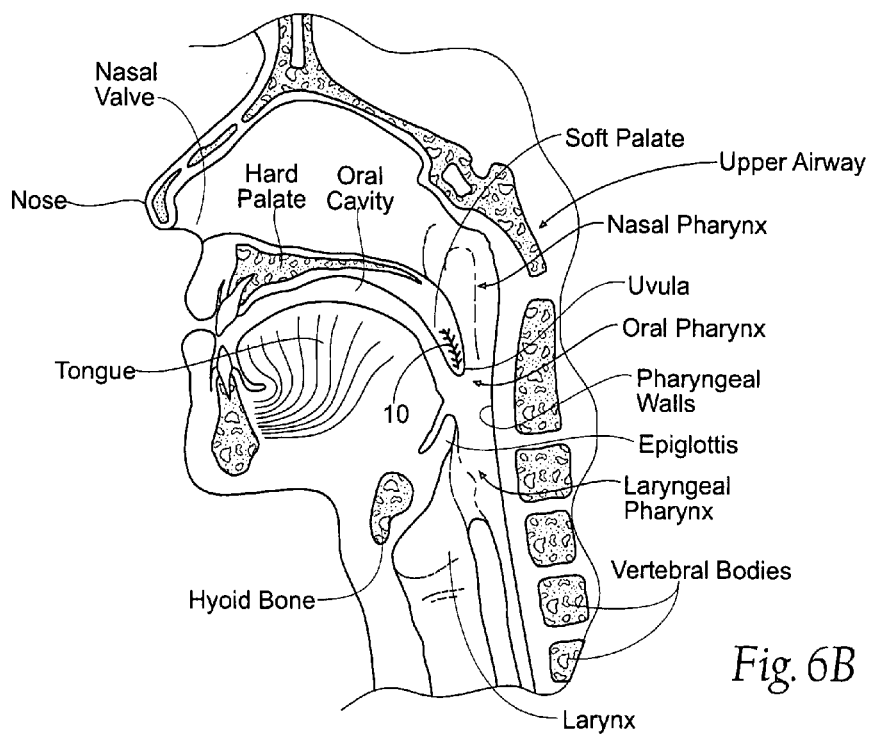

The treatment device 10 described above can be used to tension and/or reposition the uvula to reduce obstruction of the airway as shown in FIG. 6B. In this representative embodiment, one or more of the elongated bodies 10 are implanted in a desired orientation in a tissue region of the uvula. The desired orientation in this embodiment is governed by the treatment objective of maintaining the uvula in a desired anterior and/or superior orientation lifted away from the back of the tongue and the pharyngeal wall. The body 10 is implanted in an orientation and with a selective tension which shapes or urges the uvula in this desired orientation (shown in FIG. 6B), away from the back of the tongue and the pharyngeal wall.

In this arrangement, the projections 12 are oriented relative to the body 10 to flex or otherwise yield to accommodate the implantation of the body 10 in the desired orientation within the uvula. After implantation, the projections 12 extend outward at the angle α from the body 10 and serve to engage tissue and resist a reorientation of the body 10 within the tissue region of the uvula out of the desired orientation, to thereby resist collapse of the uvula toward the base of the tongue and/or against the pharyngeal wall.

C. Implantation within a Tongue

Figure 7A:
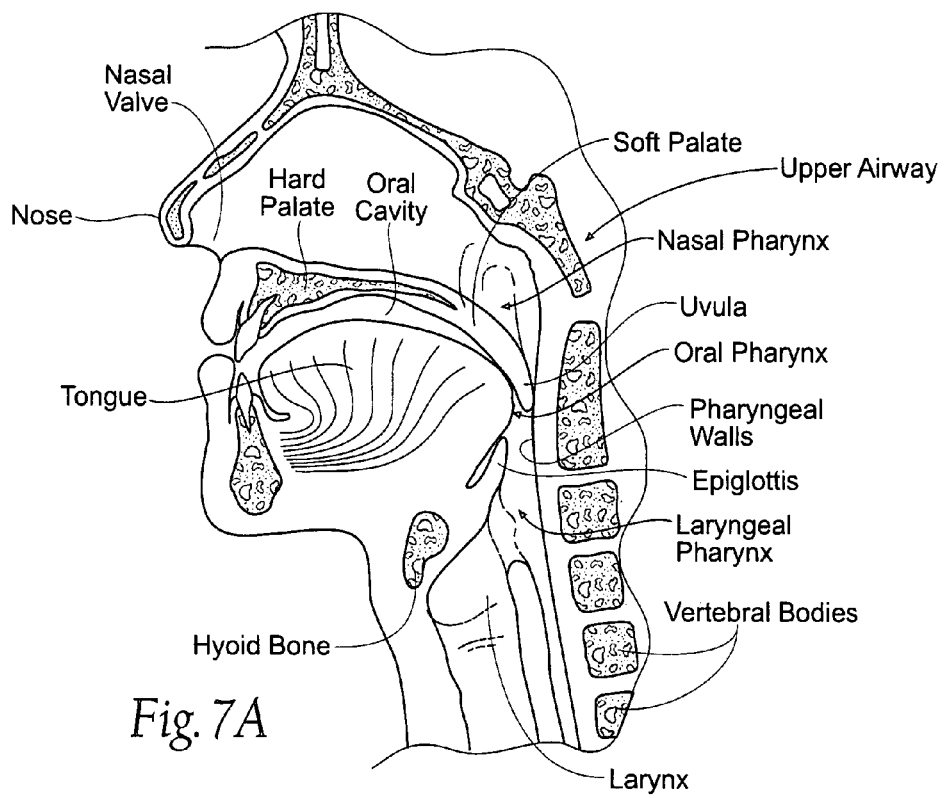
FIGS. 7A and 7B show a method of treating sleep apnea in the tongue.

Obstructive sleep apnea can also arise when the tongue muscles lose tone, causing the base of the tongue to collapse in a posterior direction against the uvula and/or pharyngeal wall, and thereby obstruct the airway, as shown in FIG. 7A. It is therefore desirable to either tension the muscles in the tongue, or otherwise reposition the tongue to reduce obstruction of the airway.

Figure 7B:
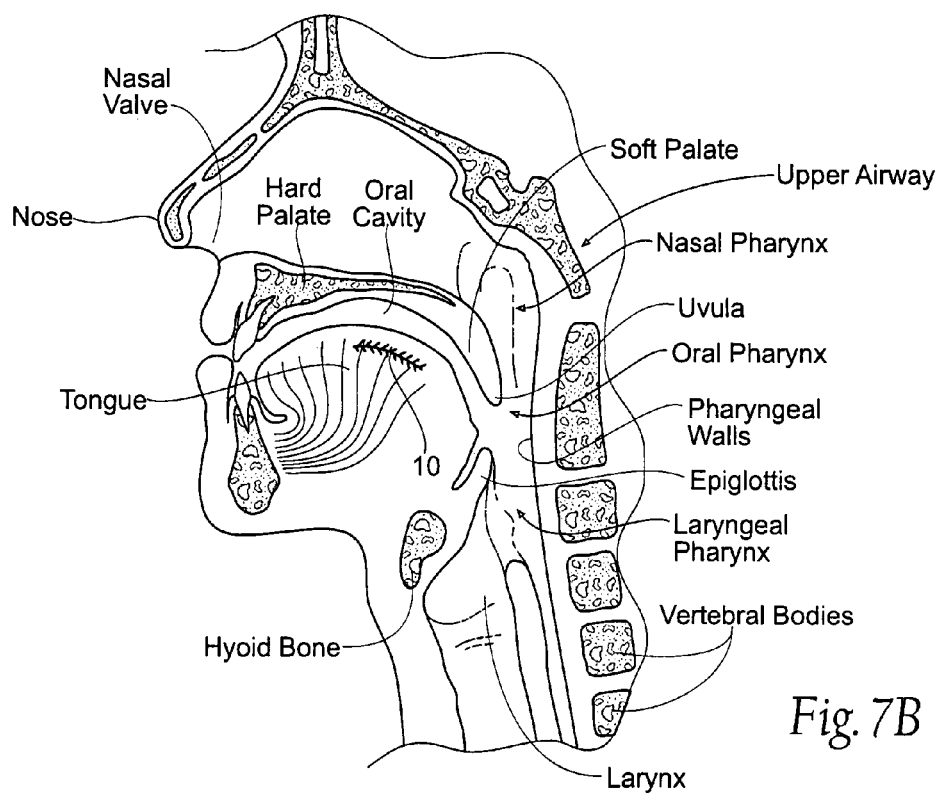

The treatment device 10 described above can be used to tighten the muscles in the tongue as shown in FIG. 7B. In this representative embodiment, one or more of the elongated bodies 10 are implanted in a desired orientation in a tissue region of the tongue. The desired orientation in this embodiment is governed by the treatment objective of urging or maintaining the tongue in a desired anterior orientation away from the uvula and/or pharyngeal wall. The body 10 is implanted in an orientation and with a selective tension which urges the tongue in an anterior direction (shown in FIG. 7B), away from the uvula and/or pharyngeal wall.

In this arrangement, the projections 12 are oriented relative to the body 10 to flex or otherwise yield to accommodate the implantation of the body 10 in the desired orientation within the tongue. After implantation, the projections 12 extend outward at the angle α from the body 10 and serve to engage tissue and resist a reorientation of the body 10 within the tissue region of the tongue out of the desired orientation, to thereby resist posterior collapse of the tongue against the uvula and/or the pharyngeal wall.

D. Implantation within an Epiglottis

Figure 8A:
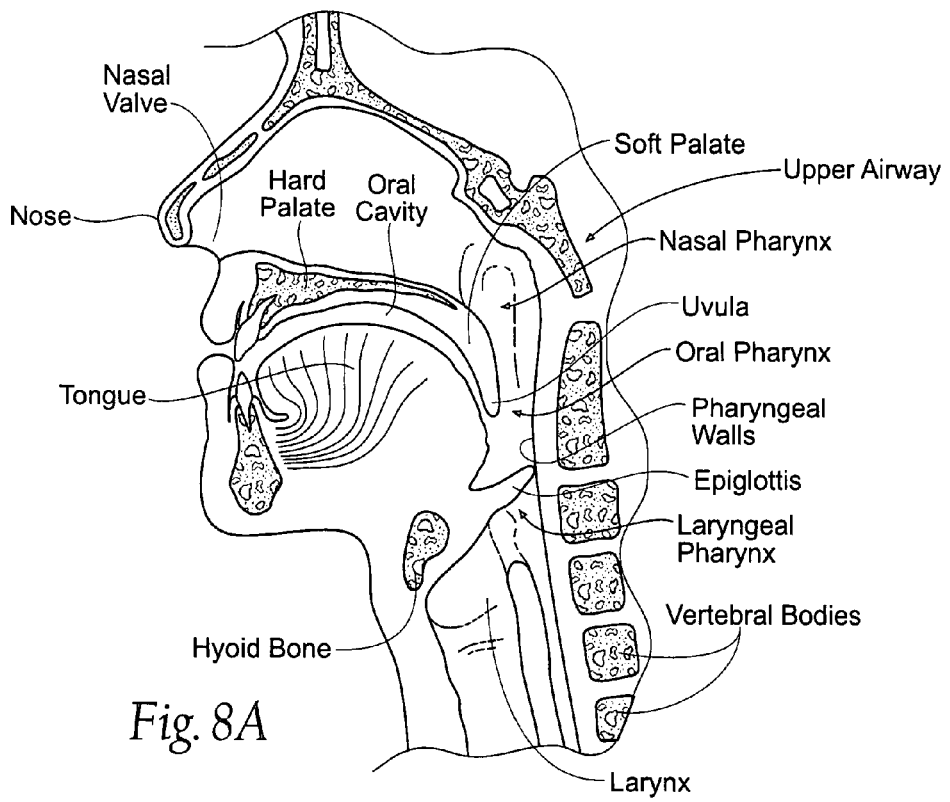
FIGS. 8A and 8B show a method of treating sleep apnea in the epiglottis.

Another source of obstructive sleep apnea includes abnormalities of the epiglottis, which close off or restrict the airway, as shown in FIG. 8A. For example, the epiglottis may prolapse and fold down to close off the airway. It is also possible that the epiglottis may be misshapen and therefore restrict the airway. The epiglottis may also lose muscle tone and become "floppy." A floppy epiglottis can restrict the airway. It is therefore desirable to either tension or reposition the epiglottis to reduce obstruction of the airway.

Figure 8B:
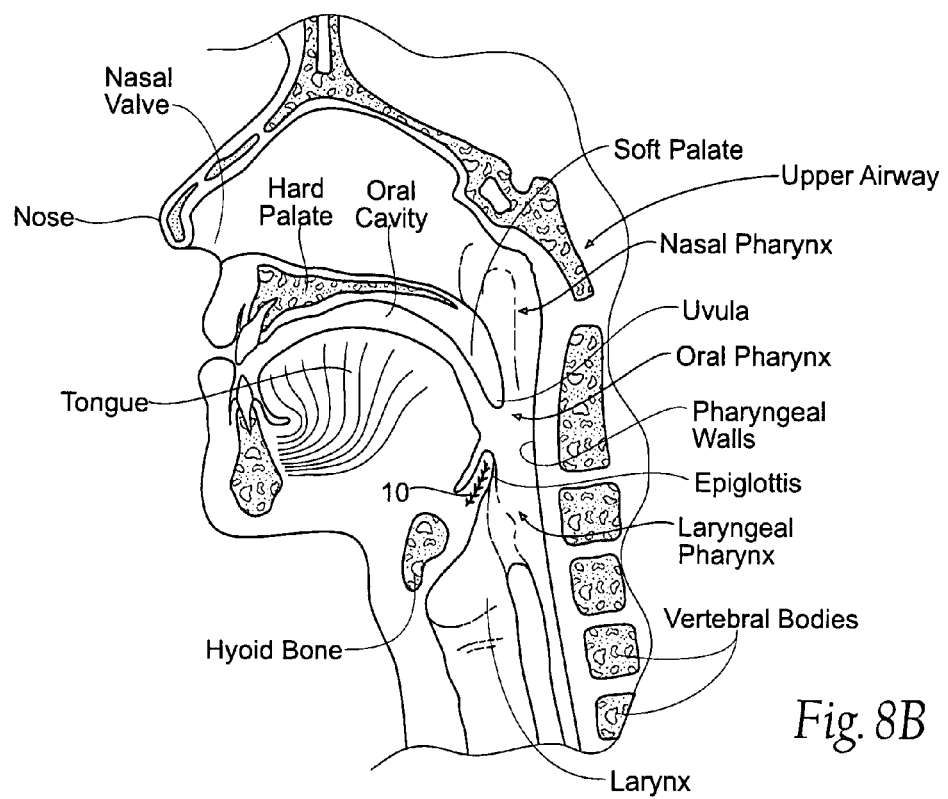

The treatment device 10 described above can be used to tension and/or reposition the epiglottis to reduce obstruction of the airway as shown in FIG. 8B. In this representative embodiment, one or more of the elongated bodies 10 are implanted in a desired orientation in a tissue region of the epiglottis. The desired orientation in this embodiment is governed by the treatment objective of maintaining or urging the epiglottis in a desired anterior orientation away from the pharyngeal wall. The body 10 is implanted in an orientation and with a selective tension which urges the epiglottis in an anterior direction (shown in FIG. 8B), away from the pharyngeal wall.

In this arrangement, the projections 12 are oriented relative to the body 10 to flex or otherwise yield to accommodate the implantation of the body 10 in the desired orientation within the epiglottis. After implantation, the projections 12 extend outward at the angle $\alpha$ from the body 10 and serve to engage tissue and resist a reorientation of the body 10 within the tissue region of the epiglottis out of the desired orientation, to thereby resist posterior collapse of the epiglottis against the pharyngeal wall.

E. Implantation in Muscles of the Upper Respiratory Tract

Figure 9A:
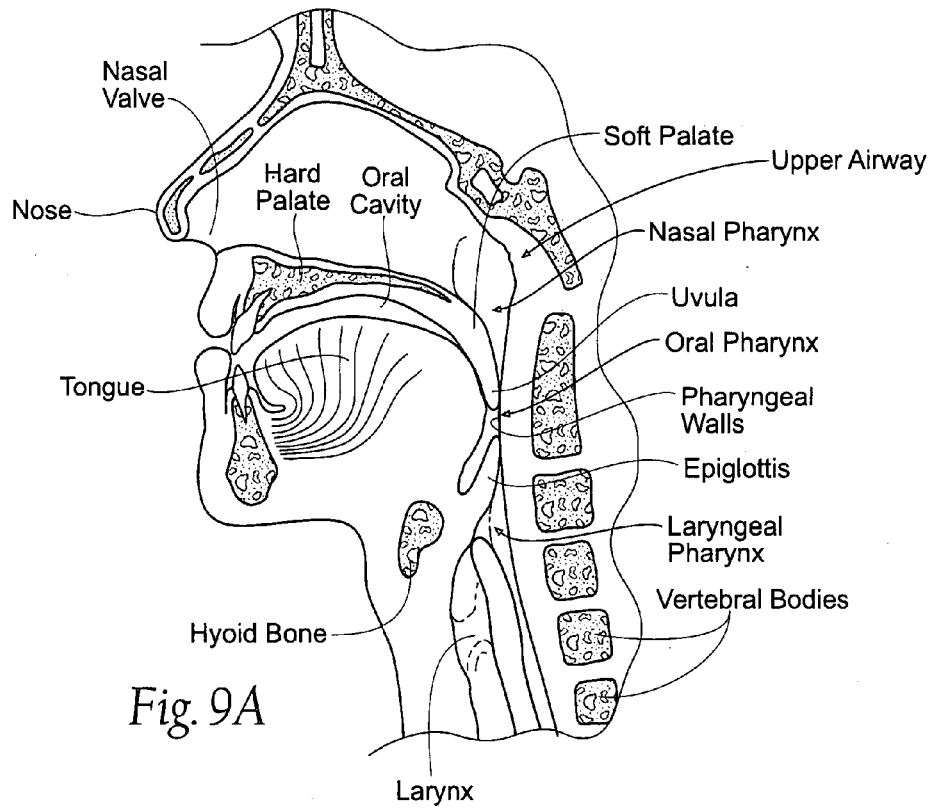
FIGS. 9A and 9B show a method of treating sleep apnea in the upper respiratory muscles.

Another source of obstructive sleep apnea is when the muscles in the pharyngeal wall along the upper respiratory tract lose tone. When the muscles relax, they may obstruct the airway as shown in FIG. 9A. This is particularly true in individuals with excessive relaxation of the upper respiratory muscles, or in individuals where the airway is already narrow. An individual's airway may naturally be narrow due to the individual's particular morphology, or may be narrow due to other factors such as obesity or other illness. It is therefore desirable to tension the muscles in the upper respiratory tract to reduce obstruction of the airway.

Figure 9B:
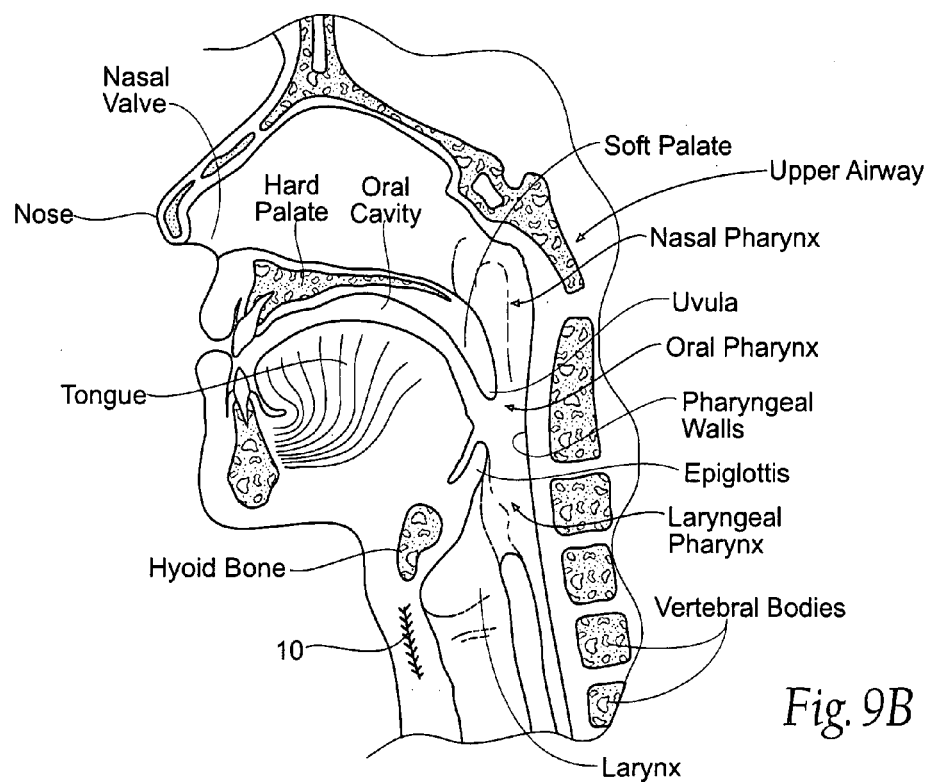

The treatment device 10 described above can be used to tighten the muscles of the upper respiratory tract, as shown in FIG. 9B. In this representative embodiment, one or more of the elongated bodies 10 are implanted in a desired orientation in a muscle region of the upper respiratory system. The desired orientation in this embodiment is governed by the treatment objective of maintaining or urging the muscle in a desired orientation, away from collapse against other structures along the airway. The body 10 is implanted in an orientation and with a selective tension which urges the muscle region in this orientation (shown in FIG. 9B), away from collapse against other structures along the airway.

In this arrangement, the projections 12 are oriented relative to the body 10 to flex or otherwise yield to accommodate the implantation of the body 10 in the desired orientation within the muscle region of the upper respiratory system. After implantation, the projections 12 extend outward at the angle $\alpha$ from the body 10 and serve to engage tissue and resist a reorientation of the body 10 within the muscle region of the upper respiratory system out of the desired orientation, to thereby resist collapse of the muscle region against other structures along the airway.

F. Use of the Treatment Device

The treatment device 10 can be used in the treatment of sleep apnea in at least one of three different ways.

First, the treatment device 10 may be used, by itself, to effectively treat sleep apnea. It is contemplated that the treatment device 10 could be utilized in many parts of the upper airway, including, but not limited to the uvula, the soft palate, the hard palate, the tongue, the muscles of the upper respiratory tract, or the epiglottis, as previously described.

Second, the treatment device 10 can provide temporary treatment of sleep apnea allowing the individual and the treating physician time to evaluate whether more invasive surgery intervention, e.g., uvulopalatoplasty (UPPP), may offer as results.

Third, the treatment device 10 can be used in conjunction with other types of sleep apnea treatment, such as the magnetic force systems disclosed in U.S. patent application Ser. No. 10/656,861, filed Sep. 6, 2003, and entitled "Magnetic Force Devices, Systems, and Methods for Resisting Tissue Collapse Within the Pharyngeal Conduit." Due to individual anatomical constraints, a system consisting of ferromagnetic structures may benefit from being supplemented by the use of the treatment device 10 to provide additional tension in specific upper respiratory tissue locations.

III. Representative Examples of the Treatment Device

A. Barbed Sutures

The treatment device 10 as described above can be constructed in various ways. In one representative embodiment, the treatment device 10 takes the form of a barbed suture 110, as shown in FIGS. 10A and 10B. The barbed suture 110 comprises an elongated body that is sized and configured for implantation in a desired orientation in a tissue region of an airway. The suture 100 can comprise a flexible threadlike plastic or metal material, such as nylon, polypropylene, or stainless steel, which is, desirably, essentially tension-able, as earlier defined.

The barbed suture 110 includes an array of projections or barbs 112. The projections 112 extend from the elongated suture body at the angle $\alpha$ and are sized and configured to engage tissue and anchor the elongated suture body in the tissue region. The array of projections or barbs 112 thereby resists a reorientation of the elongated suture body within the tissue region out of the desired orientation.

The projections or barbs 112 can be produced, for example, by cutting at a slant into the elongated suture body to form sharp projections that bend back. The projections or barbs 112 can run either in the same direction (i.e., unidirectionally) (as shown in FIG. 10A) or two different directions (i.e., bidirectionally) (as shown in FIG. 10B) from the elongated suture body midpoint. An un-barbed section can follow the barbed sections at both ends of the sutures 110.

Figure 11A:
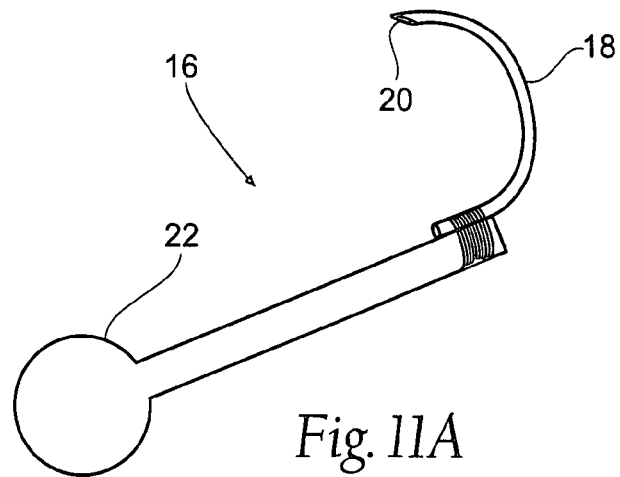
FIGS. 11A to 11E show an instrument and a method of inserting barbed sutures in the palate.

B. Representative Instrument and Method for Implanting a Barbed Suture in an Uvula As generally described above, one or more barbed sutures 110 can be implanted in a uvula 14. FIG. 11A shows a representative instrument 16 for use in inserting the barbed sutures 110. The instrument 16 comprises a hollow sharp needle 18 with a large enough bore 20 to pass a suture 110. The hollow sharp needle 18 may be attached to a handle 22. Preferably, the needle 18 has a gently curved shape, similar to the soft palate 24. The needle 18 includes a proximal end by the handle 22 and a distal end spaced from the handle.

Figure 11B:
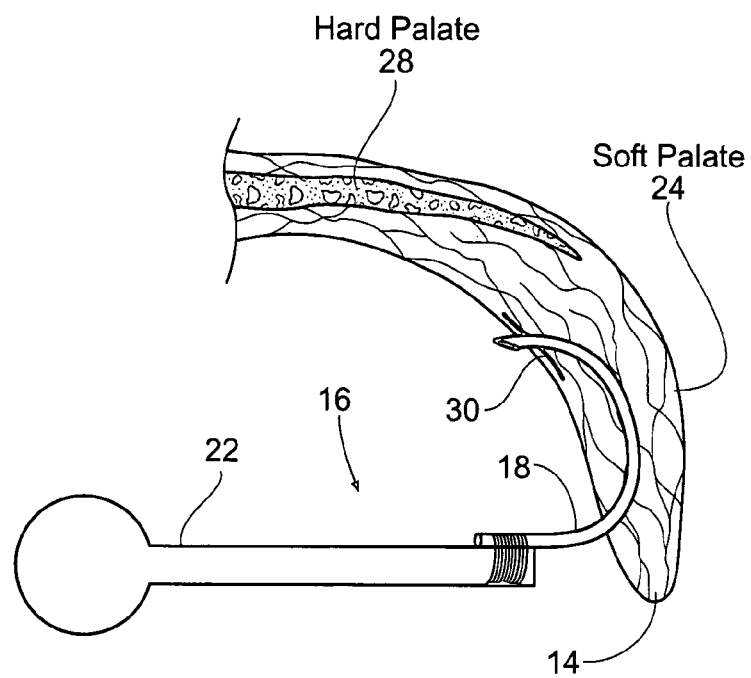
Figure 11C:
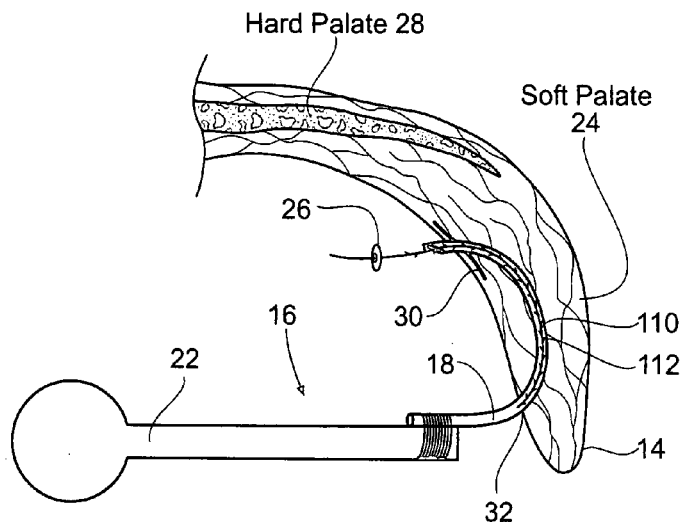

As shown in FIG. 11C, the suture 110 comprises a series of tissue grasping barbs 112, as previously described. The suture 110 also includes an adjustable, sliding toggle anchor 26 at one end (see FIG. 11C). The sliding toggle anchor 26 will be described in more detail below. As an alternative, a needle 18 may be suaged to the barbed suture 110, without a handle.

The implantation procedure can be performed under general or local anesthesia. As seen in FIG. 11B, with the individual's mouth open, the distal end of the needle 18 is placed submucosally into the soft palate 24, starting at the uvula 14, to penetrate into muscle tissue. The distal end of the needle 18 is then advanced to the soft and hard palate junction area. The distal end of the needle exits back into the oral cavity, as FIG.

11B shows. The tissue at the needle exit site in the vicinity of the hard/soft palate junction is firm fibromuscle.

Prior to the needle exiting the mucosa, a small transverse incision is made through the mucosa at the needle exit site to develop a small submucosal pocket 30 (which FIG. 11B shows).

Figure 11D:
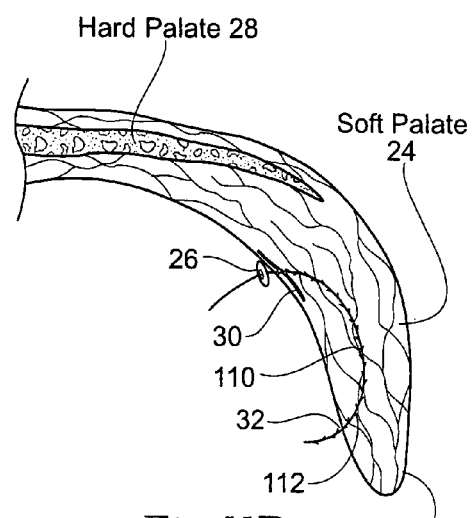

As seen in FIG. 11C, once the distal end of the needle 18 has exited the mucosa, the barbed suture 110 with an adjustable toggle end anchor 26 is fed retrograde through the distal end of the needle 18 (i.e., the suture end that does not carry the toggle anchor 26 being inserted into the distal end of the needle end first), exiting at the uvula entrance site 32 near the proximal end of the needle. As seen in FIG. 11D, the hollow needle 18 is then withdrawn, leaving the suture 110 in place in the soft palate 24. In this orientation of the suture body, the barbs 112 are oriented to engage tissue and resist movement of the suture body when the end of the suture 110 carrying the toggle anchor 26 is pulled.

Alternatively, a curved needle 18 suaged to the end of the barbed suture 110 could penetrate the palate 24 near the hard palate-soft palate junction, exit at the distal end of the uvula 14, and draw the barbed suture 110 into position behind it (not shown).

Regardless of the suture insertion method used, the portion of the suture 110 visible at the uvula 14 may then be trimmed. The end of the suture 110 carrying the toggle anchor 26 is pulled to pull the opposite end of the suture 110 antegrade, to bury the opposite end lined with barbs 112 in submucosal uvula tissue. This begins to place the suture body into tension, as the barbs 112 resist movement of the suture body in the pulling direction. The tension begins to lift and curve the uvula in anterior and superior directions.

The individual's mouth is then closed, leaving the toggle end of the suture 110 protruding out of the mouth. With the individual in a supine position, a flexible nasopharyngoscope is passed trans-nasally to view the retropalatal airway.

The toggle end of the suture 110 is pulled further in an anterior direction (antegrade in the palate), further engaging the barbs 112 and further placing the suture in the desired orientation within the uvula. Placing the suture into the desired orientation also applies more localized tension in the tissue region. In response, the uvula and, with it, the soft palate in general, move toward the desired forward-curved orientation to attain an appropriate posterior palatal airway space, as shown in FIG. 6B. The orientation of the airway space continues to be viewed by nasopharyngoscope as tension is selectively applied by pulling on the toggle end of the suture 110. If the patient is awake, this is done at end expiration, and verified with Mueller maneuvers. If asleep under anesthesia or sedation, palate flaccidity and obstruction will be evident.

Figure 11E:
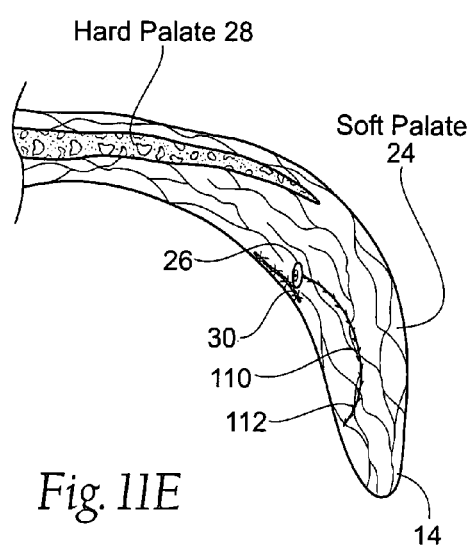

The mouth is then reopened, and as shown in FIG. 11E, the toggle 26 is slid down the suture and cinched down on the suture 110 at the previously made hard/soft palate submucosal junction pocket 30.

The procedure is finalized by closing the submucosal junction pocket 30. The submucosal junction pocket 30 may be closed using any medically accepted devices and methods.

The implantation procedure may consist of placing one or more barbed sutures 110, depending on the clinical need. The number of barbed sutures 110 placed will be determined by the physician based on the individual patient morphology.

The implantation of an elongated body with projections, such as a barbed suture 110, makes possible a less morbid, less damaging and less invasive alternative to a surgical uvulopalatoplasty. The implantation of an elongated body with projections, such as a barbed suture 110, can also serve as an alternative to existing treatments for habitual snoring. When tensioning of the elongated body is done under sedated endoscopy, it has the capability of being a one-stage titratable suspension procedure. Presently available approaches (laser resection, radiofrequency stiffening, and Pillar implant stiffening) do not have that capability.

An elongated body with projections such as a barbed suture 110, can be removed under local anesthesia by freeing the submucosal toggle 26, localizing the uvula end of the suture 110, and pulling the suture body out retrograde, as will be described in more detail below.

C. Representative Instrument and Method of Implanting a Barbed Suture in the Tongue One or more barbed sutures 110 can be inserted in the tongue 34 to pull the tongue 34 anteriorly and retain a patent airway. The tongue base can be pulled anteriorly by use of barbed sutures 110 in various ways.

Figure 12A:
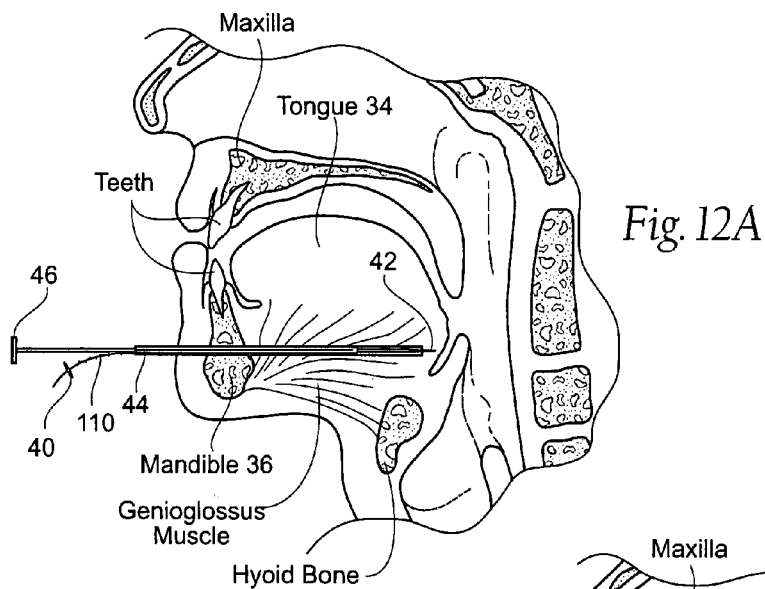
FIGS. 12A to 12E are anatomical sagittal views of a human upper respiratory system showing a method of inserting a barbed suture in the tongue.

In one representative embodiment (as shown in FIGS. 12A to 12E), an incision is made in the skin and a small hole is drilled in the mandible 36 at the attachment point for the genioglossus muscle 38 (see FIG. 12A). As seen in FIG. 12A, access to this drill hole in the bone can be made either at the front of the chin or intra-orally.

Figure 12B:
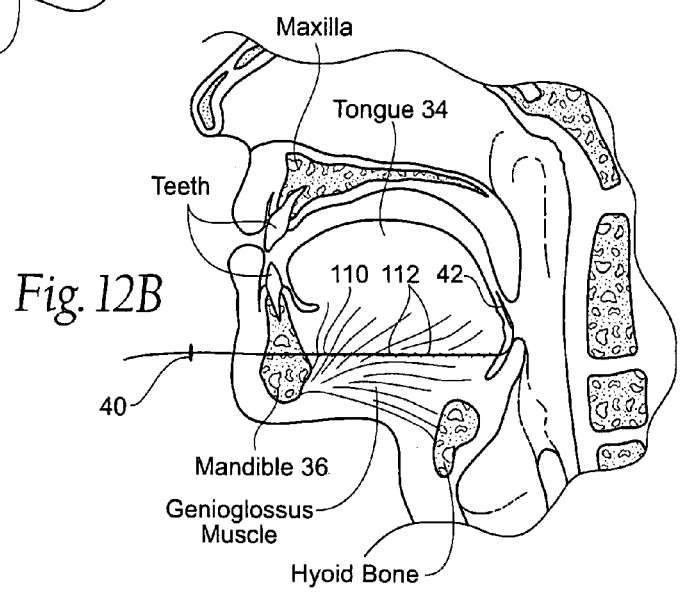

A length of either unidirectional or bidirectional barbed suture 110 with a stop or button 40 attached at one end is threaded through a needle 42. The button 40 is desirably sized so that it is too large to fit through the hole in the jaw. The needle 42 and suture 110 is inserted into an application shaft 44. The application shaft 44 is inserted into the hole in the jaw. Using a plunger 46, the needle is then pushed through the tongue 34 (as shown in FIG. 12A) and removed from the posterior portion of the tongue 34 (as shown in FIG. 12B). The needle is removed through the mouth. The plunger 46 and the application shaft 44 are then removed from the hole in the jaw, leaving the suture 110 behind within the tongue.

Figure 12C:
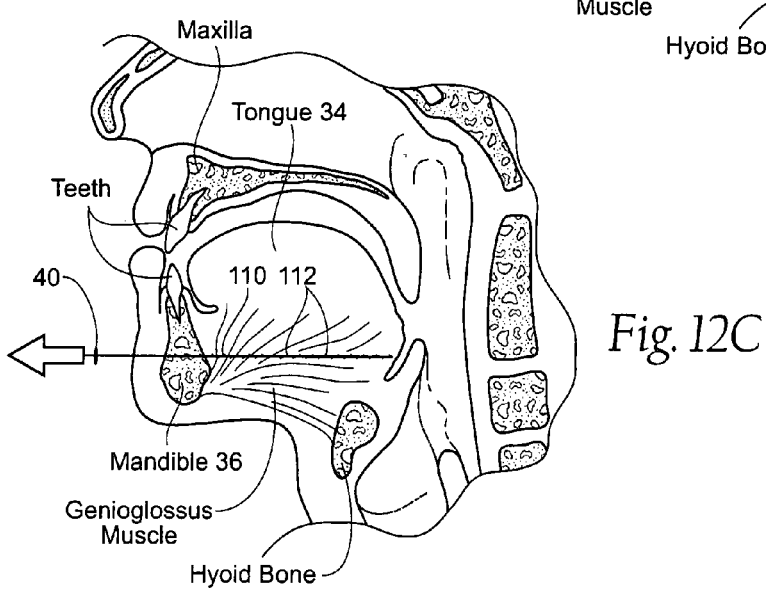
Figure 12D:
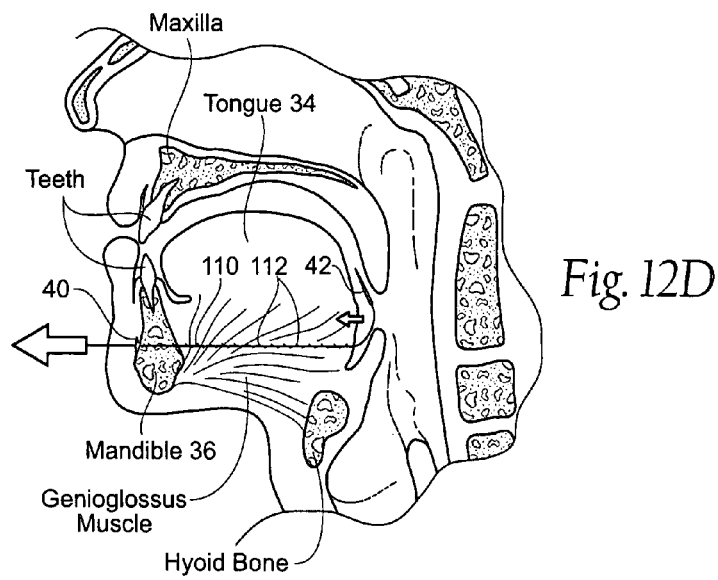

The suture 110 is then pulled in an anterior direction through the jaw (as shown in FIG. 12C). Because the barbs 112 are oriented to engage tissue and resist movement of the suture body in the pulling direction, the suture body is placed into tension within the tongue, pulling the posterior region of the tongue in an anterior direction. Securing the button 40 to the suture 110 in a position resting against the jaw bone or mandible 36 (see FIG. 12D) holds the tension. The tension holds the posterior region of the tongue in an anterior direction, resisting posterior movement in the direction of the airway. The tongue 34 is thereby positioned so that the suture barbs 112 hold it in a forward position, so as to open the airway.

Figure 12E:
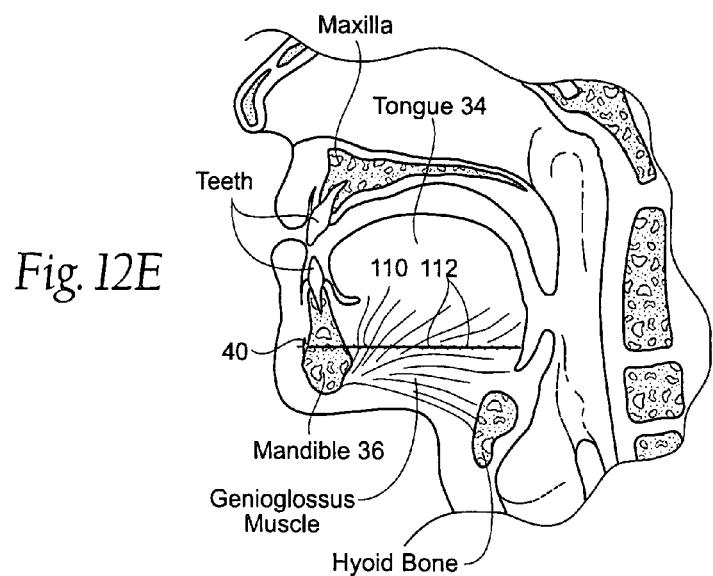

As seen in FIG. 12E the suture 110 is trimmed slightly below the surface of the tongue 34. The tissue is then closed over the button 40 to complete the procedure. Multiple sutures 110, possibly attached to the same button 40, could be advantageous. It is also contemplated that the needle 42 could be inserted through the jaw without the use of the application shaft 44 and plunger 46.

Figure 12F:
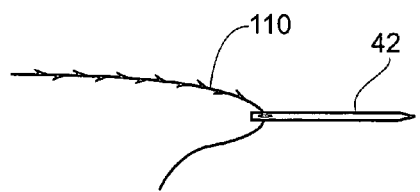
FIGS. 12F and 12G are illustrative embodiments of needles used to insert barbed sutures in the tongue.
Figure 12G:
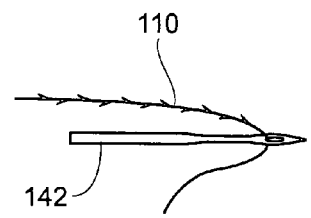

To aid in the removal of the needle 42, the needle 42 desirably is flexible, short and attached to a longer application shaft (FIG. 12F), or of a type used with sewing machines (FIG. 12G). A flexible needle 42 can be easily bent to facilitate pulling it out of the posterior part of the tongue 34. A short needle 42 would be removed from the application shaft and taken out through the mouth, while the application shaft would be withdrawn through the jaw hole. Alternatively, the sewing machine-style needle 142 would allow the suture 110 to be removed from the needle at the back of the tongue 34.

Figure 13A:
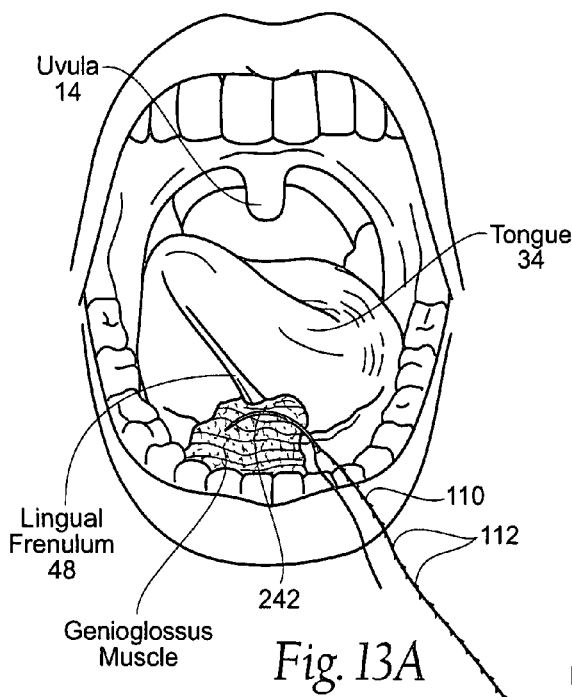
FIGS. 13A to 13D are anatomical views of the oral cavity showing an alternate method of inserting a barbed suture in the tongue.
Figure 13B:
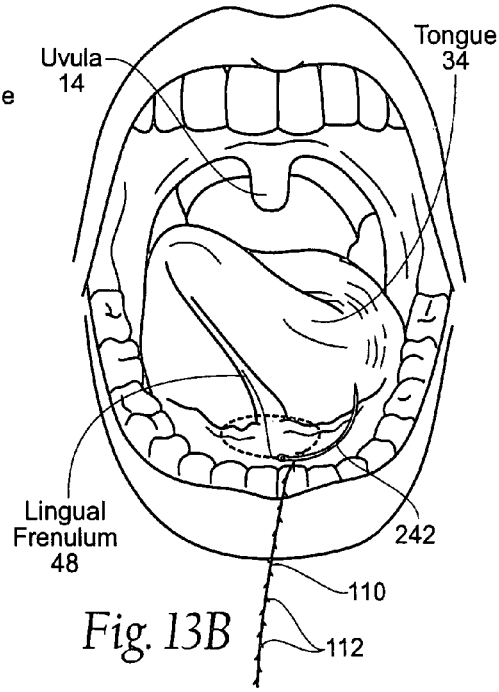
Figure 13C:
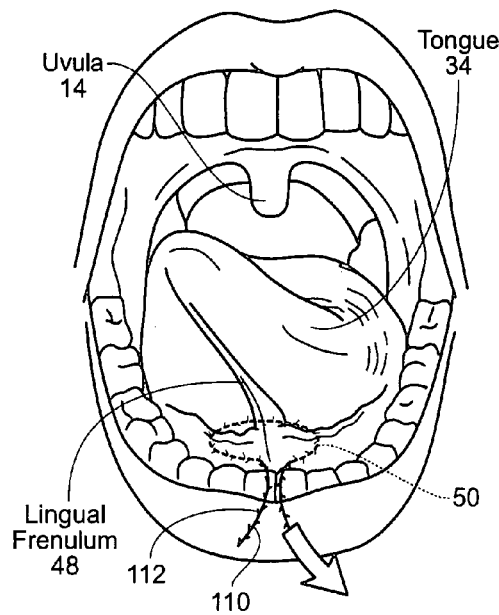
Figure 13D:
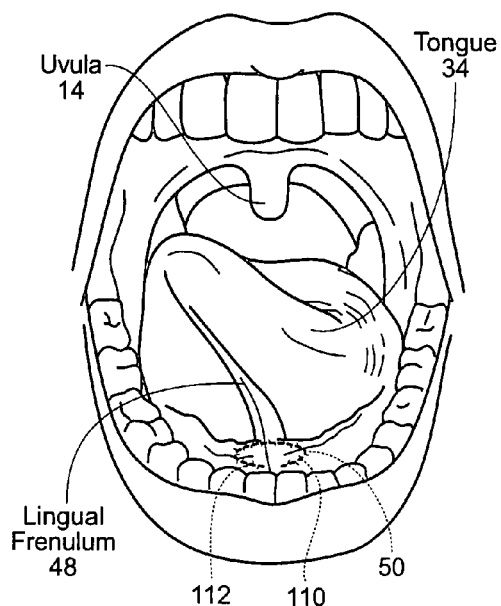

In another representative embodiment (as shown in FIGS. 13A and 13B), an incision is made with a curved needle 242 close to the lingual frenulum 48 at or near the inferior base of the tongue 34 and into extrinsic muscle (e.g., the genioglossus muscle) beneath the tongue. A barbed suture 110 threaded through the hole of the curved needle 242 follows the curvilinear path of the needle 242. As a result, the suture 242 is implanted in a curved or curvilinear orientation (a loop 50) in the extrinsic muscle at the inferior base of the tongue, as FIG. 13B shows. By pulling on the end of the suture 110 extending from the needle entrance site in a direction opposite to the direction of insertion (as shown in FIG. 13*c*), tension is applied to the suture, because the barbs 112 extend outward at an angle α to engage tissue and resist movement in this direction. The tension cinches the suture loop into a more tightly curved orientation, and the barbs 112 resist a reorientation of the suture out of this orientation. The tension tightens up the extrinsic muscle at the inferior base of the tongue. In response, the tongue 34 is moved anteriorly, as shown in FIG. 13D. More than one barbed suture 100 can be implanted in extrinsic muscle at or near the inferior base of the tongue in this manner.

In a different approach, one or more barbed sutures can be implanted with curved needle(s) through an incision under the chin on the inside edge of the mandible 36. In this arrangement, the curved needle 242 is directed through both the geniohyoid and genioglossus muscles, forming the loop 50. Cinching the looped barbed suture 110 in the manner just described will tighten up the genioglossus and the geniohyoid muscles, thereby moving the tongue 34 anteriorly.

One or more looped barbed sutures, implanted in extrinsic muscles at or near the inferior base of the tongue create an anterior tension in the tongue similar to genioglossal advancement, but without requiring attachment to a mandible. Barbed sutures in the geniohyoid muscle could affect a hyoid advancement, as will be discussed later.

D. Representative Instrument and Method of Implanting Barbed Sutures in the Palate and Uvula One or more barbed sutures 110 can be implanted in the palatal arch 52 to improve the tone of the palate 24, and reduce what is called a "floppy palate."

Figure 14A:
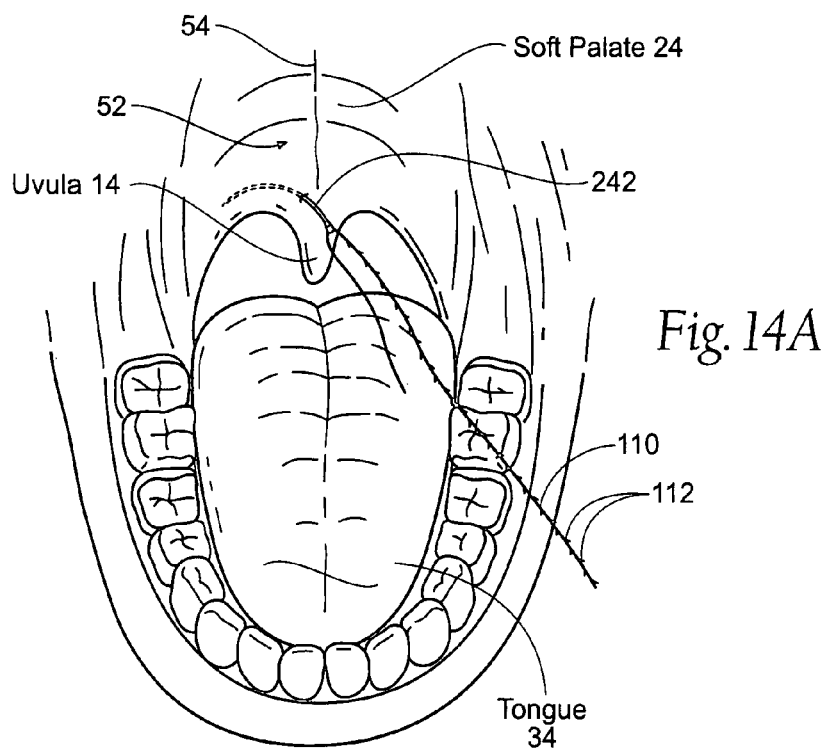
FIGS. 14A to 14F are anatomical views of the oral cavity showing alternate embodiments of inserting one or more barbed suture(s) in the palate and uvula.
Figure 14B:
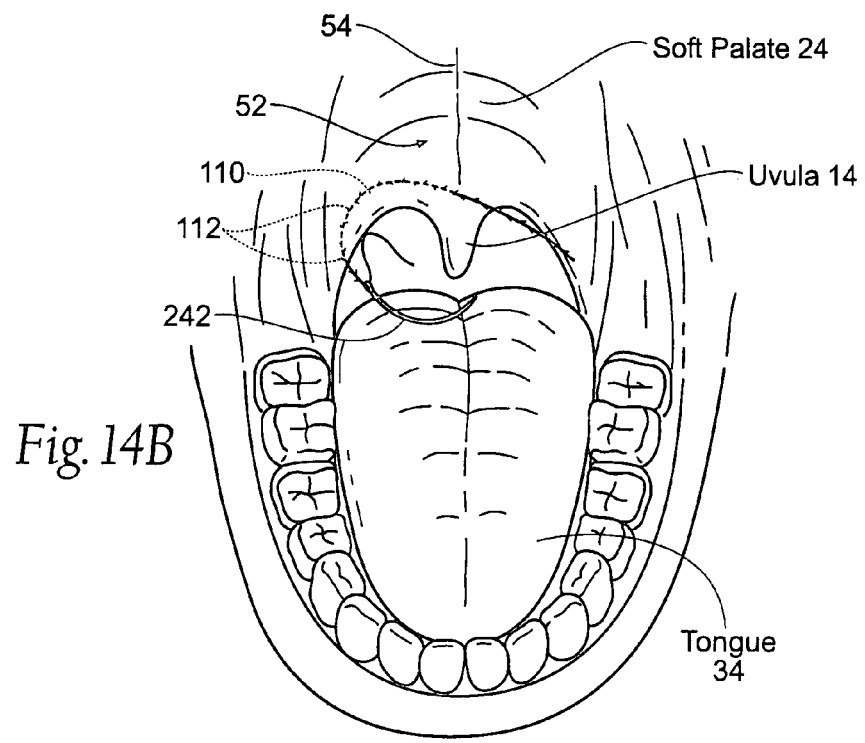
Figure 14C:
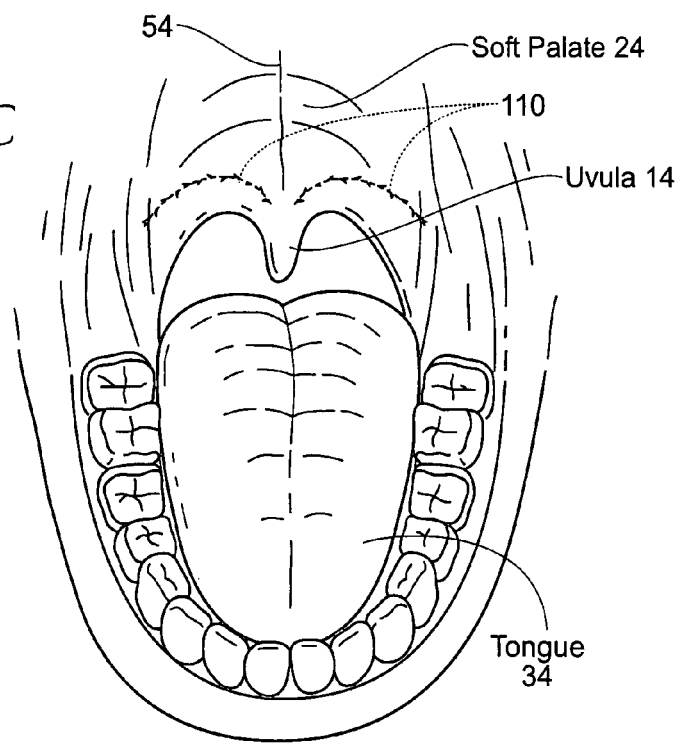

In a representative embodiment of a palatal procedure (see FIGS. 14A and 14B), one or more barbed sutures 110, each threaded to a curved needle 242, is passed through the soft palate 24 perpendicular to the midline 54 of the palate 26 (see FIG. 14A). By pulling on the end of the suture 110 extending from the needle entrance site in a direction opposite to the direction of insertion (as shown in FIG. 14B), tension is applied to the suture, because the barbs 112 extend outward at an angle α to engage tissue and resist movement in this direction. The tension creates tone in the soft palate 24 (see FIG. 14C). The exposed ends of the suture are desirably trimmed, so that the two ends do not stick out of the mucosa of the soft palate 24. Similarly, barbed sutures 110 can be placed in an orientation to tension the palatal arch 52 upward toward the hard palate. The sutures 110 may or may not be attached to the hard palate.

Figure 14D:
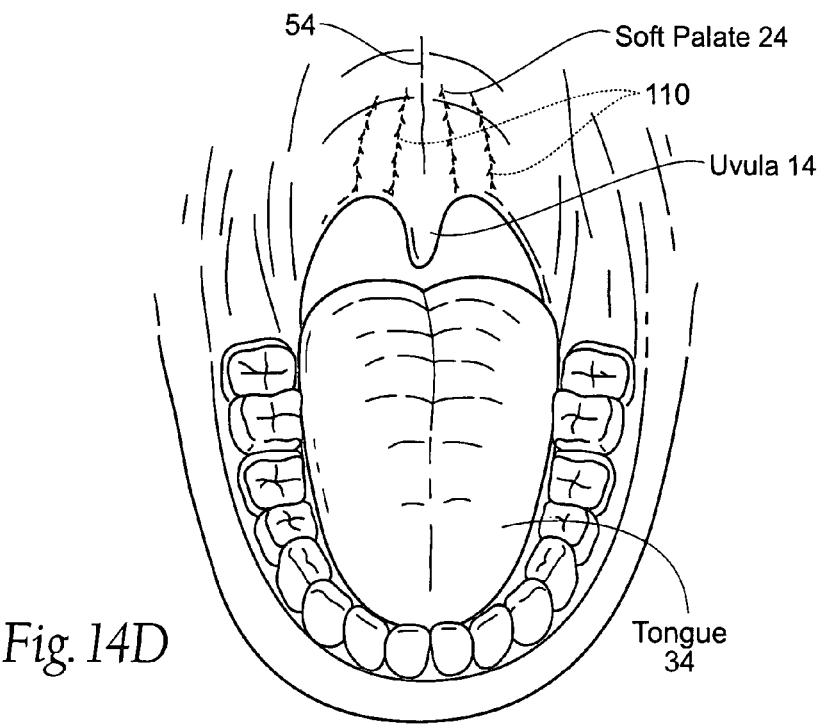

The oral cavity can be the site for a number of additional or alternative procedures. For example, as FIG. 14D shows, one or more barbed sutures 110 running along the midline 54 of the soft palate 24 can shorten the uvula 14. Each suture 110 is inserted by a curved needle 242 in an orientation parallel to the midline 54 of the uvula 14. Again, both ends of the barbed suture 110 are trimmed so as not to stick out of the mucosa. A loop of barbed suture 110 can be inserted in the same fashion starting in the hard palate 28, continuing into the uvula 14, and then returning to the hard palate 28. The tension in the loop will retract the uvula 14.

Figure 14E:
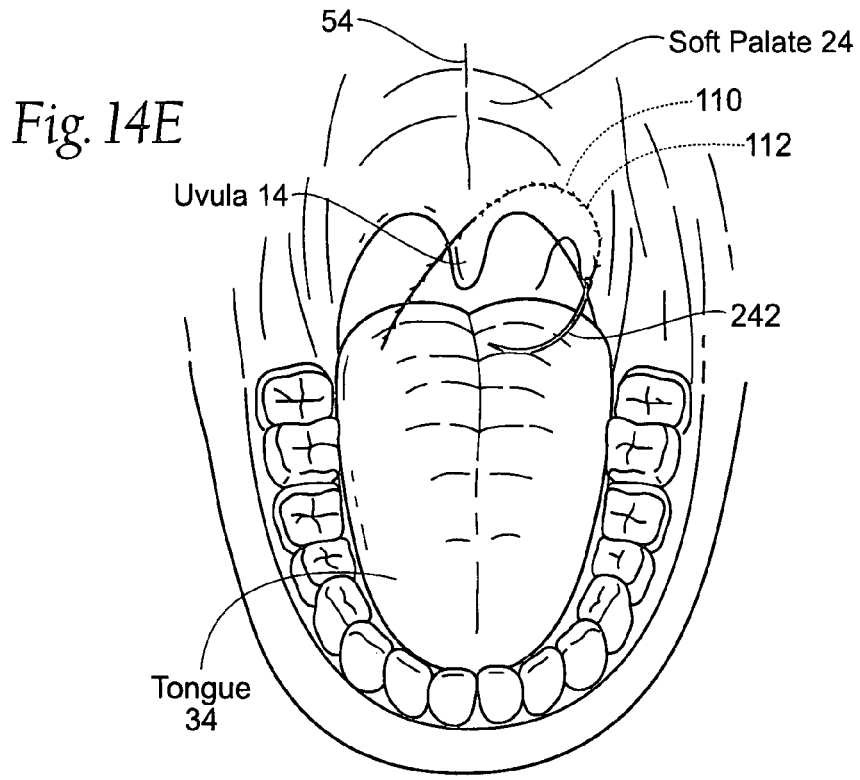
Figure 14F:
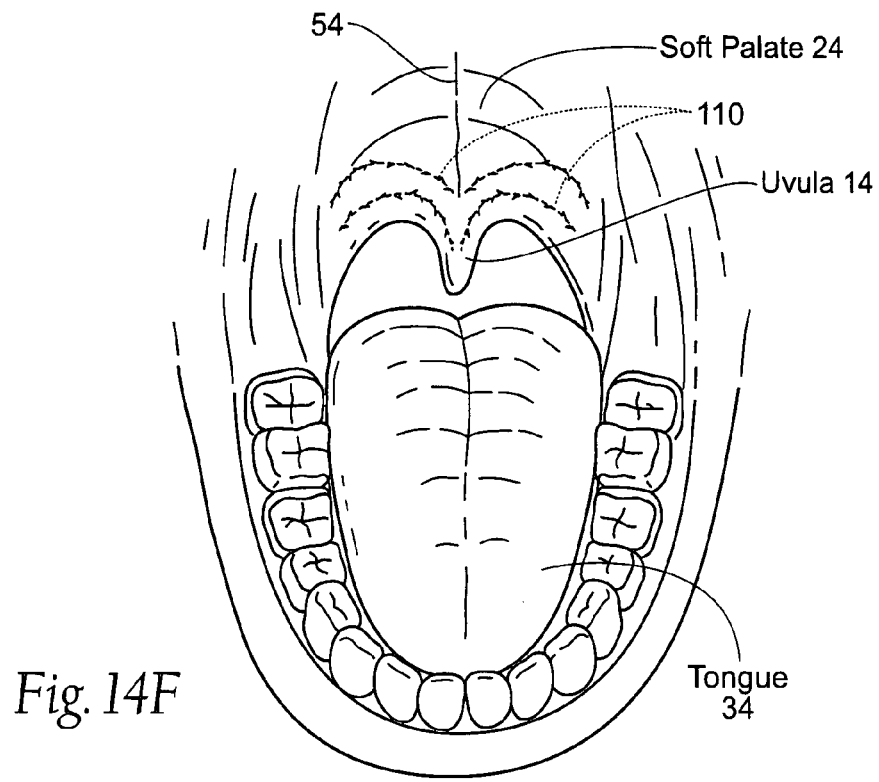

As shown in FIGS. 14E and 14F, one or more barbed sutures can be each inserted by a curved needle 242 to pass in a desired orientation through either or both pharyngopalatine and glossopalatine arches 52, based upon the individual patient's needs.

Figure 15A:
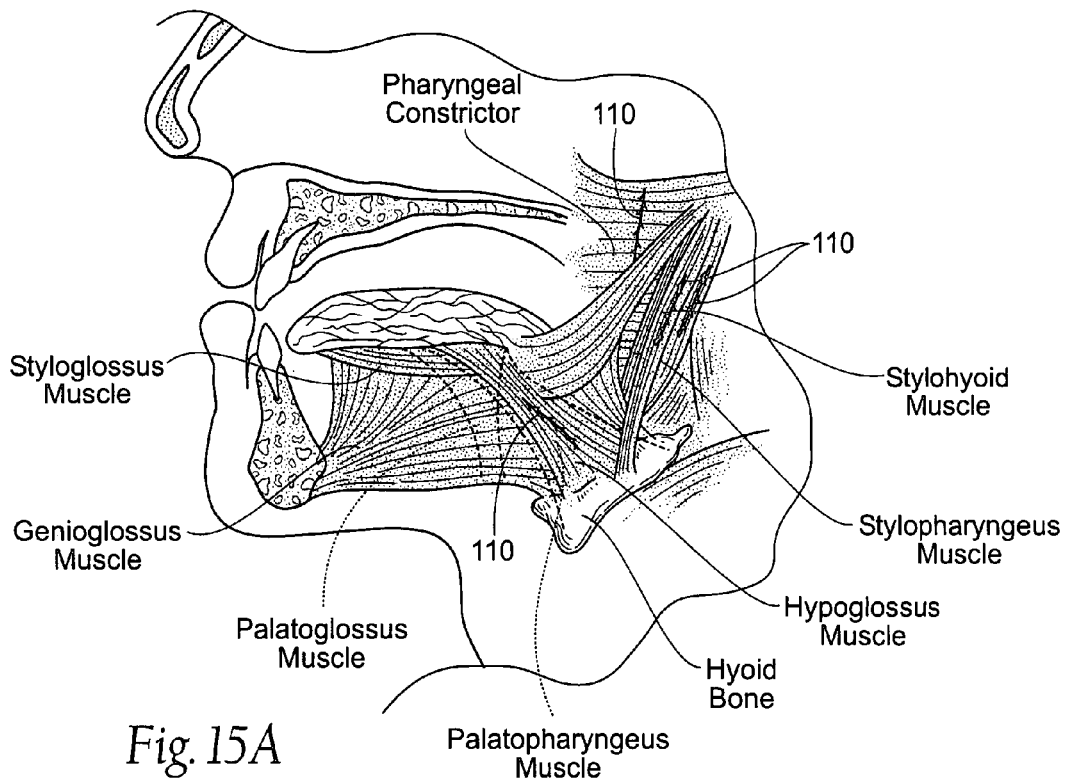
FIGS. 15A and 15B are anatomical sagittal views of the muscles of the upper respiratory tract, similar to those shown in FIG. 1B and FIG. 3C, respectively, showing barbed sutures that have been implanted to affect desired tissue orientations.

E. Representative Instrument and Method of Implanting Barbed Sutures in the Upper Respiratory Tract Muscles Implanting one or more barbed sutures 110 in one or more desired orientations to tension any combination of the lateral pharyngeal wall muscles, including the stylohyoid, hyoglossus, stylopharyngus, palatoglossus, palatopharyngeus and pharyngeal constrictor muscles (shown in FIG. 15A), can help eliminate lateral airway wall collapse. The desired orientation in this embodiment is governed by the treatment objective of tensioning the barbed sutures 110 to shorten the muscles in an axial (i.e., generally inferior to superior) direction, or tensioning the muscle(s) laterally by attachment to the underlying structures, for example the prevertebral fascia. A combination of techniques, such as axial sutures 110 that run laterally into the underlying structures at one end, could also be used.

Figure 15B:
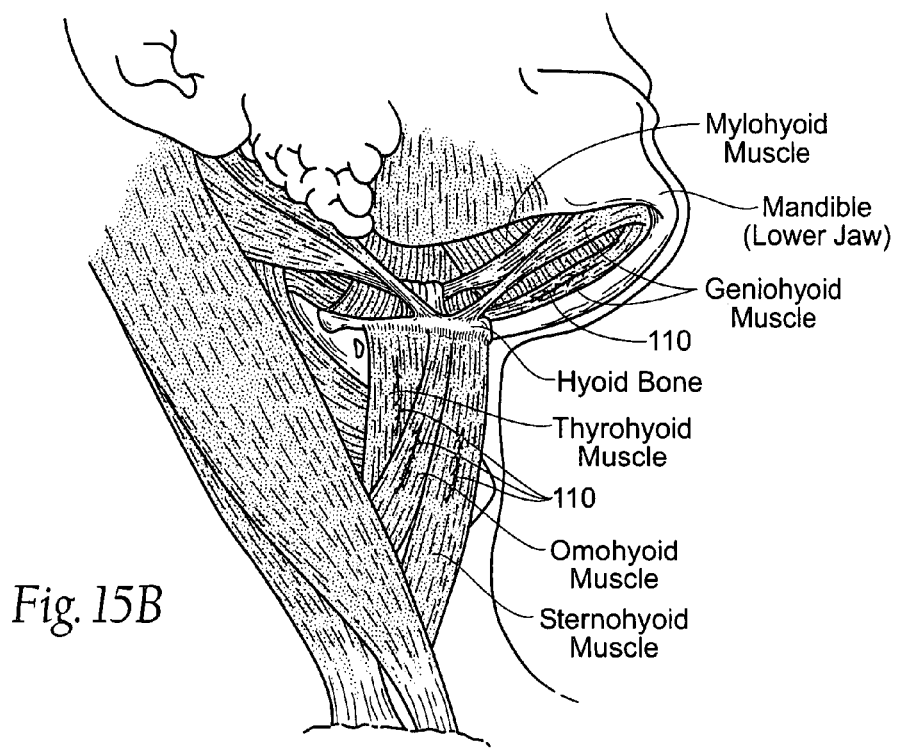

Implanting one or more barbed sutures 110 in one or more desired orientations to tension any of the muscles that attach to the hyoid (e.g. the strap muscles, omohyoid, geniohyoideus, etc.) (see FIG. 15B) can serve to advance, or re-position the hyoid to open the airway. Combination of sutures 110, e.g., placed in the palatine arch (as previously described) as well as placed in muscles along the upper respiratory tract, can treat broad sections of the airway.

F. Representative Instrument and Method of Implanting Barbed Sutures in the Epiglottis One or more barbed sutures 110 can be implanted in an epiglottis 56 to retain a patent airway (see FIGS. 16A and 16B). Barbed sutures 110 can help treat a "floppy epiglottis" in various ways.

Figure 16A:
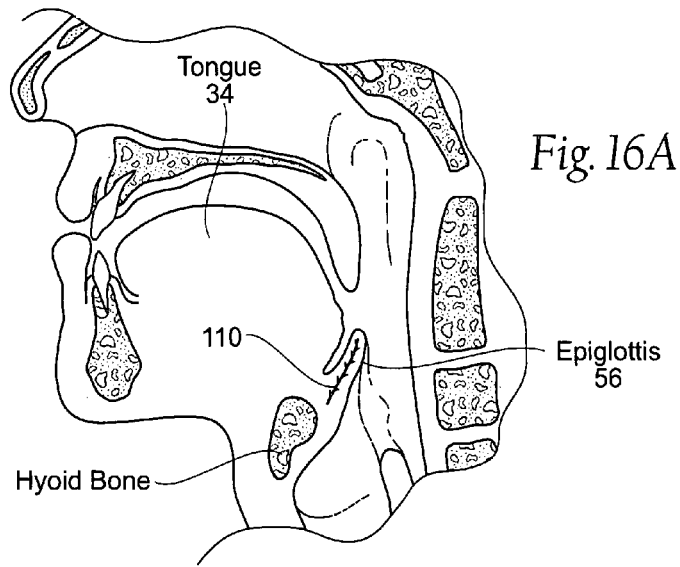
FIGS. 16A to 16C are anatomical sagittal views showing barbed sutures inserted in the epiglottis.
Figure 16B:
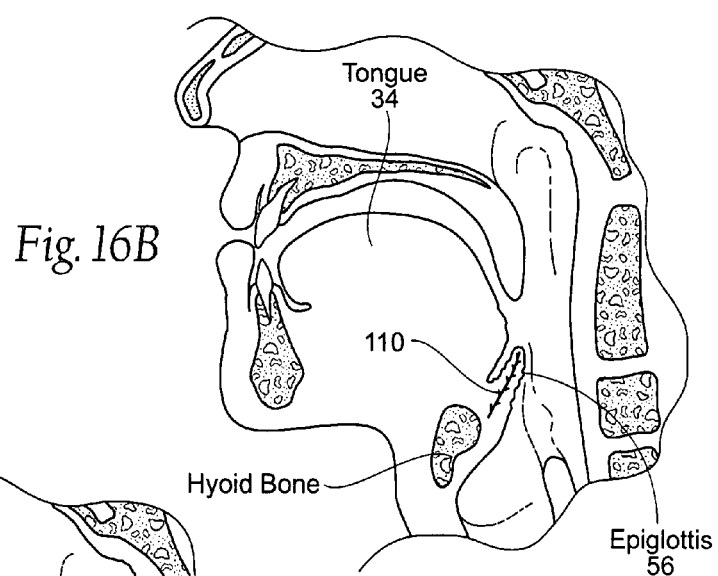
Figure 16C:
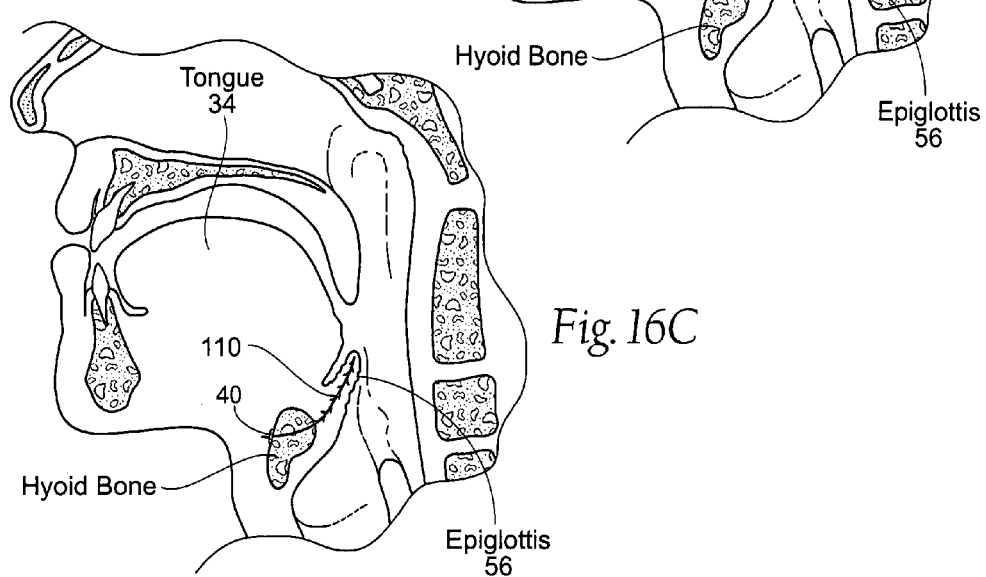

As shown, for example, in FIG. 16A, the suture 110 could be placed so that it lends tone to the epiglottis 56 without significant tensioning. As shown in FIG. 16B, the sutures 110 could create tension within the epiglottis 56 by attaching to other structures or simply "bunching" the tissues of the epiglottis 56. As shown in FIG. 16C, the sutures 110 could be placed through the epiglottis 56 and attached to other structures (e.g. thyroid cartilage, hyoid bone, geniohyoid muscle, etc.) to re-position the epiglottis 56.

IV. Standard Sutures and the Treatment of Apnea

Figure 17A:
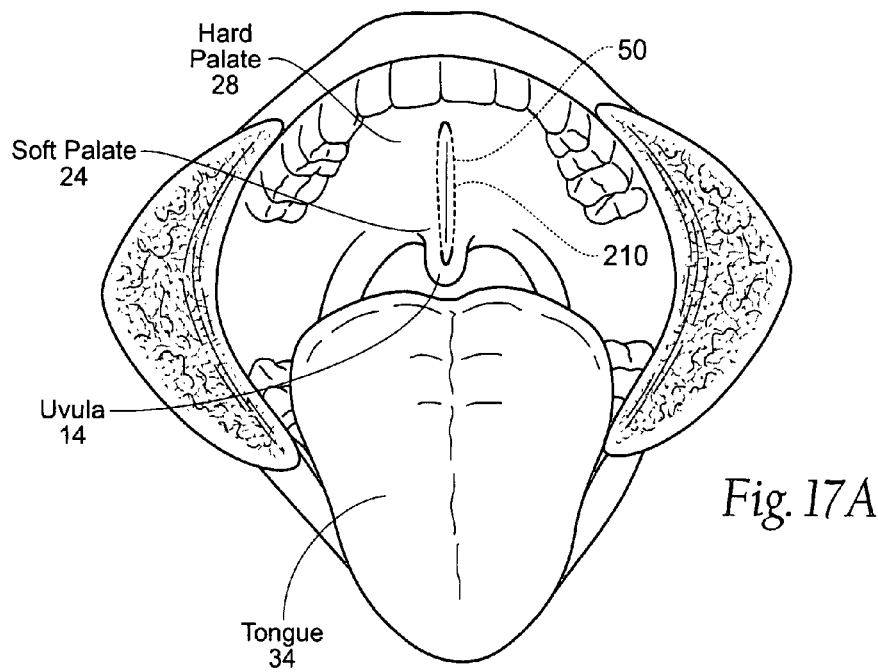
FIGS. 17A to 17C are anatomical views of the oral cavity showing sutures inserted in the palate.

Traction stitch uvuloplasty on the soft palate 24 may also be performed using standard, non-barbed sutures forming a suture loop 50 see FIG. 17A. The standard suture loop 50 can be applied using a needle that would be inserted in the hard palate 28 and then exit briefly at the uvula 14, and then continue back up through the uvula 14 tissue, to return for the final exit through and eventual attachment to the hard palate 28.

Figure 17B:
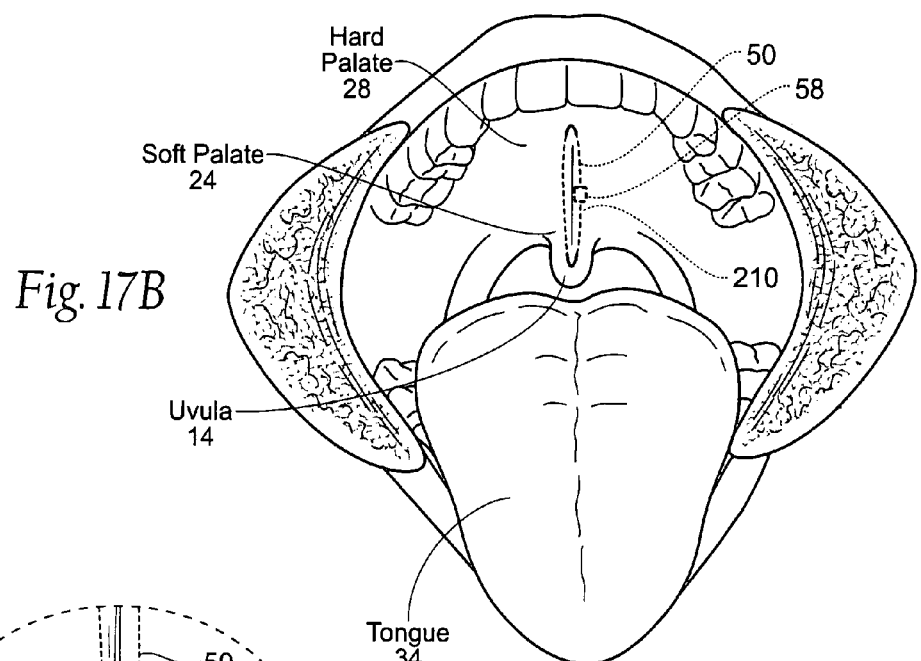

As another alternative shown in FIG. 17B, the suture loop 50 could run directly through the soft tissue at the junction of the hard palate 28 and soft palate 24. A sliding knot could allow tensioning of the loop 50 to adjust uvular position; however, it is desirable to also use an additional device 58, as described in the section that follows, to affect this tension.

Figure 17C:
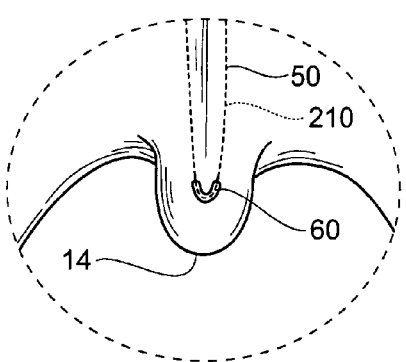

The uvula end of the suture loop 50 may require using a pledget 60 to prevent the tissue from tearing or reforming, see FIG. 17C. The pledget 60 would desirably be buried through a mucosal incision attached to the surrounding tissue or contain barbs (not shown) to help the pledget 60 grip to the tissue. In the preferred embodiment, the pledget 60 is formed as a pad that sits between the tissue of the patient and the suture. In an alternative embodiment, the suture may run through the pledget 60.

In order to facilitate potential removal of the traction stitch, the pledget 60 should desirably contain ferromagnetic/magnetic or radio-opaque material. Desirably, the termination of the loop 50 at the hard palate 28 will permit adjustability to fine-tune the stitch tension, both interoperatively and via a simple in-office procedure.

Figure 18A:
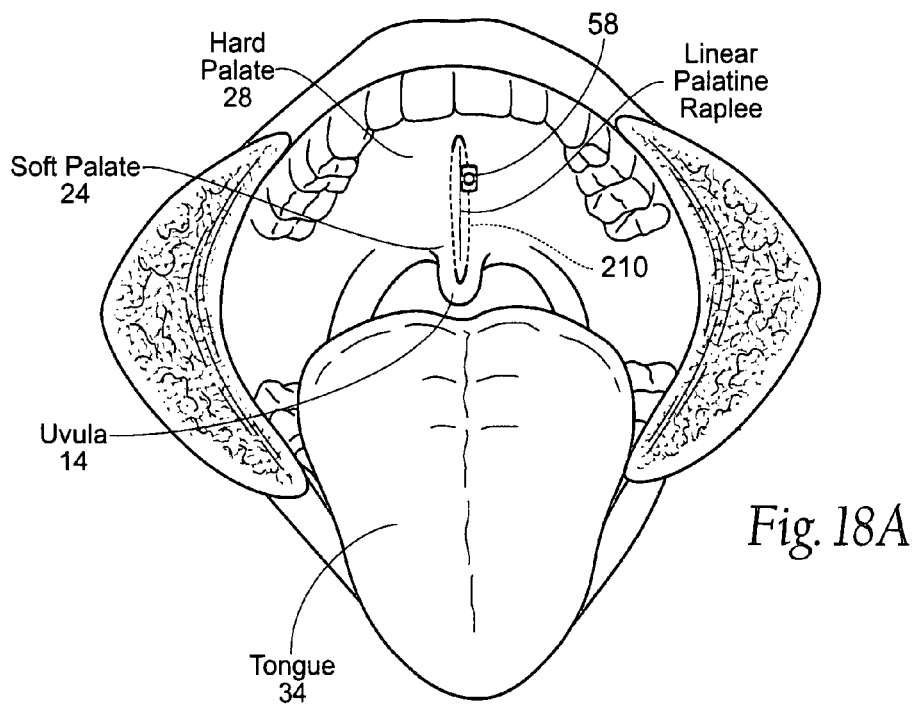
FIG. 18A is an anatomical view of the oral cavity showing a device for adjusting tension in sutures.
Figure 18B:
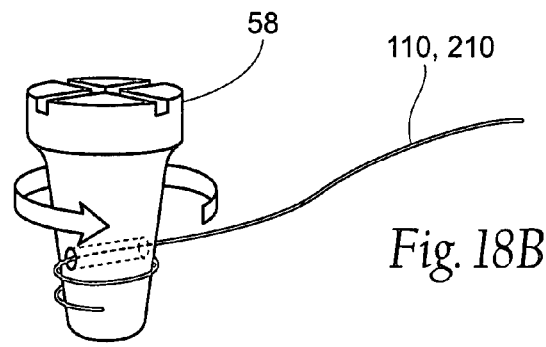
FIG. 18B is a perspective view of a device for adjusting tension in sutures.
Figure 18C:
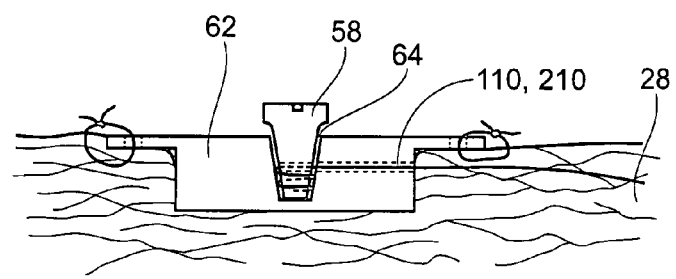
FIG. 18C is a cross-sectional view of the device of FIG. 18B implanted in the palate as shown in FIG. 18A.

V. Adjustment and Removal of Method of Sutures in the Oral Cavity and Upper Respiratory Tract A. Adjustment of Sutures The tension in the sutures 110/210 may be adjusted in various ways. As seen in FIGS. 18A to 18C, one of the means for adjustment of the tension in the suture 210 involves a tapered peg 58. In this method, a base plate 62 containing a hole 64 is attached to the hard palate 28. As seen in FIG. 18B, the suture 210 is threaded through and tied to a tapered peg 58 fitted for the hole 64 in the base plate 62. The length of the suture 210 is then adjusted to maximize its therapeutic result by twisting the tapered peg 58 to wrap the end of the suture 210, around it and then inserting and securing the tapered peg 58 into the hole 64 in the base plate 62 (as shown in FIG. 18C). This type of adjustment may also be used with barbed sutures 110. The barbed part of the suture 110 is passed through the soft tissue to its desired anchoring point (e.g., the uvula), as previously described. In the case of barbed sutures 110, the smooth end is threaded through and tied to the tapered peg 58. The rest of the adjustment remains the same as for standard sutures 210.

Figure 19A:
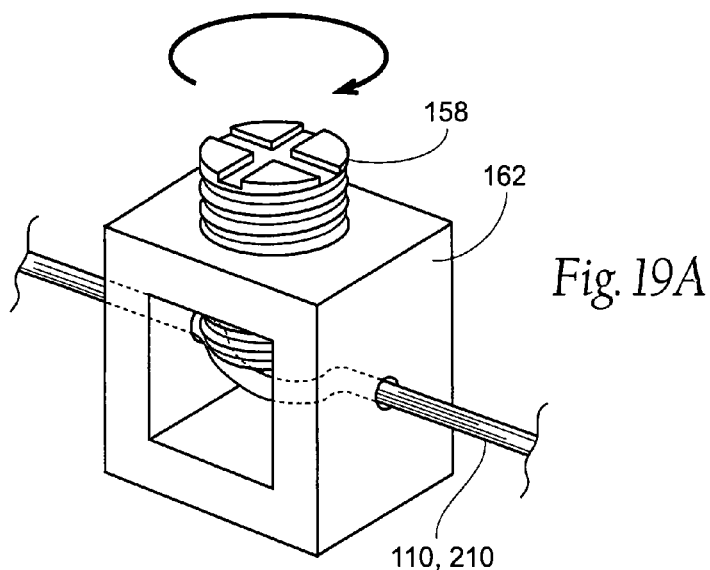
FIGS. 19A and 19B are perspective views of an alternate device for adjusting tension in sutures.
Figure 19B:
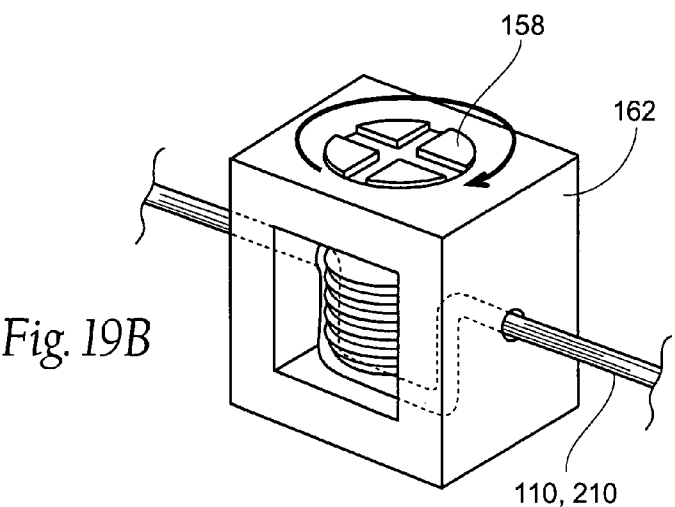

Alternative embodiments of tensioning means include a peg and a hole that have grooves or other surface features to improve the grip, tapering that is applied to either the peg or the hole, but not both, the peg and the hole can have relatively straight profiles, e.g. no tapering, but have significant features that allow them to interlock, in a similar fashion to gear teeth. As shown in FIGS. 19A and 19B, one embodiment includes a first structure 162 through which the suture 110 is threaded. A second peg-like structure 158 screws into the first structure 162 and, by screwing into the first structure 162, forces the suture 110 to deviate from its normal straight path (see FIG. 19B). The deviation of the suture 110 shortens the suture 110 in the soft tissue and thus, serves to tighten the suture 110.

Figure 20:
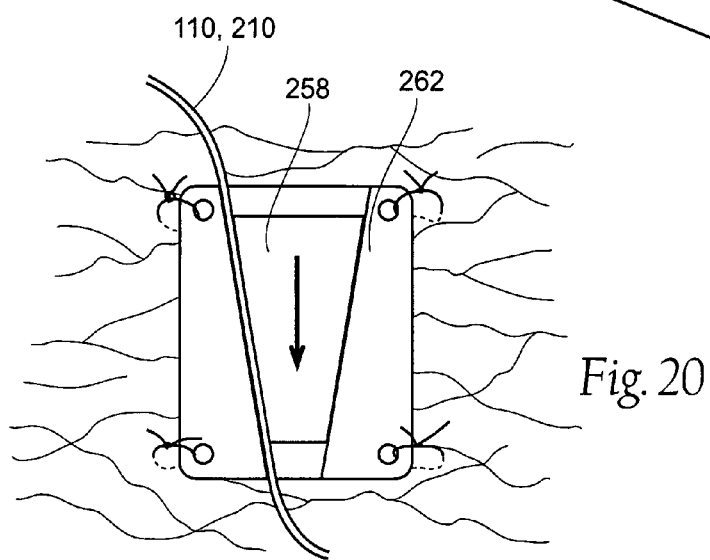
FIG. 20 is a side cross-sectional view of an alternate device for adjusting tension in sutures.

As shown in FIG. 20, another alternative includes a second structure 258 that can lock into the first structure 262 in such a manner as to grip the suture 110/210 between the two structures 258/262. One or both of the structures 258/262 would desirably be tapered to grip the suture 110/210, arranged so that tension in the suture 110/210 tightens the interface between the structures 258,262.

Figure 21:
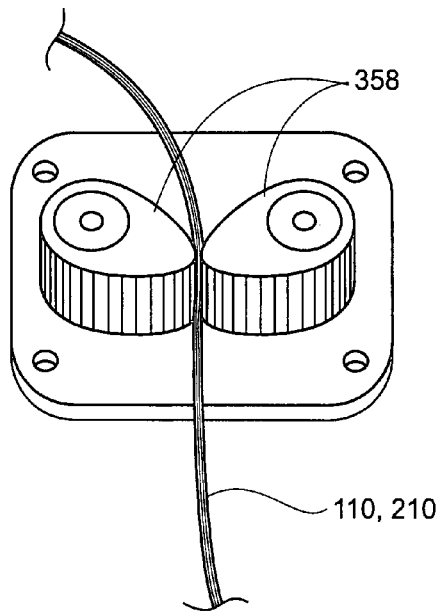
FIG. 21 is a perspective view of an alternate device for adjusting tension in sutures.

In yet another embodiment shown in FIG. 21, a miniature cam cleat 358 would be used to grip the suture. As the suture 110/210 is pulled in the direction indicated by the arrows, the cam cleat 358 is pulled into tighter engagement and the suture 110 is secured between the cam cleats 358. Other suture-gripping devices include devices designed to grip ropes in mountain climbing or sailing, in a miniature version.

Figure 22A:
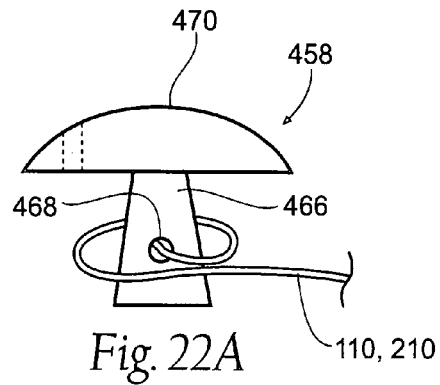
FIG. 22A is a side view of an alternate device for adjusting tension in sutures.
Figure 22B:
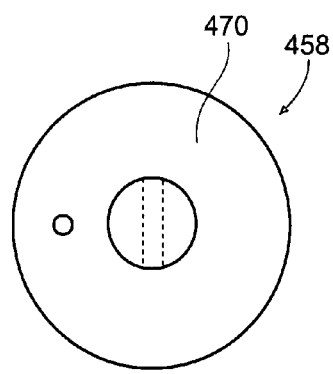
FIG. 22B is a top plan view of the device shown in FIG. 22A.
Figure 22C:
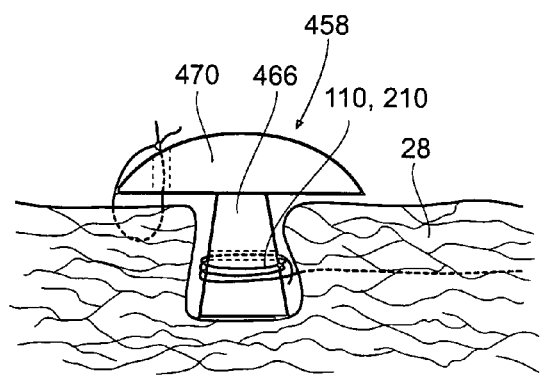
FIG. 22C is a cross-sectional view of the device of FIG. 22A implanted in the palate.

As seen in FIGS. 22A, 22B, and 22C, another means of adjusting the barbed sutures 110/210 involves using a plastic or titanium mushroom-type device 458. FIG. 22A shows a mushroom-type device 458 which includes a stem 466 with a hole 468 through which a suture 110/210 will be threaded. The stem 466 of the mushroom-type device 458 is placed in a pocket either in the oral cavity tissue itself or in a base structure that is attached to the oral cavity tissue, see FIGS. 22B and 22C. The suture 110 will be twisted around the mushroom stem 466 to adjust the tension. The head 470 of the mushroom will be stapled, sutured, or attached to either an additional hole in the hard palate 28 or at the junction of the soft palate 24 and hard palates 28, so as to stabilize its rotation. The mushroom shape 458 has the advantage of presenting a smooth profile over which the mucosa can easily heal. Although the mushroom 458 is preferably made of plastic or titanium, it should be clear to one of skill in the art that the mushroom 458 could be made of any medically acceptable material.

B. Removal of Sutures

Removal of sutures is a particularly important issue with respect to barbed sutures 110. Barbed sutures 110 cannot be removed like conventional sutures which, in the absence of knots, can be moved freely in either direction. The barbed sutures 110 are free to move in one direction—from the initiation point to the anchoring point (e.g., from the hard palate to the uvula). Therefore it is desirable to be able to easily identify the anchoring point. One solution involves placing an identifiable marker close to the anchoring point, such as a pledget 60, see FIG. 17C. The identifiable marker must be easy to find either by palpation or by using a probe. For example, the marker may be X-ray locatable, or the marker may comprise a ferromagnetic bit which could be located using a magnetic probe. Another alternative involves using an ultrasonic probe that will set off a resonant frequency.

Once the marker is located, the surgeon may cut through the surrounding tissue to get to the marker and stabilize it. An incision is then made at the insertion point to snip the barbed suture 110 at its attachment point. Then, while holding on to the identifiable marker, the barbed suture 110 is pulled through its anchoring point.

VI. Systems and Methods for Implanting Structures in, on, or Near an Extrinsic Muscle Region of a Tongue It is also contemplated that other devices and methods could be utilized to stabilize and maintain a patient's airway in order to treat sleep apnea. For example, an implant structure can be sized and configured for implantation in, on, or near an extrinsic muscle region affecting movement and/or shape of a tongue. Examples of such extrinsic muscles include, e.g., the genioglossus, hyoglossus, styloglossus, and palatoglossus, as shown in FIG. 1B. The position of the structure is stabilized relative to the extrinsic muscle region to maintain the tongue in a desired orientation.

An implant structure having these technical features can take various forms, representative examples of which follow.

A. Bracing Member for an Extrinsic Muscle Region

Figure 23A:
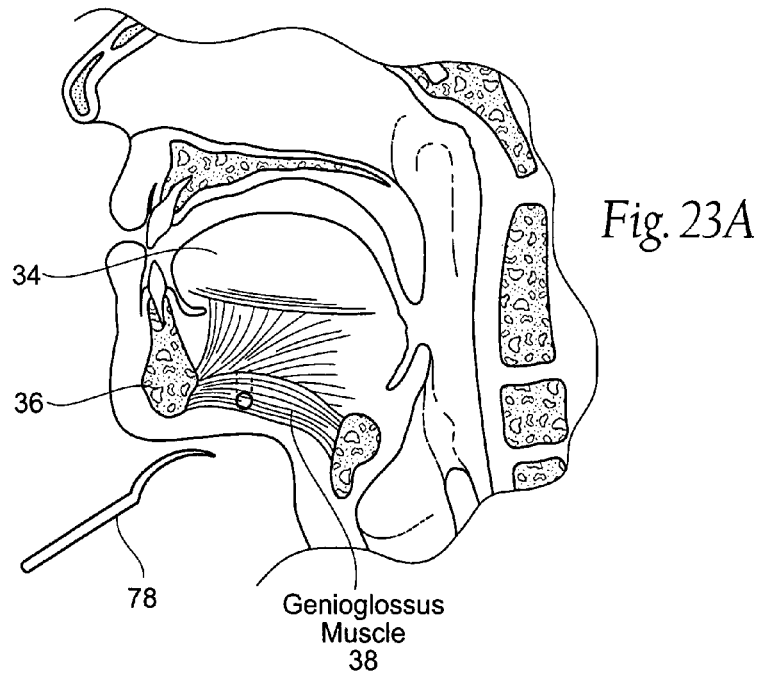
FIG. 23A is an anatomical view of the upper respiratory system.
Figure 23B:
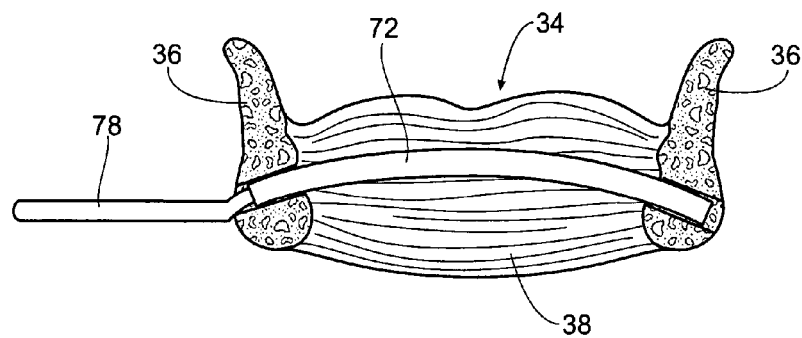
FIGS. 23B and 23C are cross-sectional views of the tongue showing a method of inserting an implant structure comprising a bracing member in an extrinsic muscled region beneath a tongue.
Figure 23C:
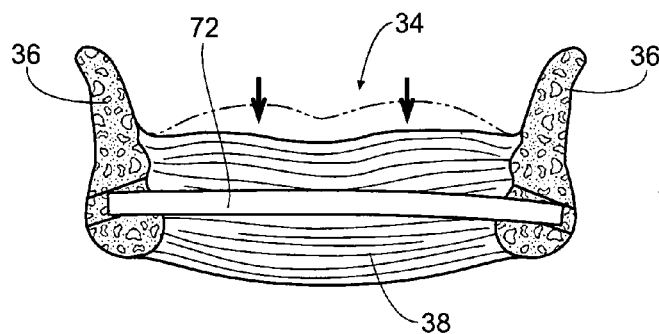

FIGS. 23A to 23C show, as one representative example, an implant structure comprising a bracing member 72 that is sized and configured for implantation in, on, or near an extrinsic muscle region affecting movement and/or shape of a tongue. As shown in FIG. 23A, the bracing member 72 is sized and configured to overlay, at least in part, an extrinsic muscle region beneath the tongue.

As shown in FIG. 23A, an incision is made in the skin on one side of the mandible 36. A hook-like device 78 is inserted that extends up and over the genioglossus muscle 38 and then comes back down on the other side of the mandible 36, as FIG. 23B shows. Through the same skin incision, the bracing member 72 is inserted and the first end of the brace 72 is attached to the first side of the mandible 36, as shown in FIG. 23C. The bracing member 72 uses the same incision as the hook 78, and is inserted such that the brace 72 extends on top of an extrinsic muscle region (which, in FIGS. 23A to 23B, includes the genioglossus muscle 38) and continues to be inserted until it reaches the opposite side of the mandible 36. A second incision is made in the skin under the second side of the mandible 36 and the second end of the bracing member 72 is attached to the second side of the mandible 72. The hook-like device 78 is then removed from the tongue 34.

The bracing member 72 may be attached to the mandible 36 using any medically proven and accepted methods and materials including, but not limited to, small screws and/or biocompatible adhesives.

The bracing member 72 is sized and configured to deflect the extrinsic muscle region (i.e., the genioglossus muscle 38) caudally, causing the tongue 34 to move anteriorly, thus maintaining a patent airway.

B. Hooking Member for an Extrinsic Muscle Region

Figure 24A:
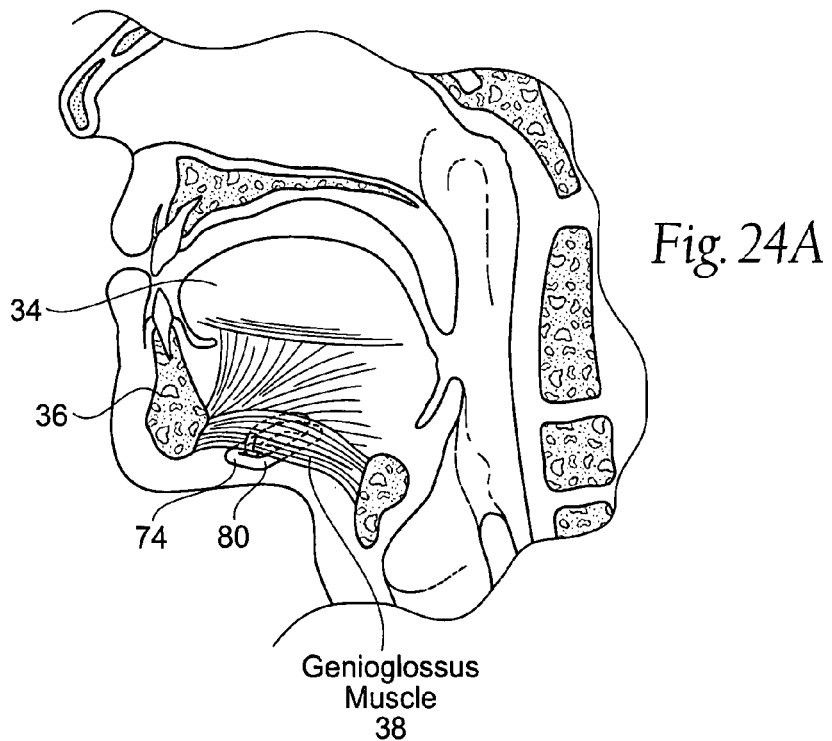
FIGS. 24A to 24C are anatomical views of the upper respiratory system showing an implant structure comprising a hooking member buckle implanted in an extrinsic muscle region beneath a tongue.
Figure 24B:
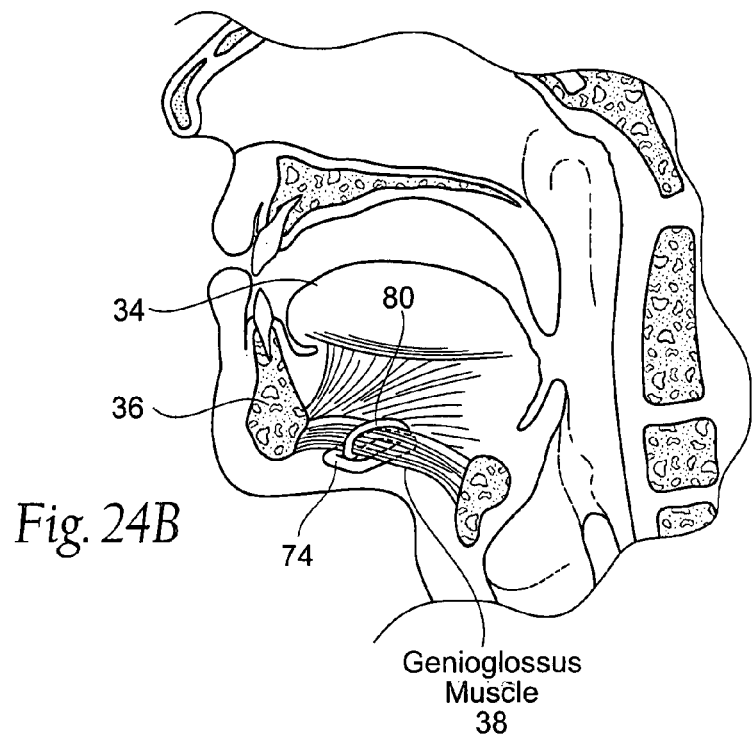
Figure 24C:
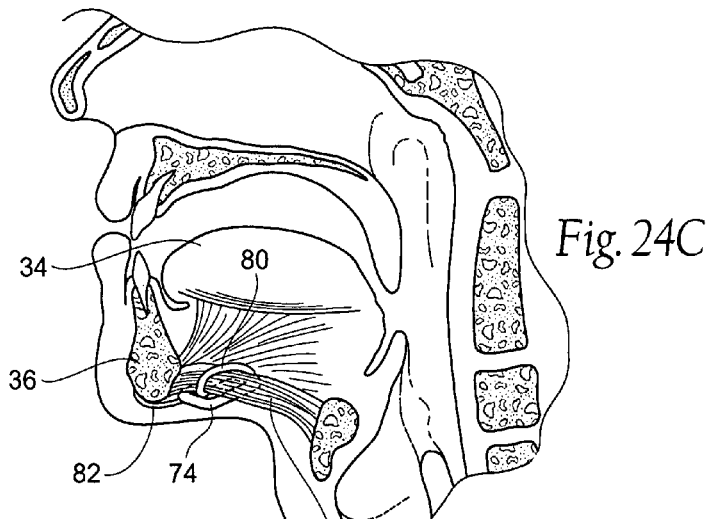

FIGS. 24A to 24C show, as another representative example, an implant structure comprising a hooking member 80 that is sized and configured for implantation in, on, or near an extrinsic muscle region affecting movement and/or shape of a tongue. As shown in FIG. 23B, the hooking member 80 is sized and configured to extend through an extrinsic muscle region beneath the tongue.

As shown in FIGS. 24A to 24C, an anchoring component 74 is coupled to the hooking member 80. As shown in FIGS. 24A to 24C, the assembly of the anchoring component 74 and hooking member 80 have the appearance of a hook (i.e., the hooking element 80) coupled to a buckle (i.e., the anchoring component 74), and these components will therefore in shorthand be referred to as such.

The hook 80 can be formed as a separate piece which couples to the buckle 74, or can be formed as a part of the buckle 74.

As shown in FIG. 24A, an incision is made under the skin to create a pocket sized to fit the buckle 74. The buckle 74 may then be inserted into the pocket, under the extrinsic muscle region (which, in FIGS. 24A to 24C includes the genioglossus muscle 38. The hook 80 is opened to place it over the extrinsic muscle region (i.e., the genioglossus muscle 38), as FIG. 24B shows.

Because the hook 80 is attached to the buckle 74, the genioglossus muscle 38 is deflected caudally, causing the tongue 34 to move in an anterior direction, thus maintaining a patent airway.

In another representative embodiment, as shown in FIG. 24C, the hook 80 can be reattached on the other side of the buckle 74 using a chin attachment clamp 82. A second skin incision on the other side of the mandible 36 might be necessary in order to attach the hook 80 on the other side of the buckle 74. In this arrangement, the buckle 74 includes a chin attachment clamp 82. The first end of the chin attachment clamp 82 is coupled to the end of the buckle 74. The second end of the chin attachment clamp 82 is attached to at least a portion of the chin or mandible 36. Desirably, the chin attachment clamp 82 will be adjustable in length either interoperatively or under local anesthesia so as to permit the surgeon to adjust the position of the buckle 74 to achieve optimal therapeutic effects based on each individual patient's needs. The bend angle on the clamp section can be between 0° and 70°, depending on the individual's needs. Depending on the individual's anatomy, the chin clamp 82 may need to be screwed onto the mandible 36. Once the hook 80 is attached to the buckle 74, the genioglossus muscle 38 is deflected caudally, causing the tongue 34 to move in an anterior direction.

C. Elastomeric Structure for an Extrinsic Muscle Region

Figure 25A:
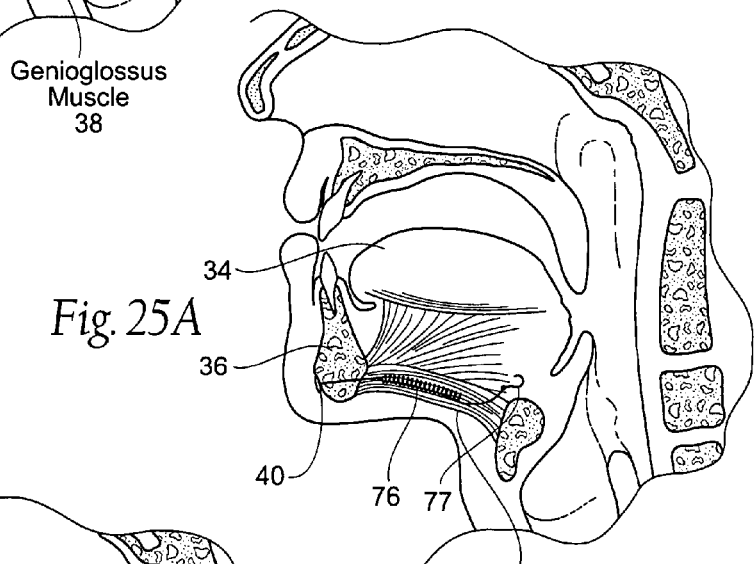
FIGS. 25A and 25B are anatomical views of the upper respiratory system showing an implant structure comprising an elastomeric structure implanted in an extrinsic muscle region beneath a tongue.

FIG. 25A shows, as another representative example, an implant structure comprising an elastomeric structure 76 that is sized and configured for implantation in an extrinsic muscle region affecting movement and/or shape of a tongue. As shown in FIG. 25A, the elastomeric structure 76 takes the form of a spring.

As shown in FIG. 25A, the extrinsic muscle region includes the genioglossus muscle. The spring 76 extends in the muscle region to pull the tongue 34 forward. The spring 76 is coupled to a tissue grasping member, which, in the illustrated embodiment, takes the form of a hook 77 implanted in the tongue 34. The spring 76 implanted in the extrinsic muscle region maintains gentle tension on the hook 77. A bar or button 40 may be attached to the spring 76 on the outer portion of the mandible 36 to retain the spring 76 in its position. As an alternative to the spring 76, an elastomeric band may be used.

Figure 25B:
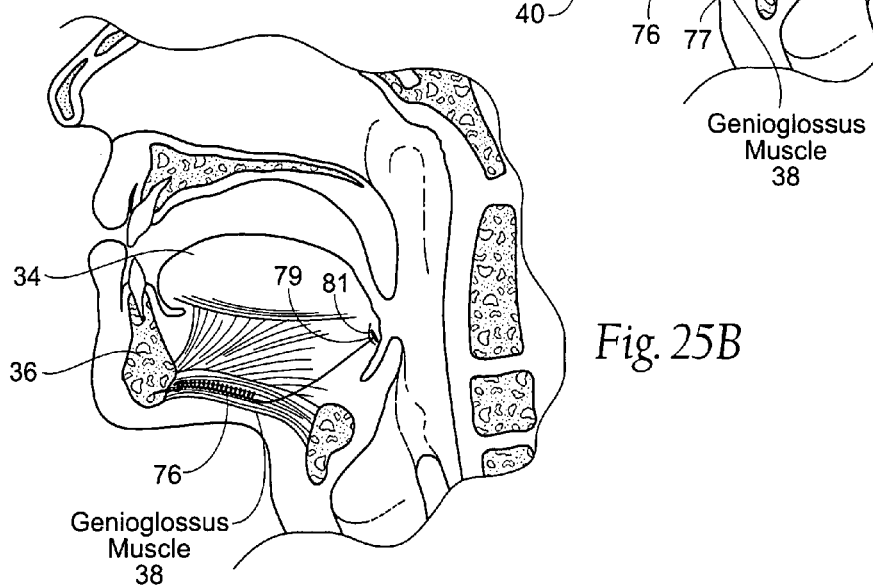

Alternatively (as shown in FIG. 25B), a needle can be placed all the way through the tongue 34. A pocket 79 may be formed in the submucosa in the vicinity of the needle exit point. In this arrangement, a clip 81 can be fastened to the spring 76 in the pocket. This arrangement could eliminate the bar 40.

D. Tissue-Tensioning Elastomeric Structure

Figures 26A, 26B, 26C, 26D:
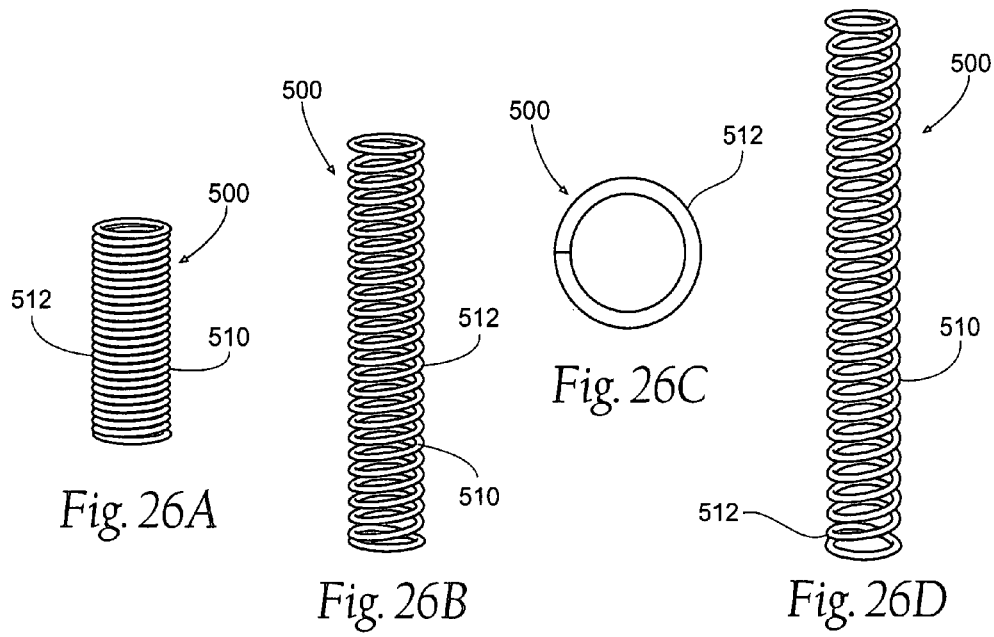
FIGS. 26A to 26D are views of an illustrative embodiment of an elongated elastomeric body sized and configured for implantation in a desired orientation in a tissue region in an airway.
Figures 27A, 27B, 27C, 27D:
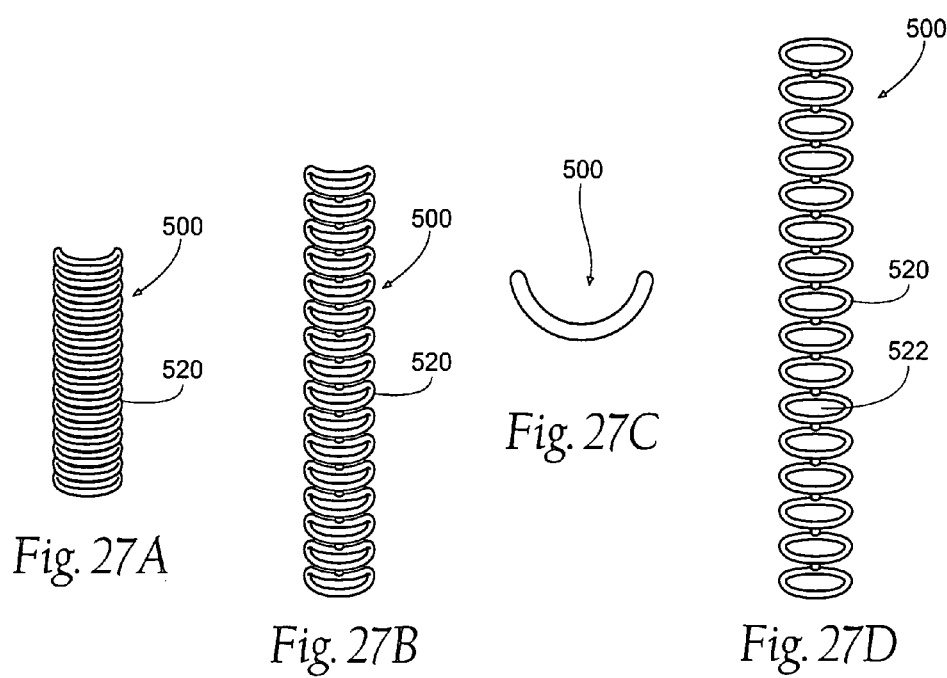
FIGS. 27A to 27D are views of an illustrative embodiment of an elongated elastomeric body sized and configured for implantation in a desired orientation in a tissue region in an airway.
Figure 28A:
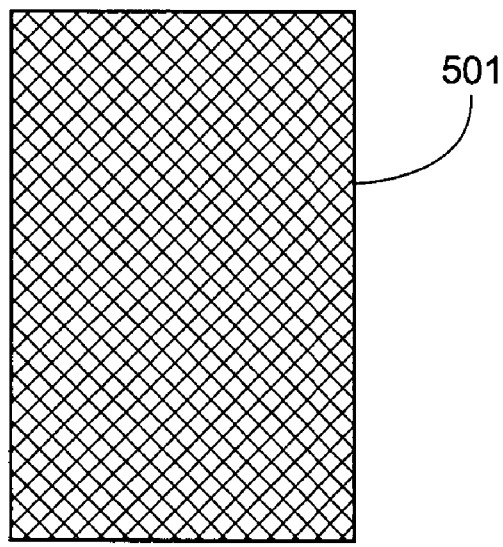
FIGS. 28A to 28B are views of an illustrative embodiment of an elongated elastomeric body sized and configured for implantation in a desired orientation in a tissue region in an airway.

FIGS. 26A, 27A and 28A show additional representative examples of an implant structure comprising an elastomeric structure 500 sized and configured for implantation in a tissue region affecting movement and/or shape of a tongue. As shown in FIGS. 26A and 27A, the treatment device takes the form of an elongated elastomeric structure 500 that is sized and configured for implantation in a desired orientation in the tongue or an extrinsic muscle of the tongue. The elastomeric implant structure 500 is adapted to reshape or move the tongue when implanted in the tongue of an extrinsic muscle of the tongue.

As shown in FIGS. 26A to 26D and 27A to 27D, the elastomeric structure 500 may take the form of a spring. Although the structure 500 may have any cross-sectional shape, in the illustrated embodiments, the elastomeric structure has a generally circular (for example, the coiled spring structure 510 shown in FIG. 26C) or semicircular cross-section (for example, the semicircular spring structure 520 shown in FIG. 27C).

The elongated elastomeric structure 500 is also desirably generally elastic. The illustrated embodiments contain coils 512 or perforations 522 which allow the elastomeric structure to switch between a relaxed state (see FIGS. 26A and 27A) and an extended, stressed state (see FIGS. 26D and 27D).

Figure 28B:
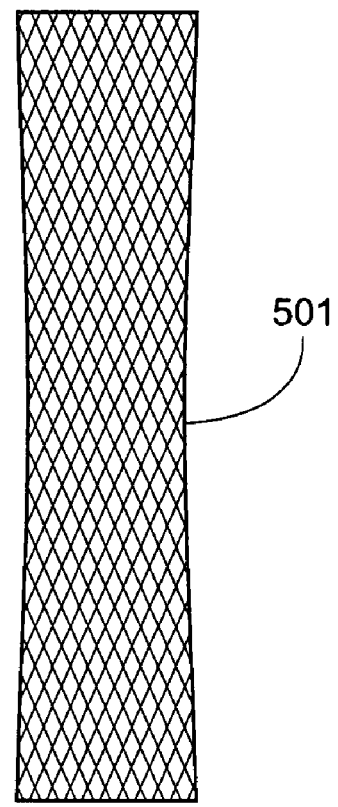

As shown in FIGS. 28A to 28B, the elastomeric structure 500 may take the form of a braided tube 501 that resembles Chinese finger cuffs. As seen in FIG. 28A, in its relaxed position, the tube 501 has a relatively wide diameter and shorter length. As seen in FIG. 28B, in its elongated position the tube 501 has a relatively narrow diameter and is significantly longer than in the relaxed position.

The elongated elastomeric structure 500 can be made of metal material, e.g., Nitinol, other shape-memory alloys, shape-memory polymers, or titanium, as well as any other material known in the art to exhibit similar characteristics of biocompatibility, elasticity, and resilience.

The elongated elastomeric structure 500 may further be flexible to facilitate its implantation in a targeted tissue region of an individual and thereafter conform to the desired tension and orientation. The desired tension and orientation will depend upon the morphology of the tissue region and the particular treatment objectives.

In use, the elastomeric structure desirably is implanted in the tissue when the structure is in a stressed or extended state (see FIGS. 26D, 27D and 28B). In this manner, after the structure is implanted into the tongue, the structure will revert to its natural, unstressed position, thus pulling the tongue into a more forward position. The elongated elastomeric structure may, but does not necessarily need to, be anchored to the mandible.

In use, one or more elongated elastomeric structures 500 can be implanted at a selected tissue region, depending upon the treatment objectives. The number of implanted elongated elastomeric structures 500 is governed by the location of the tissue region and the treatment objectives, e.g., a desired shape or bias that is to be imparted to the tissue region, and/or the maintenance of a desired tension in the tissue region, and/or the maintenance of a desired orientation of the tissue region relative to another tissue region, e.g., to keep an airway patent.

The desired orientation comprises the selective application of tension to the elongated elastomeric structure 500 after its implantation to affect a desired change in shape, orientation, and/or other physiologic characteristic within the tissue region.

The desired orientation in this embodiment is governed by the treatment objective of urging or maintaining the tongue in a desired anterior orientation away from the uvula and/or pharyngeal wall. The relaxed/shortened structure 500 serves to maintain tension, so that the tissue region itself is maintained in a desired orientation, to thereby resist posterior collapse of the tongue against the uvula and/or the pharyngeal wall.

It is desirable to place the elastomeric structure into an extended or stressed position (see FIGS. 30A to 30F), and retain the structure in that position for at least the period of time during which the implant is being implanted into the tongue. The elongated elastomeric structure 500 can be placed into an extended or stressed position (see FIGS. 30A to 30F) in various ways.

In a first representative example the implanted elastomeric structure 500 can comprise a shape memory metal material that assumes a predetermined, remembered shape in response to an applied activation energy. The activation energy can comprise thermal energy, as well as electrical energy, mechanical energy, electromagnetic energy, acoustic energy, or light energy.

The shape memory material can comprise an alloy, e.g., Nitinol® alloy (an alloy consisting of nickel and titanium), and copper based alloys, most commonly Cu—Zn—Al and Cu—Al—Ni. The shape memory material 44 can also comprise a shape memory polymer.

Figure 29A:
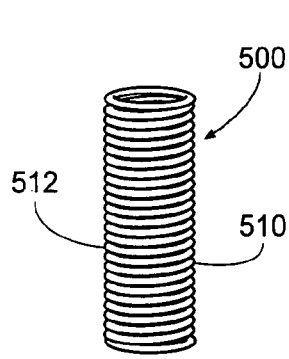
FIGS. 29A to 29B are views of an illustrative embodiment of an elongated elastomeric body sized and configured for implantation in a desired orientation in a tissue region in an airway.
Figure 29B:
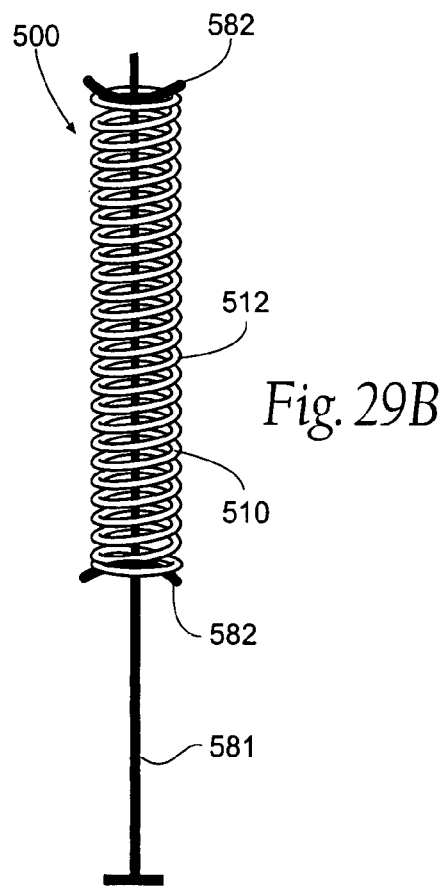
Figure 29C:
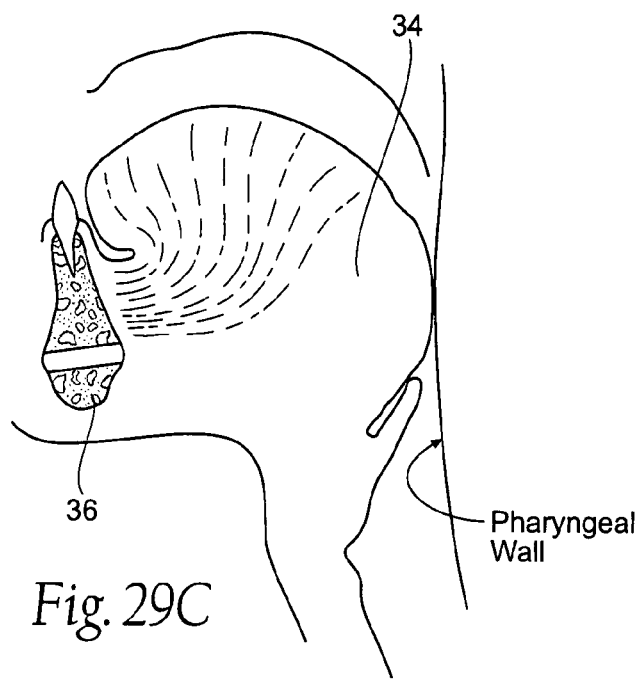
FIGS. 29C to 29G are anatomical sagittal views showing a method of inserting the elastomeric body of FIG. 29A or 29B in a human.
Figure 29D:
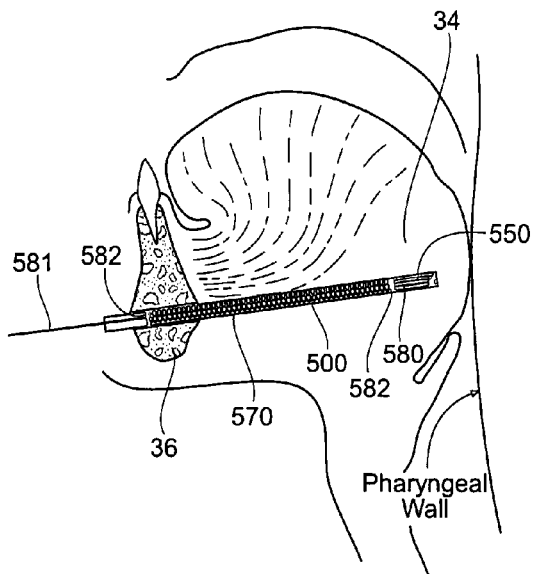
Figure 29E:
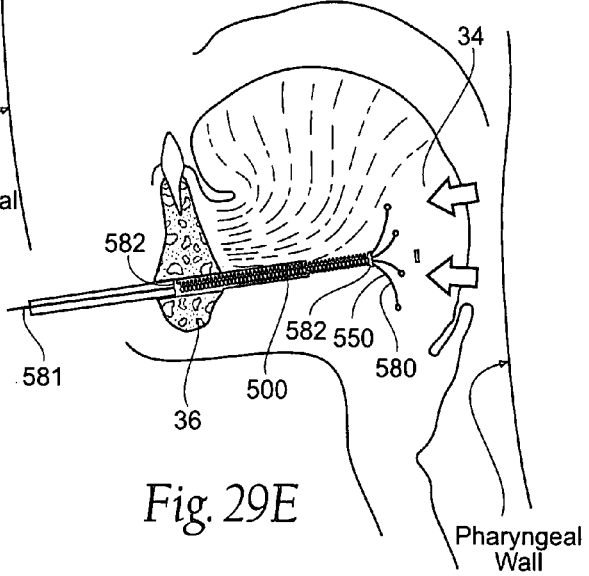

FIG. 29B shows an elastomeric structure 500 made of a Nitinol® shape memory alloy. The structure 500 is implanted in the tongue (see FIGS. 29D to 29G). As shown in FIG. 29B, the structure 500 possesses relatively compliant mechanical properties at certain temperature conditions (in this case, 25° Celsius), which is sometimes called the soft martensitic phase. Since structure 500 is soft during the martensitic phase, it is maintained in an elongated shape using an internal support within the delivery cannula 570, which may take the form of a plunger device 581 with arms 582 that are released upon implantation within the tongue tissue, see FIGS. 29D to 29E. Alternatively, as will be described in the following section, structure 500 in the martensitic phase may also be maintained in an elongated state using various biodegradable materials or structures.

Figure 29F:
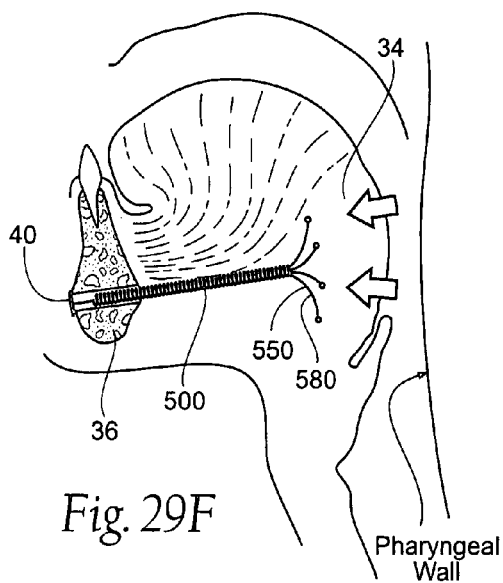
Figure 29G:
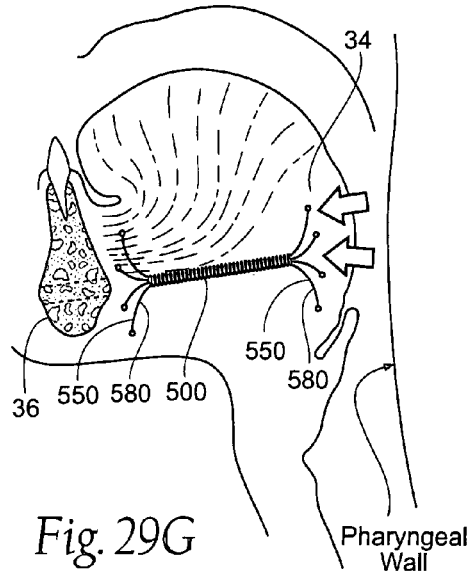

In response to increased temperature conditions, the structure 500 assumes less compliant mechanical properties (see FIGS. 29F and 29G), accompanied by accelerated shape change. This is sometimes called the hard austenitic phase. In this phase (as shown in FIGS. 29F and 29G), the structure 500 provides a dynamic resistance to shape change. In the illustrated embodiment, the change in temperature conditions is brought about by an external activation energy source that is used when activation is desired. The activation source can comprise a source of heat, in this case, implantation into tongue tissue. Upon raising the temperature of the elastomeric structure 500 to normal body temperature (approximately 37° Celsius), the elastomeric structure 500 shortens in length and, in the process tensions the tongue tissue causing the airway to remain patent when the muscles otherwise relax during sleep.

In the case of the elastomeric structure 500 that resembles Chinese finger cuffs, the structure also enters a martensitic phase at approximately 25° Celsius. During this martensitic phase, structure 500 is weakened and can be elongated. As with the previous example, during the martensitic phase structure 500 needs to be supported by a plunger device 581, or similar device. Once structure 500 has been implanted in the tongue tissue, its internal temperature rises to approximately 37° Celsius, and the structure enters the austenitic phase, where structure 500 once again becomes rigid and shortens in length. As seen in FIG. 28B, during the martensitic phase the angle β, between two braids that cross over each other and where the angle faces either one of the two hollow ends of structure 500, is less than 90°. As structure 500 re-enters the austenitic phase, the same angle widens considerably to return to its pre-set value of over 90°. Again, upon raising the temperature of the elastomeric structure 500 to normal body temperature (approximately 37° Celsius), the elastomeric structure 500 shortens in length and, in the process tensions the tongue tissue causing the airway to remain patent when the muscles otherwise relax during sleep.

In a second representative example the structure is placed in a stressed position by stretching the structure 500 and filling the space created between coils 512 of structure 510 (FIG. 30A) or within the opened perforations 522 of structure 520 (FIG. 30C), with a bio-absorbable material 530 capable of quick absorption by the body. The bio-absorbable material may include substances such as collagen, fibrin glue, or polyglycolic acid (PGA). Desirably, the mass absorption period of the bio-absorbable material 530 used to fill the perforations or the space between the coils of structure 510 will be less than the amount of time necessary for tissue in-growth to start between the coils 512 (FIG. 30A) or in the perforations 522 (FIG. 30C) (usually about three weeks). In this manner, when the bio-absorbable material is absorbed by the surrounding tissue, the elongated structure will return its relaxed state.

Figure 30A:
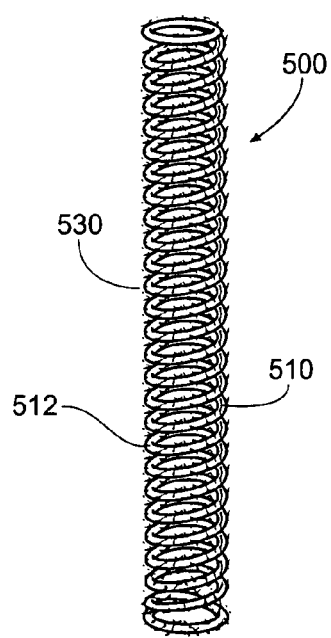
FIG. 30A is perspective view of the elastomeric body of FIG. 26D held in an extended state by a bio-absorbable material.
Figure 30B:
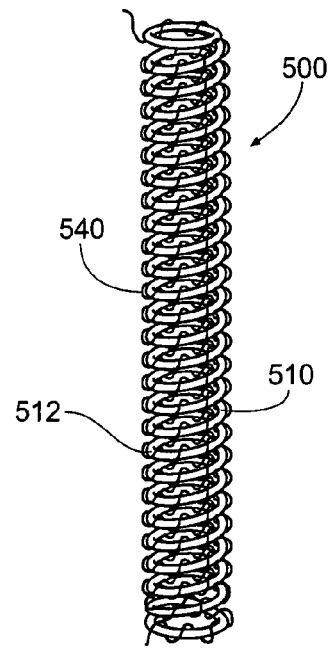
FIG. 30B is perspective view of the elastomeric body of FIG. 26D held in an extended state by an absorbable suture.
Figure 30C:
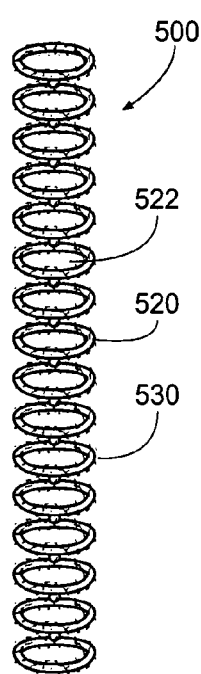
FIG. 30C is a perspective view of the elastomeric body of FIG. 27D held in an extended state by a bio-absorbable material.
Figure 30D:
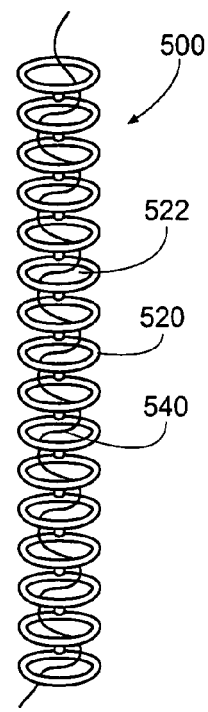
FIG. 30D is a perspective view of the elastomeric body of FIG. 27D held in an extended state by an absorbable suture.

In an alternative embodiment, structure 500 is placed in an extended stressed position by using absorbable sutures 540 wrapped around the coils 512 of structure 510 (see FIG. 30B) or threaded through the perforations of structure 500 (see FIG. 30D). Desirably, the mass absorption period of the absorbable sutures 540 used to fill the perforations 522 of structure 520 or the space between the coils 512 of structure 510 will be less than the amount of time necessary for tissue in-growth to start in the perforations 522 of structure 520 (FIG. 30D) or between the coils 512 of structure 510 (FIG. 30B) (usually about three weeks). In this manner, when the absorbent sutures are absorbed by the surrounding tissue, the elongated structure will return to its relaxed state.

Figure 30E:
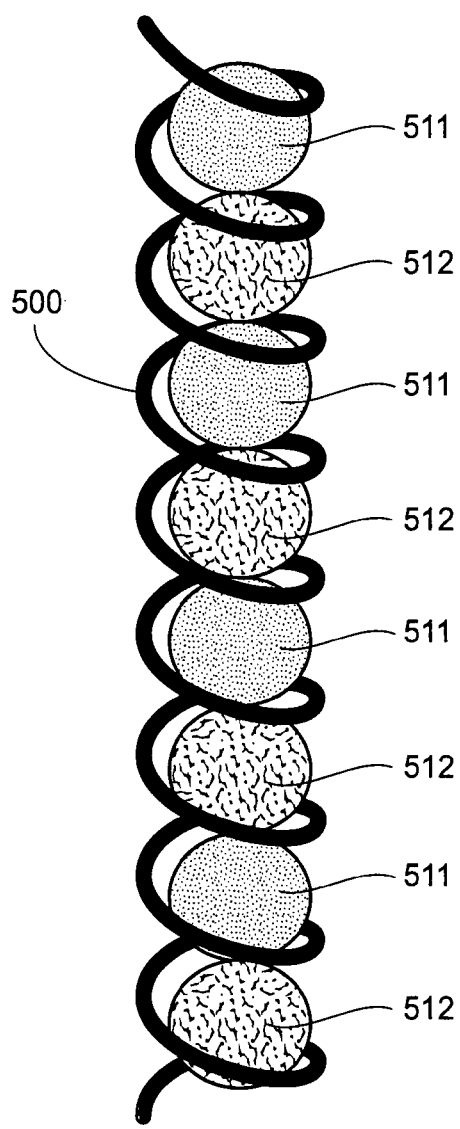
FIGS. 30E and 30F are perspective views of the elastomeric body of FIG. 27G held in an extended state by bioabsorbable beads.
Figure 30F:
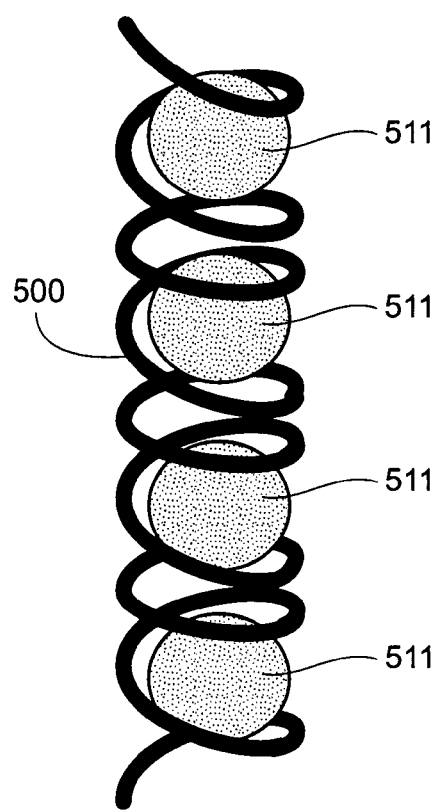

In yet another alternative embodiment seen in FIGS. 30E and 30F, structure 500 may be placed in an extended state by interspersing beads of material that biodegrades at different rates. As an example PGA beads 512 may be interspersed between poly-L-lactic acid (PLLA) beads 511, see FIG. 30E. PGA beads 512 will biodegrade at a much faster rate than PLLA 511 beads, thus allowing for a gradual return of structure 500 from a stressed/extended state to a relaxed/shortened state, see FIG. 30F.

Other methods (not illustrated) also contemplate placing a tube over an extended elongated elastomeric structure 500 and embedding the structure in a bioabsorbable material, while maintaining a centrally-located channel through the bioabsorbable material to allow the insertion of an anchor to be attached to one end of the structure 500. The tube covering the embedded elongated elastomeric structure would then be removed and the structure 500 would be implanted in the tongue tissue or muscle.

The elongated elastomeric structure 500 may be coupled to a tissue grasping member, which, in a first illustrated embodiment, takes the form of an anchor 550 implanted in the tongue 34. This anchor 550 secures the structure to the tongue. The anchor may be of any type known in the art. Representative examples include a stent anchor (see FIGS. 31A to 31C) and a daisy anchor (see FIGS. 33A to 33C).

Figure 31A:
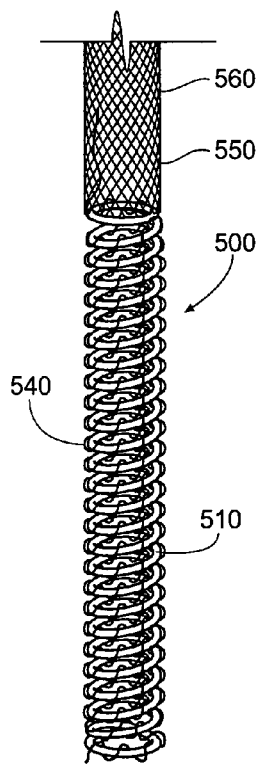
FIG. 31A is a perspective view of the elastomeric body of FIG. 30B further including a stent anchor.
Figure 31B:
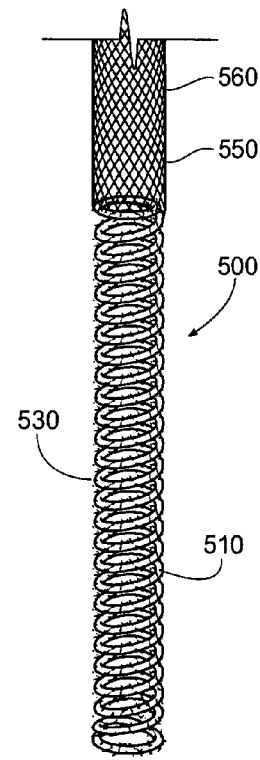
FIG. 31B is a perspective view of the elastomeric body of FIG. 30A further including a stent anchor.
Figure 31C:
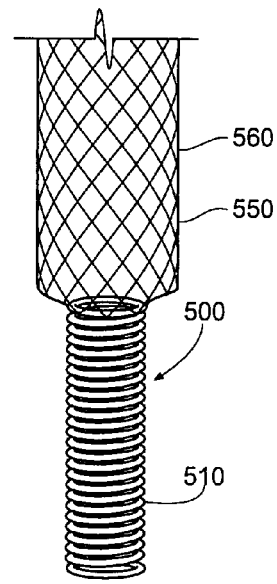
FIG. 31C is a perspective view of the elastomeric body of FIG. 31A or 31B wherein the spring has returned to its relaxed state and the stent anchor has deployed.

As shown in FIGS. 31A to 31C, a stent anchor 560, a shortened version of an angioplasty cardiovascular stent, can be used for securing the elastomeric structure in the tissue region. FIG. 31A shows the coil-shaped embodiment of the elastomeric structure retained in its extended position by the use of sutures, as described above. A stent anchor, shown in its undeployed position, is attached to one end of the coil. FIG. 31B shows the coil-shaped embodiment of the elastomeric structure retained in its extended position by the use of bio-absorbable material, as described above. A stent anchor, shown in its undeployed position, is attached to one end of the elongated elastomeric structure. FIG. 31C shows an elongated elastomeric structure 500 where the stent anchor 560 has been deployed and the elastomeric structure has returned to its relaxed state because bio-absorbable material or sutures were absorbed by the body.

Figure 32A:
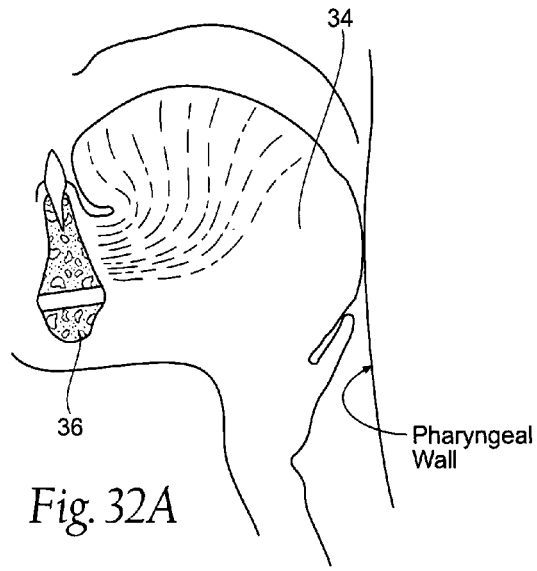
FIGS. 32A to 32C are anatomical sagittal views showing a method of inserting the elastomeric body of FIG. 31A or 31B in a human.
Figure 32B:
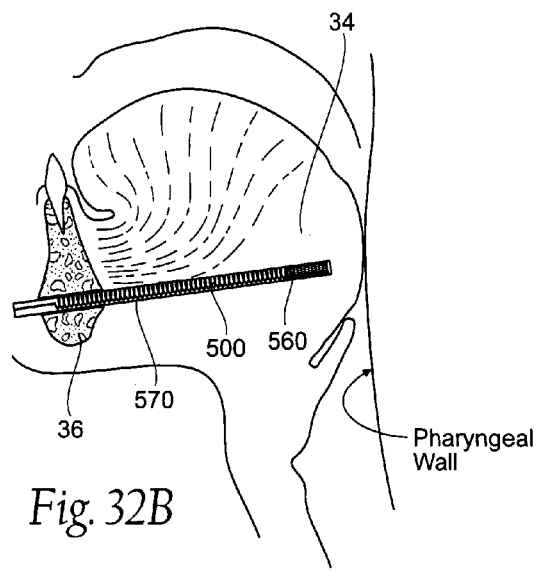
Figure 32C:
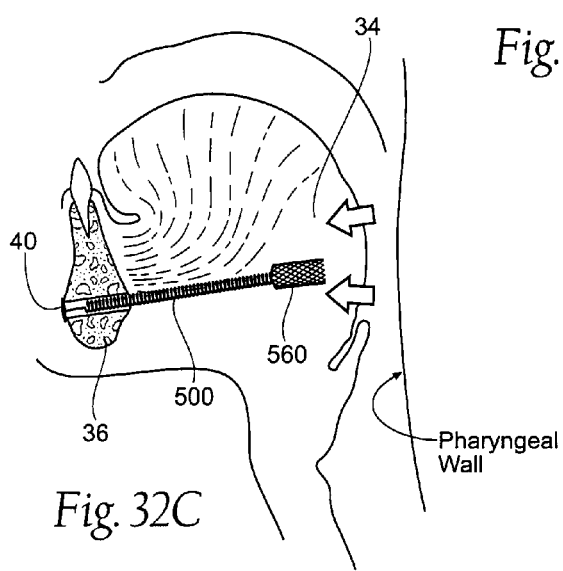

FIGS. 32A to 32C show a method of inserting the elongated elastomeric structure 500 with an attached stent anchor into the tissue of the tongue. First, a hole is formed through the mandible into the tongue tissue (see FIG. 32A). Next, a cannula pre-loaded with an elongated elastomeric structure 500 and attached stent anchor 560 is inserted into the hole such that the stent anchor is located at the posterior end of the tongue 34. As seen in FIG. 32C, once the implant is in its desired location, the stent anchor 560 is then deployed using any method (including but not limited to, self expansion or balloon expansion) known and practiced by those in the field of interventional cardiology involving neuro, peripheral vessels and the cannula is removed. A bar or button 40 may be attached to the elongated elastomeric structure 500 on the outer portion of the mandible 36 to retain the elongated elastomeric structure 500 in its position, as shown in FIG. 32C.

Figure 34A:
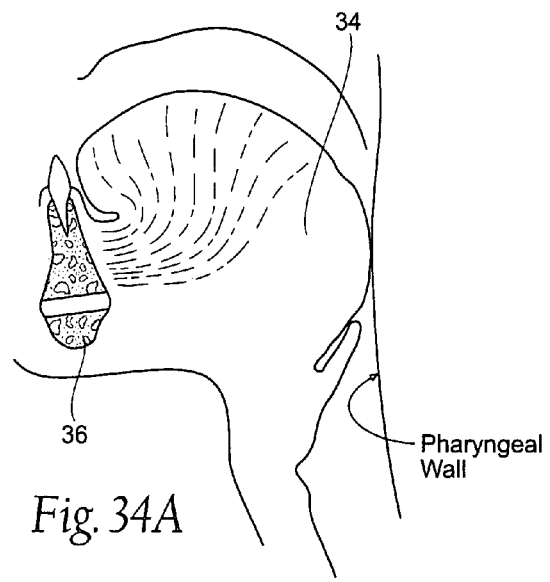
FIGS. 34A to 34C are anatomical sagittal views showing a method of inserting the elastomeric body of FIG. 33A or 33B in a human.
Figure 34B:
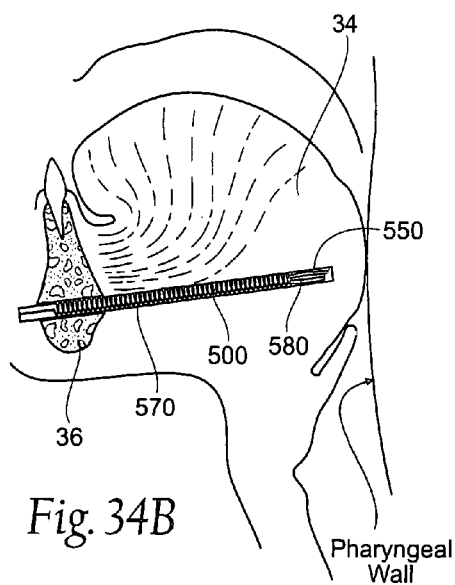
Figure 34C:
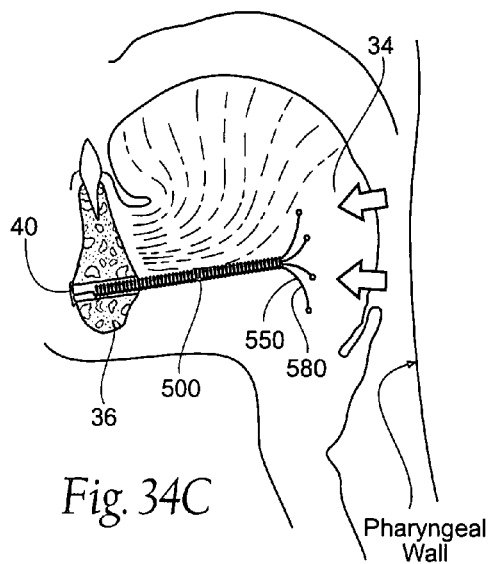
Figure 34D:
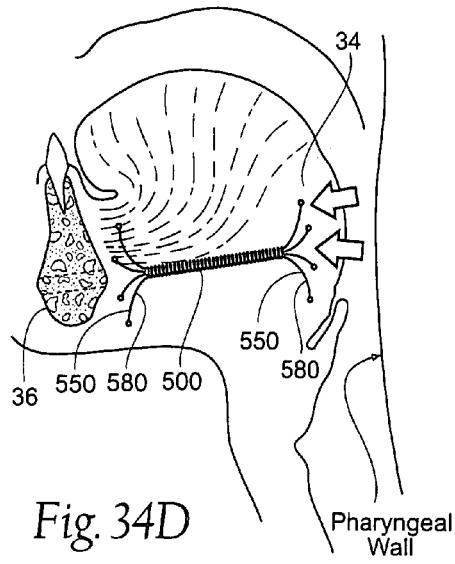
FIG. 34D is an anatomical sagittal view showing an alternate embodiment of the elastomeric body of FIG. 33A or 33B inserted in a human.

As seen in FIG. 34D, it is also contemplated that two self-deployable stent anchors 560 could be used, one on each end of the elongated elastomeric structure 500. This arrangement could eliminate the bar or button 40 shown in FIG. 32C.

As the bio-absorbable material 530 or absorbable sutures 540 are absorbed within the tissue region, the elongated elastomeric structure 500 implanted in the extrinsic muscle region develops gentle tension on the stent anchor 560, keeping the tongue tissue from collapsing posteriorly and thus maintaining the airway patent.

It is contemplated that the stent anchor may be deployed by collapsing the stent under pressure and enclosing it in a sheath. Once the implant is in its desired location, the sheath is pulled back and the stent anchor starts to return to its original expanded position, penetrating through and embedding itself further into the surrounding tissue. As the bio-absorbable material 530 or absorbable sutures 540 are absorbed within the tissue region, the elongated elastomeric structure 500 implanted in the extrinsic muscle region develops gentle tension on the stent anchor 560, keeping the tongue tissue from collapsing posteriorly and thus maintaining the airway patent.

The stent anchor can be removed by re-inserting a cannula-type device over the elongated elastomeric structure, collapsing the stent anchor and re-sheathing it.

Alternatively, (as shown in FIGS. 33A to 33C), the elongated elastomeric structure 500 may come equipped with at least one self-deployable daisy-type anchor 580, hereinafter "daisy anchor" for use in securing the elastomeric structure to the selected tissue region. FIG. 33A shows an elastomeric structure 500 retained in its expanded position by bio-absorbable material 530 with an undeployed daisy anchor 580 attached to one end. FIG. 33B shows an elastomeric structure 500 retained in its expanded position by absorbable sutures 540 with an undeployed daisy anchor 580 attached to one end. As seen in FIGS. 33A and 33B, the daisy anchor 580 comprises a plurality of "petals" or arms. When the daisy anchor 580 is in its undeployed position the arms are held in an essentially vertical position (see FIGS. 33A and 34B).

FIG. 31C shows an elastomeric structure 500 where the daisy anchor 580 has been deployed and the elastomeric structure 510 has been returned to its relaxed state because the bio-absorbable material 530 or sutures 540 have been absorbed by the body. As shown in FIG. 33C, when the daisy anchor 580 is deployed the "petals" or arms "bloom" or expand and thus penetrate the surrounding tissue to secure the elastomeric structure 500 in its desired position. The daisy anchor can be removed by re-inserting a cannula-type device over the elongated elastomeric structure and re-sheathing the anchor.

FIGS. 34A to 34C shows a method of inserting the elongated elastomeric structure 500 into the tissue of the tongue. First, a hole is formed through the mandible into the tongue (see FIG. 34A). As shown in FIG. 34B a cannula 570 pre-loaded with an elongated elastomeric structure 500 and a daisy anchor 580 attached on the end is then inserted into the tongue such that the daisy anchor 580 is located at the posterior end of the tongue 34. As seen in FIG. 34B, the elongated elastomeric structure 500 should be put in its extended stated, as was described above. The cannula 570 maintains the arms in the "deployment-ready" state, which is in an essentially vertical position.

As seen in FIG. 32C, once the implant is in its desired location, the daisy anchor 580 is then deployed by pulling out the cannula. When the cannula is retracted, the daisy anchor 580 arms expand and penetrate into the surrounding tissue to anchor the elongated elastomeric structure 500 into its desired location. A bar or button 40 may be attached to the elongated elastomeric structure 500 on the outer portion of the mandible 36 to assist in retaining the elongated elastomeric structure 500 in its position.

As the bio-absorbable material or absorbable sutures are absorbed within the tissue region, the elongated elastomeric structure 500 implanted in the extrinsic muscle region develops gentle tension on the stent anchor 560, keeping the tongue tissue from collapsing posteriorly and thus maintaining the airway patent.

As seen in FIG. 34D, it is also contemplated that two self-deployable daisy anchors 580 could be used, one on each end of the elongated elastomeric structure 500. This arrangement could eliminate the bar or button 40 shown in FIG. 34C.

It is also contemplated that the inside of the cannula can contain a plunger device, as is well known in the art, that pushes the elastomeric structure 500 with attached daisy anchor 580 into the tissue before the retraction of the cannula.

E. Tension Adjuster for the Tissue-Tensioning Elastomeric Structure

Figure 35A:
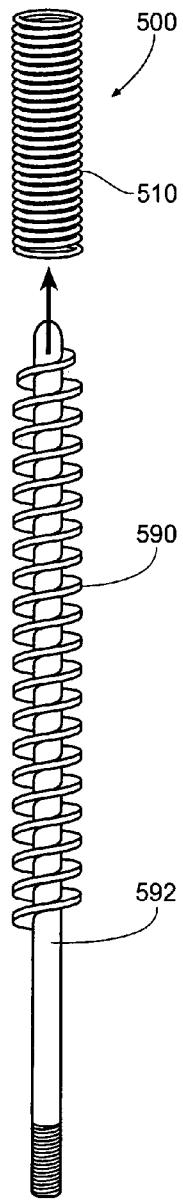
FIG. 35A is a perspective view of a spring expander for use with the elastomeric body of FIG. 26A.
Figure 35B:
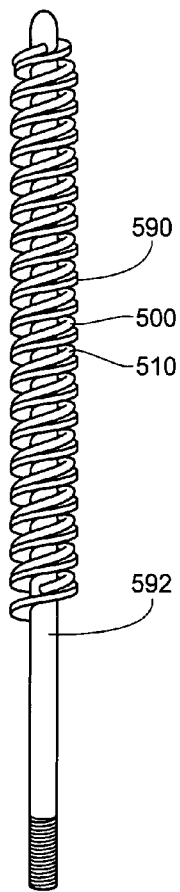
FIG. 35B is a perspective view of the spring expander of FIG. 35A with an elastomeric body threaded thereon.
Figure 35C:
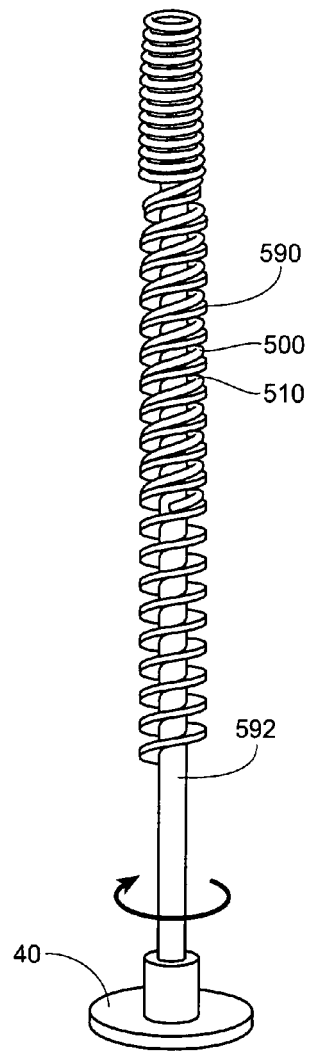
FIG. 35C shows the spring expander of FIG. 35B, wherein the tension in the elastomeric body is being adjusted by unthreading the spring expander from a portion of the elastomeric body.

FIGS. 35A to 35C show a representative example of a spring expander that may be used with the coiled spring structure 510 (as shown in FIG. 26A to 26D). As seen in FIG. 35A, the spring expander 590 is a flexible cylindrical shaft with a helical ridge or thread wrapped around it. The helical ridge begins near the proximal end of the flexible cylindrical shaft and mates with the complementary helix formed by the coiled spring structure 510. The flexible cylindrical shaft 592 is desirably made from a material such as titanium, Nitinol, or a polymer.

As seen in FIG. 35B, the process of inserting/twisting the cylindrical shaft 592 into the coiled spring structure 510 causes structure 500 to switch to its stressed, expanded position. As seen in FIGS. 35B and 35C, twisting part of the cylindrical shaft 592 out of the elongated elastomeric structure causes the corresponding part of the coiled spring structure 510 to switch to its relaxed position. The process of twisting in and out the cylindrical shaft 590 with respect to the coiled spring structure 510 allows the surgeon to control the tension exerted by and/or the elasticity of the structure 510 on the tissue where it has been implanted and to adjust this tension to maximize the therapeutic benefit.

As FIG. 35C shows, the cylindrical shaft 592 attached to an anchoring device 610. In use, the shaft 592 would extend through the mandible and the anchoring device would be located on the outside the mandible (see FIG. 36D). The anchoring device 610 may take any suitable forms already well-known in the art, such as buttons, sockets, etc. In the representative embodiment shown in FIG. 35C, the cylindrical shaft 592 may include an externally threaded portion at the distal end of the cylindrical shaft 592. The anchoring device 610 may include an internally threaded portion, such that the anchoring device 610 may be secured to the cylindrical shaft 592 by screwing the anchoring device 610 to the cylindrical shaft 592. Essentially, the length of the cylindrical shaft 592 may be adjusted at any of various locations of at the attachment point to the anchoring device 610.

In use, the coiled spring structure 510 will desirably come with a pre-inserted spring expander 590 (see FIG. 36C). However, it is also contemplated that during the surgery, the physician will twist the spring expander 590 into the coiled spring structure 510 to extend the coiled spring structure 510. The coiled spring structure 510 is placed and then maintained in a stressed, extended position by the twisting in of a flexible cylindrical shaft 592 with a complementary helix.

FIGS. 36A to 36E show a method of inserting a spring expander 590-coiled spring structure 510 assembly. FIG. 36C shows a spring expander with a pre-inserted coiled spring structure 510 with an anchor. The anchor may be of different types, including the stent anchor 560 and the daisy anchor 580; desirably, it will be self-deployable. In the illustrated embodiment, a daisy anchor 580 is be used, which can be deployed in the tissue region.

As seen in FIG. 36A, a hole is formed in the mandible. FIG. 36B shows the insertion of a trocar and cannula 570 assembly pre-loaded with: an elongated elastomeric structure 510, a daisy anchor 580 attached to the distal end of structure 510, and a spring expander 590 twisted into the proximal end (to be located in the anterior portion of the oral cavity) of structure 510.

As seen in FIGS. 36D and 36E, once the implant is in its desired location, the daisy anchor 580 is then deployed by pulling out the cannula causing the daisy anchor 580 to "bloom", where the "petals"/arms penetrate into the surrounding tissue to anchor the elongated elastomeric structure 500 into its desired location. Once the daisy anchor 580 at the distal end of the coiled spring structure 510 is self-deployed, it secures the distal end of the coiled spring structure 510. The surgeon then adjusts the tension exerted by the coiled spring structure 510 on the tissue where it has been implanted to maximize the therapeutic benefit and attaches the flexible cylindrical shaft to the hole in the mandible by any of a variety of means familiar to those experienced in this art (see FIGS. 36D and 36E).

As seen in FIG. 36D, a button 40 may be attached to the spring expander 590 on the outer portion of the mandible 36 to retain spring expander 590 and associated coiled spring structure 510 in its position.

Future adjustments to the tension in the elongated elastomeric structure can be easily performed under local anesthesia in the surgeon's office. To perform adjustments, the button 40 would be removed from the end of the spring expander 590. The spring expander 590 would then be rotated to adjust the coiled spring structure 510 as needed. Rotating the spring expander 590 in a first direction would cause more of the spring structure 510 to be in the relaxed position and would increase the tension in the spring structure 510. Rotating the spring expander 590 in an opposite, second direction would cause more of the spring structure 510 to be in the extended position and would decrease the tension in the spring structure 510. The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims. The scope of this invention shall be determined from the scope of the following claims, including their equivalents.

We claim:

1. An implant system comprising:
   at least one elongated body sized and configured for surgical implantation in a desired orientation, including a state of tension, in a tissue region in an airway, the elongated body having an insertion end and an opposite trailing end,
   an array of projections extending from the elongated body and being resiliently coupled to the elongated body in a normally biased outward extending condition sized and configured to penetrate into and engage tissue and resist a reorientation of the elongated body within the tissue region out of the desired orientation after surgical implantation of the elongated body in the tissue region, the array of projections being sized and configured to resiliently yield by flexing inward against the elongated body during surgical implantation of the elongated body in the tissue region, and
   an adjustment component adjustably coupled to the trailing end, the component being adapted to adjust the state of tension in the elongated body when implanted, wherein the adjustment component comprises:
     a first component adapted to be rigidly coupled in or near the tissue region, and
     a second component adjustably coupled to the elongated body, the second component being selectively adjustable with respect to the first component in a manner that adjusts positioning of the elongated body with respect to the first component.

2. An implant system according to claim 1 wherein the second component is adjustably coupled to the first component in a manner that allows the second component to rotate with respect to the first component.

3. An implant system according to claim 1 wherein the desired orientation of the elongated body includes a curvilinear configuration.

4. An implant system according to claim 1 wherein the elongated body comprises a flexible material.

5. An implant system according to claim 1 wherein the elongated body comprises a suture material.

6. An implant system according to claim 1 wherein at least one of the projections comprises a flexible material.

7. An implant system according to claim 1 wherein at least one of the projections comprises a barb.

8. An implant system according to claim 1 wherein the elongated body is sized and configured for implantation in a desired orientation in a palate.

9. An implant system according to claim 1 wherein the elongated body is sized and configured for implantation in a desired orientation in a uvula.

10. An implant system according to claim 1 wherein the elongated body is sized and configured for implantation in a desired orientation in a tongue.

11. An implant system according to claim 1 wherein the elongated body is sized and configured for implantation in a desired orientation in an epiglottis.

12. An implant system according to claim 1 wherein the elongated body is sized and configured for implantation in a desired orientation in a muscle along an upper respiratory tract.

13. An implant system according to claim 1 further including a tissue anchor coupled to the elongated body.

14. An implant system according to claim 1 further including a bone anchor coupled to the elongated body.

15. A method comprising
selecting a tissue region in an airway, and
providing at least one elongated body sized and configured for surgical implantation in a desired orientation, including a state of tension, in the tissue region, the elongated body including an insertion end, an opposite trailing end, and an array of projections extending from the elongated body and being resiliently coupled to the elongated body in a normally biased outward extending condition sized and configured to penetrate into and engage tissue and resist a reorientation of the elongated body within the tissue region out of the desired orientation after surgical implantation of the elongated body in the tissue region, the array of projections being sized and configured to resiliently yield by flexing inward against the elongated body during surgical implantation of the elongated body in the tissue region, and
surgically implanting the at least one elongated body to stabilize a desired orientation of the tissue region, and
adjusting the tension in the elongated body by adjusting an adjustment component adjustably coupled to the trailing end.

16. A method according to claim 15 wherein the tissue region selected includes a palate.

17. A method according to claim 15 wherein the tissue region selected includes a uvula.

18. A method according to claim 15 wherein the tissue region selected includes a tongue.

19. A method according to claim 15 wherein the tissue region selected includes an epiglottis.

20. A method according to claim 15 wherein the tissue region selected includes a muscle along an upper respiratory tract.

21. A method according to claim 15 wherein implanting includes placing the at least one elongated body in a state of tension in the tissue region.

22. A method according to claim 15 wherein implanting includes anchoring the at least one elongated body to tissue.

23. A method according to claim 15 wherein implanting includes anchoring the at least one elongated body to bone.

24. A method according to claim 15 wherein implanting includes placing the at least one elongated body in a curvilinear orientation.

25. A method according to claim 15 wherein implanting includes passing the elongated body through an implantation tool.

* * * * *